(12) United States Patent
Brennan et al.

(10) Patent No.: US 8,586,308 B2
(45) Date of Patent: Nov. 19, 2013

(54) GENETIC MARKERS OF MENTAL ILLNESS

(75) Inventors: Mark David Brennan, Jeffersonville, IN (US); Timothy Lynn Ramsey, Shelbyville, KY (US)

(73) Assignee: SureGene, LLC, Louisville, KY (US)

( * ) Notice: Subject to any disclaimer, the term of this patent is extended or adjusted under 35 U.S.C. 154(b) by 282 days.

(21) Appl. No.: 12/523,262

(22) PCT Filed: Jan. 16, 2009

(86) PCT No.: PCT/US2009/031322
§ 371 (c)(1),
(2), (4) Date: Jan. 26, 2010

(87) PCT Pub. No.: WO2009/092032
PCT Pub. Date: Jul. 23, 2009

(65) Prior Publication Data
US 2010/0279285 A1 Nov. 4, 2010

Related U.S. Application Data

(60) Provisional application No. 61/021,756, filed on Jan. 17, 2008.

(51) Int. Cl.
*C12Q 1/68* (2006.01)

(52) U.S. Cl.
USPC .......................................... 435/6.11; 435/6.1

(58) Field of Classification Search
None
See application file for complete search history.

(56) References Cited

U.S. PATENT DOCUMENTS

| | | | |
|---|---|---|---|
| 2003/0008301 A1 | 1/2003 | Sklar et al. | |
| 2006/0177851 A1 | 8/2006 | Brennan et al. | |
| 2006/0276412 A1* | 12/2006 | Tollefson .................... | 514/23 |
| 2009/0012371 A1 | 1/2009 | Brennan et al. | |

FOREIGN PATENT DOCUMENTS

| WO | WO 2003/101377 A | 12/2003 |
|---|---|---|
| WO | WO 2006/023719 A | 3/2006 |
| WO | WO 2006/072075 A | 7/2006 |
| WO | WO 2009/008896 A | 1/2009 |
| WO | WO 2009/082743 | 7/2009 |
| WO | WO 2009/089120 | 7/2009 |

OTHER PUBLICATIONS

Lo, WS et al. Molecular Psychiatry 2004 vol. 9 pp. 603-608.*
GenBank dp SNP database entry for rs736845 (Oct. 16, 2000).*
GenBank dp SNP database entry for rs994060 (Oct. 16, 2000).*
GenBank dp SNP database entry for rs381579 (Jul. 24, 2000).*
rsl 7785419 entry in the dbSNP (SNP database), accessed Nov. 1, 2012 from: http://www.ncbi.nlm.nih.gov/projects/SNP/snp_ref.cgi?rs=17785419, 3 pages.*
McElroy et al., AAPS Pharmsci, 2000, vol. 2, pp. 1-11.*
Rosenheck et al., American Journal of Psychiatry, 2006, vol. 163, pp. 2080-2089.*
Badner et al., "Meta-analysis of whole-genome linkage scans of bipolar disorder and schizophrenia," Molecular Psychiatry, vol. 7, pp. 405-411 (2002).
Bajestan et al., "Association of AKT1 halotype with the risk of schizophrenia in Iranian population," American Journal of Medical Genetics, Part B, Neuropsychiatric Genetics, vol. 141B, No. 4, Jun. 5, 2006, pp. 383-386.
Baker et al., "*COMT* Val $^{108/158}$ Met Modifies Mismatch Negativity and cognitive Function in 22q11 Deletion Syndrome," Biol. Psychiatry, vol. 58(1), pp. 23-31 (2005).
Bakker et al "The *PIP5K2A* and RGS4 genes are differentially associated with deficit and non-defcit schizophrenia," Genes, Brain and Behavior, vol. 6, pp. 113-119 (2007).
Bennett et al., "The Wellcome trust UK-Irish bipolar affective disorder sibling-pair genome screen: first stage report," Molecular Psychiatry, vol. 7, pp. 189-200 (2002).
Bertolino et al., "COMT Val<158>Met polymorphism predicts negative symptoms response to treatment with olanzapine in schizophrenia," Schizophrenia Research, vol. 95, No. 1-3, Aug. 29, 2007, pp. 253-672.
Cadenhead M.D., "Vulnerability markers in the schizophrenia spectrum: implications for phenomenology, genetics, and the identification of the schizophrenia prodrome," Psychiatric Clinics of North America, vol. 25(4), pp. 837-853 (2002).
Callicott et al., Variation in dISC1 affects hippocampal structure and function and increases risk for schizophrenia, Proc. Natl. Acad. Sci USA vol. 102(24), pp. 8627-8632 (2005).
Cannon et al., "Association of *DISC1/TRAX* Haplotypes With Schizophrenia, Reduced Prefrontal Gray Matter, and impaired Short- and Long-term Memory," Arch Gen Psychiatry vol. 62(11): pp. 1205-1213 (2005).
Cooper-Casey et al., "Suggestive linkage of schizophrenia to 5p13 in Costa Rica," Molecular Psychiatry, vol. 10, pp. 651-656 (2005).
Davis et al., "Statistical Approaches to Effectiveness Measurement and Outcome-Driven Re-Radnomizations in the Clinical Antipsychotic Trials of Intervention Effectiveness (CATIE) Studies," Schizophrenia Bulletin, vol. 29, pp. 73-80 (2003).
Devlin et al., "Genome-wide multipoint linkage analyses of multiplex schizophrenia pedigree from the oceanic nation of Palau," Molecular Psychiatry, vol. 7, pp. 689-694 (2002).
Fallin et al., "Genome Linkage Scan for Schizophrenia Susceptibility Loci among Ashkenazi Jewish Families Shows Evidence of Linkage on Chromosome 10q22," Am. J. Hum. Genet. vol. 73, pp. 601-611 (2003).
Fallin et al., "Bipolar I Disorder and Schizophrenia: A 440-Single-Nucleotide Polymorphism Screen of 64 Candidate Genes among Ashkenazi Jewish Case-Parent Trios," Am. J. Hum. Genet, vol. 77, pp. 918-936 (2005).
Ginns et al., "A genome-wide search for chromosomal loci linked to mental health wellness in relatives at high risk for bipolar affective disorder among the Old Order Amish," Proc. Natl. Acad. Sci. U.S.A., vol. 95, pp. 15531-15536 (1998).

(Continued)

*Primary Examiner* — Anne Gussow
*Assistant Examiner* — Mindy G Brown
(74) *Attorney, Agent, or Firm* — Fish & Richardson P.C.

(57) ABSTRACT

This invention relates to genetic markers of mental illness, e.g., schizophrenia (SZ), and methods of use thereof.

30 Claims, 3 Drawing Sheets

(56) References Cited

OTHER PUBLICATIONS

Gornick et al., "Dysbindin (DTNBP1, 6p22.3) is Associated with Childhood-Onset Psychosis and Endophenotypes Measured by the Premorbid Adjustment Scale (PAS)," Journal of Autism Development Disorders, vol. 35, pp. 831-838 (2005).

Gothelf et al., "*COMT* genotype predicts longitudinal cognitive decline and psychosis in 22q11.2 deletion syndrome," Natural Neuroscience, vol. 8(11), pp. 1500-1502 (2005).

Gottesman and Gould, "The Endophenotype Concept in Psychiatry: Etymology and Strategic Intentions," Am. J. Psychiatry, vol. 160(4), pp. 636-645 (2003).

Gutierrez et al., "Identification of two rish haplotypes for schizophrenia and bipolar disorder in the synaptic vesicle monoamine transporter gene (SVMT)," American Journal of Medical Genetics, Part B, Neuropsychiatric Genetics, vol. 144B No. 4, Jun. 5, 2007, pp. 502-507.

Hallmayer et al., "Genetic Evidence for a Distinct Subtype of Schizophrenia Characterized by Pervasive Cognitive Deficit," Am J. Hum. Genet, vol. 77(3), pp. 468-476 (2005).

Harrison and Owen, "Genes for Schizophrenia? Recent findings and their pathophysiological implications," Lancet, vol. 361(9355): pp. 417-419 (2003).

Hennah et al., "Haplotype analysis and identification of genes for a complex trait: examples from schizophrenia," Annals of Medicine, vol. 36, No. 5, pp. 322-331 (2004).

Heinrichs, "Meta-analysis and the science of schizophrenia: variant evidence or evidence of variants?," Neuroscience & Biohavorial Reviews, vol. 28(4): pp. 379-394 (2004).

Ivkovic et al., "Sxhizophrenia and Polymorphic CAG Repeats Array of Calcium-Activated Potassium Channel (*KCNN3*) Gene in Serbian Popluation," Intern. J. Neuroscience, vol. 116, pp. 157-164 (2006).

Jablensky, "Subtyping schizophrenia: implications for genetic research," Molecular Psychiatry, vol. 11, pp. 815-836 (2006).

Kalkman, "The role of the phosphatidylinositide 3-kinase-protein kinase B pathyway in schizophrenia," Pharmacology and Therapeutics, vol. 110, pp. 117-134 (2006).

Kay et al., "The Positive and Negative Syndrome Scale (PANSS) for Schizophrenia," Schizophr. Bulletin, vol. 13(2), pp. 261-276 (1987).

Kendler et al., "Evaluating the Spectrum Concept of Schizophrenia in the Roscommon Family Study," Am. J. Psychiatry, vol. 152(5), pp. 749-754 (1995).

Kirov et al., "Finding schizophrenia genes," The Journal of Clinical Investigations, vol. 115, pp. 1440-1448 (2005).

Leucht et al., "What does the PANSS mean?," Schizophrenia Research, vol. 29, pp. 231-238 (2005).

Lieberman et al., "Effectiveness of Antipsychotic Drugs in Patients with Chronic Schizophrenia," The New England Journal of Medicine, vol. 353, pp. 1209-1223 (2005).

Lin et al., "The relationship between P-glycoprotein (PGP) polymorphisms and response to olanzapine treatment in schizophrenia," Therapeutic Drug Monitoring, vol. 28, No. 5, Oct. 2006, pp. 668-672.

Mancama et al., "Choline acetyltransferase variants and their influence in schizophrenia and olanzapine response," American Journal of Medical Genetics, Part B, Neuropsychiatric Genetics, vol. 144B, No. 7, Oct. 5, 2007, pp. 849-853.

Norton et al.., "An update on the genetics of schizophrenia," Current Opinion in Psychiatry, vol. 19(2), pp. 158-164 (2006).

Owen et al., "The molecular genetics of schizophrenia: new findings promise new insights," Molecular Psychiatry, vol. 9, pp. 14-27 (2004).

Purcell et al., "PLINK: A Tool Set for Whole-Genome Association and Population-Based Linkage Analyses," The American Journal of Human Genetics, vol. 81, pp. 559-575 (2007).

Riley et al., "Molecular genetic studies of schizophrenia," European Journal of Human Genetics, vol. 14, Jun. 6, 2008, pp. 669-680.

Sullivan et al., "Genomewide association for schizophrenia in the CATIE study: results of stage 1," Molecular Psychiatry, vol. 13, No. 6, Jun. 2008, pp. 570-584.

Stroup et al., "The National Institute of Mental Health Clinical Antipsychotic Trials of Intenrvention Effectiveness (CATIE) Project: Schizophrenia Trial Design and Protocol Development," Schizophrenia Bulletin, vol. 29, pp. 15-31 (2003).

Woo et al., "Quality assessment of buccal versus blood genomic DNA using the Affymetrix 500 K GeneChip," BMC Genetics, vol. 8, No. 1, Nov. 8, 2007, p. 79.

Zobel et al., "Endophänotypen—ein neues Konzept zur biologischen Charakterisierung psychischer Störungen," Nervenarzt, vol. 75, pp. 205-214 (2004). English abstract on p. 207.

Canavier et al., "Computational model predicts a role for ERG current in repolarizing plateau potentials in dopamine neurons: implications for modulation of neuronal activity," Neurophysiol. 98:3006-3022 (2007).

Communication issued by the European Patent Office for EP Application No. 09702855.9 dated Jan. 4, 2011; 6 pages.

Notification Concerning Transmittal of International Preliminary Report on Patentability; and International Preliminary Report on Patentability, Patent Cooperation Treaty, PCT Application No. PCT/US2009/031322, mailed Jul. 29, 2010. 14 pages.

Notification Concerning Transmittal of the International Search Report and the Written Opinion; and International Search Report and Written Opinion, Patent Cooperation Treaty, PCT Application No. PCT/US2009/031322, mailed Jun. 12, 2009. 24 pages.

\* cited by examiner

Figure 1A

| GENE | NCBI ACCESSION NUMBER FOR GENOMIC DNA |
|---|---|
| ADAM10 | NC_000015.8 (56675802..56829469, complement) |
| AKAP13 | NC_000015.8 (83724875..84093590) |
| ANK3 | NC_000010.9 (61458165..61819494, complement) |
| BEAN | NC_000016.8 (65018120..65074249) |
| BEGAIN | NC_000014.7 (100073240..100105884, complement) |
| BMP7 | NC_000020.9 (55178962..55274708, complement) |
| BRSK2 | NC_000011.8 (1367705..1439908) |
| C16orf74 | NC_000016.8 (84298624..84342190, complement) |
| CACNA1E | NC_000001.9 (179719339..180037339) |
| CAMK1G | NC_000001.9 (207823668..207853907) |
| CAMTA1 | NC_000001.9 (6767971..7752351) |
| CBLN1 | NC_000016.8 (47870196..47873193, complement) |
| CDH11 | NC_000016.8 (63538184..63713420, complement) |
| CDH8 | NC_000016.8 (60244736..60627537, complement) |
| CHFR | NC_000012.10 (131927011..131974257, complement) |
| COX10 | NC_000017.9 (13913444..14052719) |
| CTNND1 | NC_000011.8 (57285810..57343228) |
| DAAM1 | NC_000014.7 (58725152..58906224) |
| DACT1 | NC_000014.7 (58174510..58184792) |
| DCC | NC_000018.8 (48120569..49311780) |
| DEAF1 | NC_000011.8 (634225..685740, complement) |
| DNM3 | NC_000001.9 (170077261..170648480) |
| DPH3 | NC_000003.10 (16276969..16281490, complement) |
| DTX4 | NC_000011.8 (58696388..58732636) |
| DUSP8 | NC_000011.8 (1531857..1549726, complement) |
| DYM | NC_000018.8 (44824170..45241077, complement) |
| EML1 | NC_000014.7 (99329498..99478150) |
| EVL | NC_000014.7 (99601504..99680326) |
| EXOC2 | NC_000006.10 (430138..638109, complement) |
| FASLG | NC_000001.9 (170894808..170902636) |
| FUSSEL18 | NC_000018.8 (43000291..43029552, complement) |
| Gcom1 | NC_000015.8 (55671406..55797045) |
| GOT2 | NC_000016.8 (57298536..57325747, complement) |
| GPR135 | NC_000014.7 (58999993..59001812, complement) |
| GRINL1A | NC_000015.8 (55786193..55797045) |
| HCCA2 | NC_000011.8 (1447269..1458691, complement) |
| HERC2 | NC_000015.8 (26029781..26240890, complement) |
| HSD17B12 | NC_000011.8 (43658719..43834745) |

Figure 1B

| GENE | NCBI ACCESSION NUMBER FOR GENOMIC DNA |
|---|---|
| IGF1R | NC_000015.8 (97010284..97325282) |
| JPH4 | NC_000014.7 (23107087..23117834, complement) |
| KATNAL2 | NC_000018.8 (42780785..42881661) |
| KCNA10 | NC_000001.9 (110861362..110863320, complement) |
| KCNC1 | NC_000011.8 (17714090..17750755) |
| KCNC4 | NC_000001.9 (110555588..110578189) |
| KCND3 | NC_000001.9 (112119977..112333300, complement) |
| KCNH1 | NC_000001.9 (208923178..209374080, complement) |
| KCNQ1 | NC_000011.8 (2422797..2826916) |
| KIAA0182 | NC_000016.8 (84204425..84267313) |
| KIAA0427 | NC_000018.8 (44319425..44643582) |
| KIAA0513 | NC_000016.8 (83618911..83685337) |
| KIAA1545 | NC_000012.10 (131577230..131671848) |
| KIAA1853 | NC_000012.10 (117903779..118085240) |
| KLHL25 | NC_000015.8 (84103561..84139193, complement) |
| LRRC4C | NC_000011.8 (40092329..40272240, complement) |
| N4BP1 | NC_000016.8 (47130138..47201621, complement) |
| NAV2 | NC_000011.8 (19691488..20099723) |
| NDRG2 | NC_000014.7 (20554762..20563775, complement) |
| NDRG4 | NC_000016.8 (57055118..57105024) |
| NEDD4 | NC_000015.8 (53906412..54073127, complement) |
| NETO2 | NC_000016.8 (45672943..45735409, complement) |
| OTOG | NC_000011.8 (17525496..17624067) |
| PER3 | NC_000001.9 (7767350..7827824) |
| PHACS | NC_000011.8 (44044433..44062145) |
| PMP22 | NC_000017.9 (15073821..15109369, complement) |
| PRDM2 | NC_000001.9 (13903937..14024162) |
| PTPN5 | NC_000011.8 (18706051..18769965, complement) |
| RABGAP1L | NC_000001.9 (172395257..173193950) |
| RERE | NC_000001.9 (8335051..8800286, complement) |
| RGMA | NC_000015.8 (91387641..91433437, complement) |
| RHOG | NC_000011.8 (3804784..3818789, complement) |
| RIMBP2 | NC_000012.10 (129446634..129568363, complement) |
| RP1-21O18.1 | NC_000001.9 (14797800..15317131) |
| RTN1 | NC_000014.7 (59132447..59407310, complement) |
| RTN4RL2 | NC_000011.8 (56984915..57000960) |
| SERGEF | NC_000011.8 (17766171..17991213, complement) |
| SLC16A4 | NC_000001.9 (110707028..110735159, complement) |

Figure 1C

| GENE | NCBI ACCESSION NUMBER FOR GENOMIC DNA |
|---|---|
| SLC17A6 | NC_000011.8 (22316243..22357619) |
| SLC6A17 | NC_000001.9 (110494631..110546347) |
| SLC6A5 | NC_000011.8 (20577522..20633186) |
| SLCO3A1 | NC_000015.8 (90197950..90507783) |
| SMAD2 | NC_000018.8 (43613464..43711510, complement) |
| SMAD4 | NC_000018.8 (46810611..46860145) |
| SMAD7 | NC_000018.8 (44700221..44731079, complement) |
| STX2 | NC_000012.10 (129840098..129889764, complement) |
| SV2B | NC_000015.8 (89570107..89639654) |
| SYT13 | NC_000011.8 (45218429..45264383, complement) |
| SYT14 | NC_000001.9 (208178161..208404259) |
| TEP1 | NC_000014.7 (19905766..19951420, complement) |
| TMEPAI | NC_000020.9 (55656858..55719947, complement) |
| TOLLIP | NC_000011.8 (1252177..1287415, complement) |
| TTC5 | NC_000014.7 (19827144..19843976, complement) |
| ULK1 | NC_000012.10 (130945232..130973649) |
| UNC13C | NC_000015.8 (52092393..52708098) |
| USH1C | NC_000011.8 (17472018..17522539, complement) |
| VAMP4 | NC_000001.9 (169938783..169977837, complement) |
| WDR25 | NC_000014.7 (99912703..100066393) |
| YPEL4 | NC_000011.8 (57169137..57173993, complement) |
| ZFP91-CNTF | NC_000011.8 (58103163..58145091) - NC_000011.8 (58146721..58149778) |
| ZNF423 | NC_000016.8 (48082022..48418419, complement) |

GENETIC MARKERS OF MENTAL ILLNESS

CROSS-REFERENCE TO RELATED APPLICATIONS

This application is the U.S. National Stage under 35 USC §371 of International Application Number PCT/US2009/031322, filed on Jan. 16, 2009, which claims the benefit of U.S. Provisional Patent Application Ser. No. 61/021,756, filed on Jan. 17, 2008; the entire contents of the foregoing are hereby incorporated by reference.

CLAIM OF PRIORITY

This application claims the benefit of U.S. Provisional Patent Application Ser. No. 61/021,756, filed on Jan. 17, 2008, the entire contents of which are hereby incorporated by reference.

FEDERALLY SPONSORED RESEARCH OR DEVELOPMENT

This invention was made with Government support under Grant Nos. R43 MH078437, N01 MH900001, and MH074027, awarded by the National Institutes of Health. The Government has certain rights in the invention.

ACKNOWLEDGEMENT

This invention was made with an award from the Kentucky Cabinet for Economic Development, Department of Commercialization and Innovation, under Grant Agreement KSTC-184-512-07-007 with the Kentucky Science and Technology Corporation.

TECHNICAL FIELD

This invention relates to genetic markers of mental illness, e.g., schizophrenia (SZ), and methods of use thereof, e.g., for determining a subject's risk of developing a mental illness, e.g., SZ.

BACKGROUND

Schizophrenia (SZ) is a severe and persistent debilitating psychiatric illness that is generally associated with considerable morbidity and extreme disability. Due to the severity of this disorder, especially the negative impact of a psychotic episode on a patient, and the diminishing recovery after each psychotic episode, there is a need to more conclusively identify individuals who have or are at risk of developing SZ, for example, to confirm clinical diagnoses, to allow for prophylactic therapies, to determine appropriate therapies based on their genotypic subtype, and to provide genetic counseling for prospective parents with a history of the disorder.

Various genes and chromosomes have been implicated in etiology of SZ. Whole genome scans for genes involved in SZ and related SZ-spectrum disorders (including schizotypal personality disorder (SPD) and schizoaffective disorder (SD)) have implicated numerous autosomes as having a role in the genetic etiology of SZ and related SZ-spectrum disorders (Badner et al., Mol. Psychiatry 7:405-411 (2002) Bennett et al., Mol. Psychiatry 7:189-200 (2002) Cooper-Casey et al., Mol. Psychiatry 10:651-656 (2005) Devlin et al., Mol. Psychiatry 7:689-694 (2002) Fallin et al., Am. J. Hum. Genet. 73:601-611 (2003) Ginns et al., Proc. Natl. Acad. Sci. U.S.A 95:15531-15536 (1998) Jablensky, Mol. Psychiatry (2006) Kirov et al., J. Clin. Invest 115:1440-1448 (2005) Norton et al., Curr. Opin. Psychiatry 19:158-164 (2006) Owen et al., Mol. Psychiatry 9:14-27 (2004)). Generally, these linkage scans have are too low in resolution to identify specific genes, but increasingly, transmission disequilibrium (TDT, family-based association) and Case/Control association studies have evaluated a number of positional candidate genes with a good measure of success (Fallin et al., Am. J. Hum. Genet. 77:918-936 (2005)).

SUMMARY

The invention includes methods for assessing genetic risk, aiding in diagnosis, and/or stratifying patient populations in order to select optimal treatments based on evaluation of single nucleotide polymorphisms (SNPs) for a number of bioinformatically identified genes on chromosomes 1, 3, 6, 10, 11, 12, 13, 14, 15, 15, 17, 18, 19, and 20 relating to SZ (which herein is broadly defined to include SZ-spectrum disorders, e.g., including schizophrenia (SZ), schizotypal personality disorder (SPD) and schizoaffective disorder (SD)). Exemplary SNPs delimiting each gene region (referred to herein as "delimiting SNPs") are given along with exemplary test SNPs that can be used to capture significant haplotype variation in these genes. Important variants can be identified via TDT using families with multiple affected individuals (such as those collected CCGS) and verified by Case/Control comparisons using the SNP markers presented herein. Using SNP markers lying between the delimiting SNPs, inclusive, and identical to or in linkage disequilibrium with the exemplary SNPs, one can determine the haplotypes in these genes relating to genetic risk of developing SZ. These haplotypes can then be used to determine risk of developing SZ by Case/Control studies as shown in Example 1. The allelic and genotypic variants thus identified can be used for assessing genetic risk, to aid in diagnosis, and/or to stratify patient population in order to select optimal treatments (atypical antipsychotic, typical antipsychotic, and/or psychosocial intervention) for patients.

Numerous pathways have been implicated in SZ etiology. As described herein, genes identified as associated with increased risk of SZ are involved in a number of pathways including: glutamate signaling and metabolism, cell adhesion, cytoskeletal architecture, vesicle formation and trafficking, G-protein coupled receptors, carrier proteins and transporters, ion channels (e.g., potassium channels), and potassium current signaling molecules, cell cycle modulators, neuronal development, calcium/calmodulin signaling, neuropeptide signaling, inositol signaling (e.g., phosphatidylinositol kinases), insulin signaling, diacylglycerol signaling, and several additional genes identified by virtue of their interaction with genes in high impact pathways and their expression in the central nervous system.

Table A lists gene names and delimiting SNPs for bioinformatically identified genes relating to SZ-spectrum disorders. All of the genes are human.

TABLE A

Delimiting SNPs for Novel SZ Genes (NCBI Genome Build 36.2)

| Gene | Chrom. | SNP 1 | Location (bp) | SNP 2 | Location (bp) |
|---|---|---|---|---|---|
| *Delimiting SNPs for Potassium Channel and Related Genes* | | | | | |
| KCNC4 | 1 | rs1359149 | 110,553,057 | rs11578913 | 110,578,628 |
| KCNA10 | 1 | rs1281177 | 110,859,992 | rs17025957 | 110,863,572 |
| KCND3 | 1 | rs197422 | 112,119,035 | rs10745323 | 112,345,127 |
| KCNH1 | 1 | rs12126648 | 208,922,743 | rs1538287 | 209,377,867 |
| ANK3 | 10 | rs1050745 | 61,457,255 | rs1551684 | 61,820,209 |
| KCNQ1 | 11 | rs11022827 | 2,414,908 | rs2239897 | 2,848,541 |
| KCNC1 | 11 | rs7949069 | 17,711,203 | rs1236205 | 17,760,287 |
| *Delimiting SNPs for Cell Adhesion and Related Genes* | | | | | |
| RP1-21O18.1 | 1 | rs9663010 | 15,143,609 | rs2235789 | 15,314,645 |
| CTNND1 | 11 | rs558653 | 57,285,706 | rs652908 | 57,360,585 |
| DACT1 | 14 | rs464582 | 58,171,201 | rs160472 | 58,185,201 |
| CDH11 | 16 | rs35148 | 63,536,690 | rs7204464 | 63,731,895 |
| *Delimiting SNPs for Vesicle-Related Genes* | | | | | |
| VAMP4 | 1 | rs10913508 | 169,935,102 | rs7556644 | 169,979,491 |
| SYT14 | 1 | rs9429830 | 208,177,160 | rs11119426 | 208,407,592 |
| BRSK2 | 11 | rs7395835 | 1,365,307 | rs1554857 | 1,441,643 |
| SYT13 | 11 | rs2863172 | 45,217,918 | rs11038382 | 45,269,392 |
| STX2 | 12 | rs2632601 | 129,834,650 | rs7962097 | 129,890,817 |
| RTN1 | 14 | rs17255975 | 59,131,314 | rs7144589 | 59,407,620 |
| UNC13C | 15 | rs11071015 | 52,092,152 | rs9920150 | 52,708,142 |
| SV2B | 15 | rs11630131 | 89,569,404 | rs7169918 | 89,640,060 |
| *Delimiting SNPs for Genes Related to Glutamate Pathways* | | | | | |
| Gcom1 | 15 | rs1908202 | 55,669,589 | rs1808478 | 55,797,051 |
| GRINL1A | 15 | rs1908202 | 55,669,589 | rs1808478 | 55,797,051 |
| GOT2 | 16 | rs2042445 | 57,296,647 | rs4238801 | 57,329,680 |
| *Delimiting SNPs for G-Protein Coupled Receptor Related Genes* | | | | | |
| RHOG | 11 | rs1055640 | 3,803,869 | rs4406820 | 3,819,109 |
| GPR135 | 14 | rs17255731 | 58,964,865 | rs4898989 | 59,005,097 |
| AKAP13 | 15 | rs1533124 | 83,674,688 | rs11637212 | 84,094,101 |
| *Delimiting SNPs for Hormone, Inositol, and Diacylglyceride Related Genes* | | | | | |
| HSD17B12 | 11 | rs12364003 | 43,657,684 | rs11037691 | 43,848,213 |
| IGF1R | 15 | rs35554027 | 97,008,574 | rs702497 | 97,319,104 |
| *Delimiting SNPs for Cytoskeletal, Myosin, Actin and Microtubule Related Genes* | | | | | |
| EVL | 14 | rs1190954 | 99,601,206 | rs35257667 | 99,689,766 |
| KATNAL2 | 18 | rs9304340 | 42,780,580 | rs1434528 | 42,886,321 |
| *Delimiting SNPs for Genes for Carrier Proteins and Transporters* | | | | | |
| SLC6A17 | 1 | rs924181 | 110,481,637 | rs545849 | 110,546,538 |
| SLC16A4 | 1 | rs10857820 | 110,706,448 | rs12127781 | 110,738,080 |
| SLC6A5 | 11 | rs894747 | 20,575,165 | rs1401793 | 20,632,993 |
| SLC17A6 | 11 | rs1155821 | 22,315,296 | rs2593644 | 22,357,697 |
| SLCO3A1 | 15 | rs11858120 | 90,196,267 | rs1060206 | 90,509,554 |
| *Delimiting SNPs for Cell Cycle and Tumor Suppressor/Promoter Related Genes* | | | | | |
| RERE | 1 | rs1055236 | 8,326,680 | rs914994 | 8,839,799 |
| FASLG | 1 | rs763110 | 170,894,121 | rs12135884 | 170,905,123 |
| DEAF1 | 11 | rs936465 | 633,568 | rs6597990 | 687,761 |
| HCCA2 | 11 | rs12786504 | 1,446,780 | rs2334652 | 1,462,030 |
| PTPN5 | 11 | rs873670 | 18,705,395 | rs7932938 | 18,771,871 |
| CHFR | 12 | rs1531822 | 131,925,194 | rs3741494 | 131,974,573 |
| TTC5 | 14 | rs10130942 | 19,826,245 | rs10873395 | 19,845,685 |
| FUSSEL18 | 18 | rs2137289 | 43,006,123 | rs892583 | 43,170,372 |
| SMAD2 | 18 | rs1792666 | 43,617,212 | rs2000709 | 43,713,512 |
| SMAD7 | 18 | rs9944944 | 44,699,493 | rs736839 | 44,782,063 |
| SMAD4 | 18 | rs620898 | 46,763,146 | rs12456284 | 46,863,966 |
| *Delimiting SNPs for Genes Involved in Neuronal Development and Plasticity* | | | | | |
| DNM3 | 1 | rs6701033 | 170,076,599 | rs13932 | 170,678,391 |
| TOLLIP | 11 | rs5744038 | 1,252,012 | rs5743854 | 1,287,830 |
| DUSP8 | 11 | rs6578504 | 1,532,811 | rs10734456 | 1,563,922 |
| NAV2 | 11 | rs890136 | 19,687,211 | rs2246192 | 20,098,415 |
| LRRC4C | 11 | rs11035693 | 40,091,818 | rs10128639 | 40,275,738 |
| RTN4RL2 | 11 | rs2729363 | 56,983,430 | rs2955849 | 57,005,697 |
| DTX4 | 11 | rs10896947 | 58,694,659 | rs544864 | 58,735,516 |
| ULK1 | 12 | rs11246867 | 130,943,970 | rs7978708 | 130,977,857 |
| NDRG2 | 14 | rs1263871 | 20,553,926 | rs1243451 | 20,564,197 |
| JPH4 | 14 | rs12897422 | 23,102,867 | rs222732 | 23,129,120 |
| DAAM1 | 14 | rs17095965 | 58,718,491 | rs4127823 | 58,926,458 |

TABLE A-continued

Delimiting SNPs for Novel SZ Genes (NCBI Genome Build 36.2)

| Gene | Chrom. | SNP 1 | Location (bp) | SNP 2 | Location (bp) |
|---|---|---|---|---|---|
| NEDD4 | 15 | rs4424863 | 53,905,753 | rs1509408 | 54,073,605 |
| RGMA | 15 | rs12438714 | 91,386,979 | rs4114 | 91,443,429 |
| N4BP1 | 16 | rs9937623 | 47,129,091 | rs9936446 | 47,203,308 |
| NDRG4 | 16 | rs7202037 | 57,054,471 | rs2280397 | 57,109,729 |
| CDH8 | 16 | rs4131634 | 60,243,900 | rs9302540 | 60,629,024 |
| BEAN | 16 | rs6499082 | 64,992,072 | rs12445633 | 65,114,761 |
| KIAA0513 | 16 | rs1875246 | 83,617,069 | rs1466864 | 83,691,111 |
| DYM | 18 | rs1288812 | 44,821,479 | rs17725481 | 45,241,155 |
| DCC | 18 | rs17753970 | 48,119,269 | rs2270954 | 49,311,296 |
| BMP7 | 20 | rs6014947 | 55,177,906 | rs2208404 | 55,277,143 |
| TMEPAI | 20 | rs6025689 | 55,656,857 | rs6015068 | 55,734,303 |
| Delimiting SNPs for Calcium/Calmodulin Related Genes | | | | | |
| CAMTA1 | 1 | rs449250 | 6,720,271 | rs228651 | 7,833,686 |
| CACNA1E | 1 | rs541886 | 179,718,012 | rs635118 | 180,037,358 |
| CAMK1G | 1 | rs17014820 | 207,823,042 | rs926387 | 207,854,836 |
| RIMBP2 | 12 | rs1496858 | 129,444,850 | rs7963990 | 129,571,289 |
| Delimiting SNPs for Genes Involved in Hereditary Hearing Loss | | | | | |
| DPH3 | 3 | rs2292614 | 16,276,795 | rs2245708 | 16,281,022 |
| EXOC2 | 6 | rs10900954 | 428,817 | rs13205146 | 638,473 |
| USH1C | 11 | rs4756895 | 17,470,828 | rs2073582 | 17,523,687 |
| OTOG | 11 | rs2073582 | 17,523,687 | rs11024358 | 17,624,137 |
| SERGEF | 11 | rs1236205 | 17,760,287 | rs1133758 | 17,998,369 |
| EML1 | 14 | rs10140193 | 99,328,197 | rs7149272 | 99,487,743 |
| PMP22 | 17 | rs230938 | 15,071,845 | rs179521 | 15,113,946 |
| Delimiting SNPs for Genes Encoding Zn-Finger Proteins | | | | | |
| PRDM2 | 1 | rs2487657 | 13,894,681 | rs979932 | 13,987,558 |
| ZFP91-CNTF | 11 | rs1944055 | 58,099,205 | rs4319530 | 58,156,405 |
| ZNF423 | 16 | rs193907 | 48,080,956 | rs12443775 | 48,418,620 |
| Delimiting SNPs for Brain-expressed Genes (not otherwise specified) | | | | | |
| PER3 | 1 | rs172933 | 7,767,267 | rs707472 | 7,828,595 |
| RABGAP1L | 1 | rs6681627 | 172,393,365 | rs12126129 | 173,194,998 |
| PHACS | 11 | rs178512 | 44,043,887 | rs2285029 | 44,062,444 |
| YPEL4 | 11 | rs1798177 | 57,168,726 | rs1647394 | 57,175,164 |
| KIAA1853 | 12 | rs7979864 | 117,902,236 | rs722307 | 118,094,760 |
| KIAA1545 | 12 | rs10870551 | 131,567,365 | rs7294615 | 131,678,218 |
| TEP1 | 14 | rs1713418 | 19,904,649 | rs1760890 | 19,951,629 |
| WDR25 | 14 | rs2273802 | 99,912,652 | rs10151709 | 100,067,090 |
| BEGAIN | 14 | rs11628965 | 100,071,902 | rs7140556 | 100,106,211 |
| HERC2 | 15 | rs7495174 | 26,017,833 | rs1614575 | 26,236,593 |
| ADAM10 | 15 | rs3764196 | 56,674,302 | rs514049 | 56,829,655 |
| KLHL25 | 15 | rs11637212 | 84,094,101 | rs7181017 | 84,145,916 |
| NETO2 | 16 | rs1551188 | 45,616,796 | rs7184206 | 45,736,527 |
| CBLN1 | 16 | rs3743777 | 47,869,517 | rs9935379 | 47,884,582 |
| KIAA0182 | 16 | rs4240810 | 84,182,628 | rs3815795 | 84,269,606 |
| C16orf74 | 16 | rs11644122 | 84,298,251 | rs301143 | 84,342,400 |
| COX10 | 17 | rs4792434 | 13,912,946 | rs7218697 | 14,074,153 |
| KIAA0427 | 18 | rs1039989 | 44,318,592 | rs752151 | 44,697,296 |

In one aspect, the invention includes methods for obtaining information regarding a subject's risk for developing SZ, i.e., determining the subject's risk of developing SZ. The methods include obtaining a test haplotype associated with schizophrenia as described herein. The methods can also include obtaining a sample comprising genomic DNA (gDNA) from the subject, and determining the identity, absence or presence of a test haplotype associated with SZ as described herein. In some embodiments, the methods include obtaining a test haplotype for the subject comprising at least one test SNP marker that is found within the region delimited by SNP1 and SNP2, inclusive, for a given gene as specified in Table A, or comprising one or more of the exemplary SNP markers for each gene, as specified in the Examples and/or SNP markers in linkage disequilibrium with these markers, wherein the haplotype provides information regarding the subject's risk of developing SZ, SD, or SPD. In some embodiments, the test marker is a marker listed in one or more genes of Table A that is in linkage disequilibrium (defined by correlation, $[r^2] \geq 0.5$) with a marker listed in Table A in Table B as shown in the Examples, wherein the haplotype provides information regarding the subject's risk of developing SZ, e.g., markers lying between the exemplary SNPs for a gene listed in Table A, but not explicitly listed in the Examples.

In some embodiments, the test haplotype includes at least one marker lying between delimiting SNPs (SNP1 and SNP2), inclusive, for a given gene as specified in Table A, e.g., the exemplary delimiting SNPs listed in Table A; other delimiting SNPs can be chosen from other SNPs known in the art, e.g., the exemplary test SNPs described herein. In some embodiments, the test haplotype includes two or more markers from one gene. In some embodiments, the test genotype includes at least two markers, each from a different gene listed in Table A.

In some embodiments, the test haplotype includes at least one marker lying between the SNP1 and SNP2, inclusive, for a given gene as specified in Table A and provides information regarding a subject's risk of developing SZ under a narrower (DSM III/DSM IV) disease definition.

In some embodiments, the methods include obtaining a test haplotype for the subject by determining the genotype of at least one test marker listed in Table B, or a test marker that lies between the delimiting markers listed in Table A and that is in linkage disequilibrium (LD, defined by correlation, $[r^2]≥0.5$) with markers listed in Table B, wherein the test haplotype indicates the subject's risk of developing SZ. In some embodiments, the at least one test marker is in the KIAA0182 gene or the KIAA0427 gene. In some embodiments, the test marker is selected from the group consisting rs736845; rs994060; rs381579; rs217556; rs8095199; or is a test marker in LD with these markers.

In some embodiments, the methods described herein can be used for predicting a human subject's likely response to an antipsychotic medication. The methods include obtaining a test haplotype for the subject by determining the genotype for at least one test marker listed in Table B, or at least one test marker that lies between the delimiting markers in Table A and that is in linkage disequilibrium (LD) (defined by correlation, [r2]≥0.5) with a marker listed in Table B, wherein the test haplotype indicates the subject's likely response, e.g., likelihood of responding positively (i.e., an improvement in one or more symptoms of the disease) or negatively (i.e., with no improvement, or even a worsening, of one or more symptoms of the disease, or with excessive side effects) to an antipsychotic medication. A number of antipsychotic medications are known in the art and can include, for example, olanzapine, risperidone, quetiapine, perphenazine, and ziprasidone.

In some embodiments, the treatment is administration of olanzapine, and the at least one test marker is in a gene selected from the group consisting of C16orf74, synaptic vesicle glycoprotein 2B (SV2B), calmodulin binding transcription activator 1 (CAMTA1), otogelin (OTOG), ras homolog gene family, member G (RHOG). In some embodiments, the test marker is selected from the group consisting of rs230535; rs373835; rs386061; rs449250; rs657739; rs657740; rs755475; rs755475; rs141798; rs110300; rs145172; rs100349; rs108328; rs202348; rs110243; rs11024358; or is a test markers in LD with one of these markers, and the test haplotype indicates the subject's likely response to administration of olanzapine.

In some embodiments, the treatment is administration of risperidone, and the at least one test marker is in a gene selected from the group consisting of neural precursor cell expressed, developmentally down-regulated 4 (NEDD4), cadherin 8, type 2 (CDH8), deformed epidermal autoregulatory factor 1 (DEAF1), hect domain and RLD 2 (HERC2). In some embodiments, the test marker is selected from the group consisting of rs230357; rs230358; rs139713; rs805733; rs930254; rs110754; rs136991; rs197879; rs649880; rs993999; rs496314; rs659799; rs936465; rs659799; rs110743; rs163516; rs223828; rs7495174; or is a test marker that is in linkage disequilibrium with one of these markers. The test haplotype indicates the subject's likely response to administration of risperidone.

In some embodiments, the treatment is administration of quetiapine, and the at least one test marker is in a gene selected from the group consisting of catenin (cadherin-associated protein), delta 1 (CTNND1), reticulon 1(RTN1), A kinase (PRKA) anchor protein 13 (AKAP13), potassium voltage-gated channel, shaker-related subfamily, member 10 (KCNA10), solute carrier family 17 (sodium-dependent inorganic phosphate cotransporter), member 6 (SLC17A6). In some embodiments, the test marker further is selected from the group consisting of: rs207835; rs110265; rs115582; rs207835; rs224671; rs376845; rs708228; rs108966; rs115701; rs215663; rs652908; rs105399; rs206182; rs206182; rs206182; rs338523; rs407525; rs407525; rs484289; rs484307; rs484307; rs716216; rs110735; rs101450; rs127174; rs17310036; or is a test marker that is in linkage disequilibrium with one of these markers. The test haplotype indicates the subject's likely response to administration of quetiapine.

In some embodiments, the treatment is administration of perphenazine, and the at least one test marker is in a gene selected from the group consisting of secretion regulating guanine nucleotide exchange factor (SERGEF) potassium voltage-gated channel, subfamily H (eag-related), member 1 (KCNH1), functional smad suppressing element 18 (FUSSEL18). In some embodiments, the test marker is selected from the group consisting of: rs177022; rs139302; rs1528; rs172424; rs211130; rs211137; rs211146; rs228323; rs105028; rs177854; rs266877; rs723610; rs892583; or is a test marker that is in linkage disequilibrium with one of these markers. The test haplotype indicates the subject's likely response to perphenazine.

In some embodiments, the treatment is administration of ziprasidone, and the at least one test marker is in a gene selected from the group consisting of unc-13 homolog C (*C. elegans*) (UNC13C), cerebellin 1 precurso (CBLN1), checkpoint with forkhead and ring finger domains (CHFR). In some embodiments, the test marker is selected from the group consisting of: rs129109; rs110764; rs993537; rs125945; rs116390; rs802519; rs930218; rs230653; rs4758954; or is a test marker that is in linkage disequilibrium with one of these markers. The test haplotype indicates the subject's likely response to administration of ziprasidone.

In some embodiments, the treatment is administration of an antipsychotic drug, and the at least one test marker is in a gene selected from the group consisting of cadherin 11, type 2, OB-cadherin (osteoblast) (CDH11), deleted in colorectal carcinoma (DCC), Usher syndrome 1C (autosomal recessive, severe) (USH1C). In some embodiments, the test marker is selected from the group consisting of: rs35144; rs35148; rs35186; rs35195; rs35144; rs222908; rs950278; rs143174; rs124574; rs494025; rs750690; rs650823; rs139333; rs152023; rs105557; rs105557; rs207222; rs475689; rs16770, or is a test marker that is in linkage disequilibrium with one of these markers. The test haplotype indicates the subject's likely response to administration of an antipsychotic.

In some embodiments, the test haplotype provides information regarding a subject's risk (or likelihood) of having a particular endophenotype, and/or a higher or lower level (e.g., severity) of the endophenotype, e.g., of one or more specific parameters of the PANSS scale, e.g., one or more symptoms, e.g., hallucinations, paranoia, anxiety, depression, or grandiosity, as well as response or lack of response to drugs and comorbidity for substance and alcohol abuse.

In another aspect, the invention provides methods for predicting the degree of severity of a psychiatric endophenotype in a human subject. The methods include obtaining a test haplotype for the subject by determining the genotype for at least one test marker listed in Table B, or at least one test markers that lies between the delimiting markers listed in Table A and that is in linkage disequilibrium (LD) defined by correlation, $[r^2]≥0.5$) with a marker in Table B, wherein the test haplotype indicates the likely degree of severity of a psychiatric endophenotype in the subject. In some embodiments, the psychiatric endophenotype is a quantitative trait that can be measured using one or more of PANSS Total composite score, PANSS Positive composite score, PANSS Negative composite score, and PANSS General Psychopathology composite score.

In some embodiments, the one or more test markers are from calcium channel, voltage-dependent, R type, alpha 1E subunit (CACNA1E), echinoderm microtubule associated protein like 1 (EML1), katanin p60 subunit A-like 2 (KATNAL2) genes. In some embodiments, the test marker is selected from the group consisting of rs174946; rs199960; rs385609; rs465267; rs704326; rs218709; rs224722; rs257103; rs257604; rs723351; rs930434; rs996138; rs225071; rs111605; rs111605; rs124336; rs657575; rs746698; rs227370; rs2273704; or is a test marker in linkage disequilibrium with one of these markers. The test haplotype indicates the likely degree of severity of a psychiatric endophenotype in the subject.

In some embodiments, the psychiatric endophenotype comprises one or more of: a Positive Symptom selected from the group consisting of P1-delusions, P2-conceptual disorganization, P3-hallucinatory behavior, P4-exitement, P5-grandiosity, P6-suspiciousness, P7-hostility; a Negative Symptom selected from the group consisting of N1-blunted affect, N2-emotional withdrawal, N3-poor rapport, N4-passive/appathetic social withdrawal, N5-difficulty in abstract thinking, N60 lack of spontaneity and flow of conversation, N7-steryotyped thinking; or a general psychopathology symptom selected from the group consisting of G1-somatic concern, G2-anxiety, G3-guilt feelings, G4-tension, G5-mannerisms and posturing, G6-depression, G7-motor retardation, G8-uncooperativeness, G9-unusual thought content, G10-disorentation, G11-poor attention, G12-lack of judgment and insight, G13 disturbance of volition, G14-poor impulse control, G15-preoccupation, and G16-active social avoidance.

In some embodiments, the at least one test marker is from a gene selected from the group consisting of DPH3, KTI11 homolog (DPH3), insulin-like growth factor I receptor (IGF1R), calcium/calmodulin-dependent protein kinase IG (CAMK1G), neuron navigator 2 (NAV2), bone morphogenetic protein 7 (BMP7). In some embodiments, the test marker is selected from the group consisting of rs224572; rs842257; rs859703; rs224570; rs496543; rs112473; rs187961; rs268479; rs108332; rs712564; rs10375; rs601494; rs230198; or is a test marker that is in linkage disequilibrium with one of these markers. The test haplotype indicates the likely severity of a psychiatric endophenotype in the subject.

The methods described herein can include obtaining a haplotype that includes two or more, e.g., two, three, four, five, or six markers.

Additionally, the methods can include determining the presence or absence of other markers known to be associated with SZ, SD, or SPD, e.g., outside of a region identified herein. A number of other such markers are known in the art, e.g., as described herein.

The subject can be a human (e.g., a patient having, or at risk of, SZ). In one embodiment, the subject is a patient having previously diagnosed SZ, SD, or SPD (e.g., a patient suffering from early, intermediate or aggressive SZ, SD, or SPD). In some embodiments, the methods described herein are used to obtain information regarding a subject's risk of developing SZ wherein the disorder is other than catatonic schizophrenia. In some embodiments, the subject is of Caucasian (CA) descent, i.e., has one or more ancestors who are CA.

In one embodiment, a subject to be evaluated by a method described herein is a subject having one or more risk factors associated with SZ, SD, or SPD. For example, the subject may have a relative afflicted with SZ, e.g., one or more of a grandparent, parent, uncle or aunt, sibling, or child who has or had SZ, SD, or SPD; the subject may have a genetically based phenotypic trait associated with risk for SZ, SD, or SPD (e.g., eye tracking dysfunction); deficits in working (short-term) memory; and/or mixed-handedness (the use of different hands for different tasks), particularly in females.

In some embodiments, the subject is a child, fetus, or embryo, and one of the subject's relatives, e.g., a parent or sibling, of the child, fetus, or embryo has SZ, SD, or SPD. In this case, the presence in the child, fetus, or embryo of a haplotype described herein that is shared with the affected parent, but not with the non-affected parent, indicates that the child, fetus, or embryo has an increased risk of developing SZ. In some embodiments, the subject has no overt or clinical signs of SZ, SD, or SPD.

In some embodiments, obtaining a test haplotype includes obtaining a sample comprising DNA from the subject; and determining the identity, presence or absence of at least one test marker that is SNP marker that is found within the region delimited by SNP1 and SNP2, inclusive, for a given as specified in Table A, or comprising one or more of the exemplary SNP markers for each gene, as specified in the Table B and/or SNP markers in linkage disequilibrium with these markers (in the particular population) in the DNA. The sample can be obtained, e.g., from the subject by a health care provider, or provided by the subject without the assistance of a health care provider.

In some embodiments, obtaining a test haplotype includes reviewing a subject's medical history, wherein the medical history includes information regarding the presence or absence of at least one test SNP marker that is found within the region delimited by SNP1 and SNP2, inclusive, for a given gene as specified in Table A, or comprising one or more of the exemplary SNP markers for each gene, as specified in Table B, and/or SNP markers in linkage disequilibrium with these markers, in the subject.

In some embodiments, the methods described herein include obtaining a reference haplotype including a reference marker that corresponds to a test marker, and comparing the test haplotype to the reference haplotype. A reference marker that "corresponds to" a test marker is the same marker. For example, if the test haplotype includes rs10766410 in the OTOG gene, then the reference haplotype should also include rs10766410 for comparison purposes; or if the test haplotype includes rs553042 in the CACNA1E gene, then the reference haplotype should also include rs553042 for comparison purposes. In methods where the haplotype analysis is performed to determine risk of developing SZ, the sharing of a haplotype (e.g., of some or all of the marker alleles) between the test haplotype and a reference haplotype is indicative of whether there is an increased likelihood that the subject will develop SZ. The reference haplotype can be from a relative, e.g., a first or second degree relative, or from an unrelated individual (or population), that has been identified as either having or not having SZ, SD, or SPD. Optionally, a reference haplotype is also obtained from an unaffected person, e.g., an unaffected relative, and lack of sharing of a haplotype of a haplotype between the test haplotype and the reference haplotype indicates that the subject has an increased risk of developing SZ.

In methods where the haplotype analysis is performed to determine risk of having a particular endophenotype or endophenotype severity (e.g., on the PANSS scale), the sharing of a haplotype (e.g., of some or all of the marker alleles) between the test haplotype and a reference haplotype is indicative of whether there is an increased likelihood that the subject will have an elevated (high) or low value for that specific endophenotype. For example, the reference haplotype can be from a relative, e.g., a first or second degree relative, or from an unrelated individual (or population), e.g., a person that has been diagnosed with SZ, and further identified as either having or not having an elevated value for the specific endophenotype. In some embodiments, the presence of the haplotype does not indicate the presence or absence of a specific phenotype, but rather the degree to which the phenotype occurs, e.g., on the PANSS scale; as one example, alleles of the marker rs11030008 can impact the severity of delusions and suspiciousness/persecution not necessarily its presence or absence of these symptoms.

In methods where the haplotype analysis is performed to predict response to a particular treatment, the sharing of a haplotype (e.g., of some or all of the marker alleles) between the test haplotype and a reference haplotype is indicative of how the subject is likely to respond to the treatment. For example, the reference haplotype can be from a relative, e.g., a first or second degree relative, or from an unrelated individual (or population), that has been diagnosed with SZ and further identified as responding positively (i.e., with an improvement in one or more symptoms of the disease) or negatively (i.e., with no improvement, or even a worsening, of one or more symptoms of the disease, or with excessive side effects).

In some embodiments, the methods include administering a treatment to a subject identified as being at increased risk for developing SZ, e.g., a pharmacological treatment as described herein. In some embodiments, the subject has no overt or clinical signs of SZ, SD, or SPD, and the treatment is administrated before any such signs appear.

Information obtained using a method described herein can be used, e.g., to select a subject population for a clinical trial, to stratify a subject population in a clinical trial, and/or to stratify subjects that respond to a treatment from those who do not respond to a treatment, or subjects that have negative side effects from those who do not.

In another aspect, the invention provides methods for selecting a subject for inclusion in a clinical trial, e.g., a trial of a treatment for SZ, SD, or SPD. The methods include obtaining a haplotype for the subject including at least one marker that is found within the region delimited by SNP1 and SNP2, inclusive, for a given gene as specified in Table A, or comprising one or more of the exemplary SNP markers for each gene, as specified in the Table B and/or SNP markers in linkage disequilibrium with these markers e.g. as shown in the Examples; determining whether the haplotype is associated with an increased risk of developing SZ; and including the subject in the trial or excluding the subject from the trial if the haplotype indicates that the subject has altered drug response for patients with SZ, SD, or SPD.

In another aspect, the invention provides methods for selecting a subject for administration of a treatment for schizophrenia (SZ). The methods include obtaining a haplotype for the subject, wherein the haplotype comprises at least one marker that is listed in Table B, or is in linkage disequilibrium with a marker listed in Table B, as exemplified by the Markers listed in Table C; determining whether the haplotype is associated with altered (e.g., positive or negative) treatment response for patients with SZ; and administering the treatment to the subject if the haplotype indicates that the subject has an improved response to the treatment. In another aspect, the invention provides methods for selecting a treatment for administration to a subject. The methods include obtaining a haplotype for the subject, wherein the haplotype comprises at least one marker that is listed in Table B, or is in linkage disequilibrium unit with a marker listed in Table B; determining whether the haplotype is associated with altered (e.g., positive or negative) treatment response for patients with schizophrenia (SZ); and administering the treatment for SZ to the subject if the haplotype indicates that the subject has an improved response to the treatment.

In another aspect, the invention provides methods for evaluating the effect of a haplotype on the outcome of a treatment for schizophrenia (SZ). The methods include obtaining information regarding outcome of the treatment, wherein the information comprises a parameter relating to the treatment of each subject in a population of subjects; obtaining haplotypes for each subject in the population, wherein the haplotype comprises at least one marker that is listed in Table B, or is in linkage disequilibrium with a marker listed in Table B; and correlating the information regarding outcome with the haplotypes; thereby evaluating the effect of the haplotype on the outcome of the treatment.

In some embodiments, the method includes selecting a treatment for administration to a subject who has a selected haplotype, based on the effect of the haplotype on the outcome of the treatment.

In some embodiments, the information regarding outcome of the treatment is from a completed clinical trial, and the analysis is retrospective.

In a further aspect, the invention features methods for detecting the presence of a haplotype associated with susceptibility to SZ (broadly defined as including, in addition to narrowly defined SZ, SD or SPD) in a subject, by analyzing a sample of DNA from the subject.

Additionally, the invention features methods of predicting a test subject's risk of developing SZ. The methods include obtaining a reference haplotype of a reference subject, wherein the reference subject has SZ, SD, or SPD; determining a test haplotype of the test subject in the same region; and comparing the test haplotype to the reference haplotype, wherein the sharing of a haplotype in this region between the test subject and the reference subject is an indication of an increased likelihood that the test subject will develop SZ. In some embodiments, the method further includes comparing the subject's haplotype to a reference subject who does not have SZ, SD, or SPD.

Further, the invention features methods for predicting a test subject's risk of developing SZ. The methods include obtaining a reference haplotype of a reference subject in a region described herein, wherein the reference subject has SZ; obtaining a test haplotype of the test subject in the same region; and comparing the test haplotype to the reference haplotype. The sharing of a haplotype in this region between the test subject and the reference subject is an indication of an increased likelihood that the test subject will develop SZ. In some embodiments, the method also includes comparing the test subject's haplotype to a reference subject who does not have SZ.

Also provided herein are kits for use in detection of haplotypes associated with SZ, including at least one nucleic acid probe that hybridizes to a sequence that includes a polymorphism described herein, or can be used to amplify a sequence that includes a polymorphism described herein.

Also provided are arrays that include a substrate having a plurality of addressable areas, wherein one or more of the addressable areas includes one or more probes that can be used to detect a polymorphism described herein.

In another aspect, the invention provides methods for providing information regarding a subject's risk of developing schizophrenia (SZ). The methods include obtaining a sample from the subject at a first site; transferring the sample to a second site for analysis, wherein the analysis provides data regarding the identity, presence or absence of at least one test marker that is that is found within the region delimited by SNP1 and SNP2, inclusive, for a given gene as specified in Table A, or comprising one or more of the exemplary SNP markers for each gene, as specified in the Examples and/or SNP markers in linkage disequilibrium with these markers; and transferring the data to one or more of a health care provider, the subject, or a healthcare payer. In some embodiments, the first site is a health care provider's place of business, or is not a health care provider's place of business, e.g., the subject's home.

In some embodiments, the data is transferred to a healthcare payer and used to decide whether to reimburse a health care provider.

DEFINITIONS

As defined herein, "Schizophrenia" or "SZ" includes the SZ-spectrum disorders, Schizotypal Personality Disorder (SPD) and Schizoaffective Disorder (SD), as well as Schizophrenia under the narrower, DSM-IV definition (see below).

As used herein, a "haplotype" is one or a set of signature genetic changes (polymorphisms) that are normally grouped closely together on the DNA strand, and are usually inherited as a group; the polymorphisms are also referred to herein as "markers." A "haplotype" as used herein is information regarding the presence or absence of one or more contiguous genetic markers on a given chromosome in a subject. A haplotype can consist of a variety of genetic markers, including indels (insertions or deletions of the DNA at particular locations on the chromosome); single nucleotide polymorphisms (SNPs) in which a particular nucleotide is changed; microsatellites; and minisatellites.

Microsatellites (sometimes referred to as a variable number of tandem repeats or VNTRs) are short segments of DNA that have a repeated sequence, usually about 2 to 5 nucleotides long (e.g., CACACA), that tend to occur in non-coding DNA. Changes in the microsatellites sometimes occur during the genetic recombination of sexual reproduction, increasing or decreasing the number of repeats found at an allele, changing the length of the allele. Microsatellite markers are stable, polymorphic, easily analyzed and occur regularly throughout the genome, making them especially suitable for genetic analysis.

"Linkage disequilibrium" occurs when the observed frequencies of associations of alleles for different polymorphisms in a population do not agree with frequencies predicted by multiplying together the allele frequencies for the individual genetic markers, thus resulting in a specific haplotype in the population.

The term "chromosome" as used herein refers to a gene carrier of a cell that is derived from chromatin and comprises DNA and protein components (e.g., histones). The conventional internationally recognized individual human genome chromosome numbering identification system is employed herein. The size of an individual chromosome can vary from one type to another with a given multi-chromosomal genome and from one genome to another. In the case of the human genome, the entire DNA mass of a given chromosome is usually greater than about 100,000,000 base pairs. For example, the size of the entire human genome is about $3 \times 10^9$ base pairs.

The term "gene" refers to a DNA sequence in a chromosome that codes for a product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "probe" refers to an oligonucleotide. A probe can be single stranded at the time of hybridization to a target. As used herein, probes include primers, i.e., oligonucleotides that can be used to prime a reaction, e.g., a PCR reaction.

The term "label" or "label containing moiety" refers in a moiety capable of detection, such as a radioactive isotope or group containing same, and nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent). A probe described herein can be bound, e.g., chemically bound to label-containing moieties or can be suitable to be so bound. The probe can be directly or indirectly labeled.

The term "direct label probe" (or "directly labeled probe") refers to a nucleic acid probe whose label after hybrid formation with a target is detectable without further reactive processing of hybrid. The term "indirect label probe" (or "indirectly labeled probe") refers to a nucleic acid probe whose label after hybrid formation with a target is further reacted in subsequent processing with one or more reagents to associate therewith one or more moieties that finally result in a detectable entity.

The terms "target," "DNA target," or "DNA target region" refers to a nucleotide sequence that occurs at a specific chromosomal location. Each such sequence or portion is preferably at least partially, single stranded (e.g., denatured) at the time of hybridization. When the target nucleotide sequences are located only in a single region or fraction of a given chromosome, the term "target region" is sometimes used. Targets for hybridization can be derived from specimens which include, but are not limited to, chromosomes or regions of chromosomes in normal, diseased or malignant human cells, either interphase or at any state of meiosis or mitosis, and either extracted or derived from living or postmortem tissues, organs or fluids; germinal cells including sperm and egg cells, or cells from zygotes, fetuses, or embryos, or chorionic or amniotic cells, or cells from any other germinating body; cells grown in vitro, from either long-term or short-term culture, and either normal, immortalized or transformed; inter- or intraspecific hybrids of different types of cells or differentiation states of these cells; individual chromosomes or portions of chromosomes, or translocated, deleted or other damaged chromosomes, isolated by any of a number of means known to those with skill in the art, including libraries of such chromosomes cloned and propagated in prokaryotic or other cloning vectors, or amplified in vitro by means well known to those with skill; or any forensic material, including but not limited to blood, or other samples.

The term "hybrid" refers to the product of a hybridization procedure between a probe and a target.

The term "hybridizing conditions" has general reference to the combinations of conditions that are employable in a given hybridization procedure to produce hybrids, such conditions typically involving controlled temperature, liquid phase, and contact between a probe (or probe composition) and a target. Conveniently and preferably, at least one denaturation step precedes a step wherein a probe or probe composition is contacted with a target. Guidance for performing hybridization reactions can be found in Ausubel et al., *Current Protocols in Molecular Biology*, John Wiley & Sons, N.Y. (2003), 6.3.1-6.3.6. Aqueous and nonaqueous methods are described in that reference and either can be used. Hybridization conditions referred to herein are a 50% formamide, 2×SSC wash for 10 minutes at 45° C. followed by a 2×SSC wash for 10 minutes at 37° C.

Calculations of "identity" between two sequences can be performed as follows. The sequences are aligned for optimal comparison purposes (e.g., gaps can be introduced in one or both of a first and a second nucleic acid sequence for optimal alignment and non-identical sequences can be disregarded for comparison purposes). The length of a sequence aligned for comparison purposes is at least 30%, e.g., at least 40%, 50%, 60%, 70%, 80%, 90% or 100%, of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two nucleotide sequences is determined using the GAP program in the GCG software package, using a Blossum 62 scoring matrix with a gap penalty of 12, a gap extend penalty of 4, and a frameshift gap penalty of 5.

As used herein, the term "substantially identical" is used to refer to a first nucleotide sequence that contains a sufficient number of identical nucleotides to a second nucleotide sequence such that the first and second nucleotide sequences have similar activities. Nucleotide sequences that are substantially identical are at least 80%, e.g., 85%, 90%, 95%, 97% or more, identical.

The term "nonspecific binding DNA" refers to DNA which is complementary to DNA segments of a probe, which DNA occurs in at least one other position in a genome, outside of a selected chromosomal target region within that genome. An example of nonspecific binding DNA comprises a class of DNA repeated segments whose members commonly occur in more than one chromosome or chromosome region. Such common repetitive segments tend to hybridize to a greater extent than other DNA segments that are present in probe composition.

As used herein, the term "stratification" refers to the creation of a distinction between subjects on the basis of a characteristic or characteristics of the subjects. Generally, in the context of clinical trials, the distinction is used to distinguish responses or effects in different sets of patients distinguished according to the stratification parameters. In some embodiments, stratification includes distinction of subject groups based on the presence or absence of particular markers or haplotypes described herein. The stratification can be performed, e.g., in the course of analysis, or can be used in creation of distinct groups or in other ways.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE DRAWINGS

FIG. 1A-C is a list of exemplary genes useful in the methods described herein, with the sequence identifiers from the GenBank database for their genomic sequences.

DETAILED DESCRIPTION

The present inventors have used bioinformatics and genetic linkages for related neuropsychiatric endophenotypes and DSM disease definitions to define genes in common cellular pathways across various chromosomes as high priority targets for TDT and Case/Control analysis. Resources of the International HapMap project (hapmap.org) were used to define SNPs in these loci, whose pattern of transmission in families and disease association in the population captures extant genetic variation (including important coding variation if present) contributing to genetic susceptibility to SZ-spectrum disorders.

The invention includes methods for assessing genetic risk, aiding in diagnosis, and/or stratifying patient populations in order to select optimal treatments based on evaluation of single nucleotide polymorphisms (SNPs) for a number of bioinformatically identified genes on chromosomes 1, 3, 6, 10, 11, 12, 13, 14, 15, 15, 17, 18, 19, and/or 20 relating to SZ-spectrum disorders including narrowly defined schizophrenia, schizotypal personality disorder (SPD) and schizoaffective disorder (SD) (collectively referred to herein as "SZ"). Specific SNPs delimiting each gene (delimiting SNPs) are given along with exemplary SNPs can be used to capture significant haplotype variation in these genes. Important variants can be verified via TDT using families with multiple affected individuals (such as those collected CCGS) and by Case/Control comparisons using the SNP markers presented herein. Using SNP markers lying between the delimiting SNPs, inclusive, and identical to or in linkage disequilibrium with the exemplary SNPs, one can determine the haplotypes in these genes relating to genetic risk of developing SZ-spectrum disorders via family-based association analyses. These haplotypes can then be used to determine risk of developing these disorders by Case/Control studies. The allelic and genotypic variants thus identified can be used for assessing genetic risk, to aid in diagnosis, and/or to stratify patient population in order to select optimal treatments (atypical antipsychotic, typical antipsychotic, and/or psychosocial intervention) for patients.

Methods of Evaluating Susceptibility to SZ, Pharmacological Response, and Psychiatric Endophenotypes Described herein are a variety of methods for the determination of a subject's risk of developing SZ (which can also be considered susceptibility to SZ) and related clinical phenotypes, likelihood or risk of having an specific endophenotype or severity of an endophenotype, and for predicting a subject's response to a treatment for SZ.

"Susceptibility" to SZ does not necessarily mean that the subject will develop SZ, but rather that the subject is, in a statistical sense, more likely to develop SZ than an average member of the population, i.e., has an increased risk of developing SZ. As used herein, susceptibility to SZ exists if the subject has a haplotype associated with an increased risk of SZ as described herein. Ascertaining whether the subject has such a haplotype is included in the concept of diagnosing susceptibility to SZ as used herein. Similarly, susceptibility to displaying a particular clinical phenotype does not mean that the subject will have the phenotype, but rather that the subject is, in a statistical sense, more likely to display the phenotype. Thus, the methods described herein can include obtaining a haplotype associated with an increased risk of having a specific clinical phenotype as described herein for the subject. Furthermore, a prediction of response may not provide 100% certainty, but simply a statistical likelihood that the subject will respond in a particular way to a particular treatment. Such determinations are useful, for example, for purposes of diagnosis, treatment selection, and genetic counseling.

As used herein, "obtaining a haplotype" includes obtaining information regarding the identity, presence or absence of one or more genetic markers in a subject. Obtaining a haplotype can, but need not, include obtaining a sample comprising DNA from a subject, and/or assessing the identity, presence or absence of one or more genetic markers in the sample. The individual or organization who obtains the haplotype need not actually carry out the physical analysis of a sample from a subject; the haplotype can include information obtained by analysis of the sample by a third party. Thus the methods can include steps that occur at more than one site. For example, a sample can be obtained from a subject at a first site, such as at a health care provider, or at the subject's home in the case of a self-testing kit. The sample can be analyzed at the same or a second site, e.g., at a laboratory or other testing facility. Obtaining a haplotype can also include or consist of reviewing a subject's medical history, where the medical history includes information regarding the identity, presence or absence of one or more genetic markers in the subject, e.g., results of a genetic test.

As described herein, haplotypes associated with SZ include specific alleles for markers in Tables B and C, and makers in linkage disequilibrium with these, as exemplified by the Case/Control results in Table 1.

As one example, haplotypes associated with pharmacological response include one or more markers in Tables B and C and/or markers in linkage disequilibrium with these markers as exemplified by the Examples in Tables 2, 3, 4, 5, 6, 7, 8, 9, 10, 11, 12 and 13. Haplotypes associated with response to olanzapine can include one or more markers listed in Tables 2 and 3 and/or markers in linkage disequilibrium with these markers. Haplotypes associated with response to risperidone can include one or more markers listed in Tables 4 and 5 and/or markers linkage disequilibrium with these markers. Haplotypes associated with response to quetiapine can include one or more markers listed in Tables 6 and 7 and/or markers linkage disequilibrium with these markers. Haplotypes associated with response to perphenazine can include one or more markers listed in Tables 8 and 9 and/or markers linkage disequilibrium with these markers. Haplotypes associated with response to ziprasidone can include one or more markers listed in Tables 10 and 11 and/or markers linkage disequilibrium with these markers. Haplotypes associated with response to antipsychotic medications, as a group, can include one or more markers listed in Tables 12 and 13 and/or markers linkage disequilibrium with these markers. In some embodiments, the haplotype includes one or more of the markers listed in Tables 2, 3, 4, 5, 6, 7, 8, 9, 10, 11, 12 and 13.

As another example, haplotypes associated with specific psychiatric endophenotypes include one or more markers in Tables B and C and/or markers in linkage disequilibrium with these markers as exemplified by the Examples in Tables 14 and 15 and/or markers linkage disequilibrium with these markers. Haplotypes associated with altered scores for the main subscales of the Positive and Negative Syndrome Scale (PANSS) can include one or more markers listed in Table 14. Haplotypes associated with altered scores for specific subscales of the PANSS can include one or more markers listed in Table 15 and/or markers in linkage disequilibrium with these markers. In some embodiments, the haplotype includes one or more of the markers listed in Tables 14 and 15.

In some embodiments, to detect the presence of a haplotype described herein, a biological sample that includes nucleated cells (such as blood, a cheek swab or mouthwash) is prepared and analyzed for the presence or absence of preselected markers. Such diagnoses may be performed by diagnostic laboratories, or, alternatively, diagnostic kits can be manufactured and sold to health care providers or to private individuals for self-diagnosis. Diagnostic or prognostic tests can be performed as described herein or using well known techniques, such as described in U.S. Pat. No. 5,800,998.

Results of these tests, and optionally interpretive information, can be returned to the subject, the health care provider or to a third party payor. The results can be used in a number of ways. The information can be, e.g., communicated to the tested subject, e.g., with a prognosis and optionally interpretive materials that help the subject understand the test results and prognosis. The information can be used, e.g., by a health care provider, to determine whether to administer a specific drug, or whether a subject should be assigned to a specific category, e.g., a category associated with a specific disease endophenotype, or with drug response or non-response. The information can be used, e.g., by a third party payor such as a healthcare payer (e.g., insurance company or HMO) or other agency, to determine whether or not to reimburse a health care provider for services to the subject, or whether to approve the provision of services to the subject. For example, the healthcare payer may decide to reimburse a health care provider for treatments for SZ, SPD, or SD if the subject has an increased risk of developing SZ. As another example, a drug or treatment may be indicated for individuals with a certain haplotype, and the insurance company would only reimburse the health care provider (or the insured individual) for prescription or purchase of the drug if the insured individual has that haplotype. The presence or absence of the haplotype in a patient may be ascertained by using any of the methods described herein.

Information obtained from the methods described herein can also be used to select or stratify subjects for a clinical trial. For example, the presence of a selected haplotype described herein can be used to select a subject for a trial. The information can optionally be correlated with clinical information about the subject, e.g., diagnostic, therapeutic, or endophenotypic information.

Haplotypes Associated with SZ, Pharmacological Response, and Psychiatric Endophenotypes The methods described herein include the analysis of genotypic information for exemplary SNPs described herein as being associated with increased risk of developing SZ, pharmacological response, and having specific psychiatric endophenotypes. The methods can also (or alternatively) include the evaluation of SNPs that are in linkage disequilibrium with the exemplary SNPs (as one of skill in the art will appreciate, those SNPs that are in linkage disequilibrium will provide essentially the same information as the exemplary SNPs). In some embodiments, the methods include the use of SNPs that are in linkage disequilibrium and are within a specified region of the gene. Table B includes exemplary delimiting SNPs and exemplary test SNPs that can be used in capturing significant haplotype variation in these genes. Although exemplary delimiting SNPs are provided, in some embodiments the region can be delimited by one of the other SNPs listed herein, e.g., an exemplary test SNP that is in LD with the primary SNP. In some embodiments, the specific region of the gene is between and excluding the delimiting SNPs; in some embodiments, the specific region is between and including the delimiting SNPs.

TABLE B

Delimiting and Exemplary SNPs for Novel SZ Genes

| Gene | CHR | Delimiting SNPs | Exemplary SNPS |
|---|---|---|---|
| Potassium Channel and Related Genes | | | |
| KCNC4 | 1 | rs1359149 to rs11578913 | rs615204, rs34171476, rs35167146 |
| KCNA10 | 1 | rs1281177 to rs17025957 | rs1281175, rs34970857, rs1281174, rs3768456 |
| KCND3 | 1 | rs197422 to rs10745323 | rs12033257, rs35027371, rs3738298, rs11102342, rs4838924, rs4839183, rs17215423, rs2289723, rs3820673, rs1936061 |
| KCNH1 | 1 | rs12126648 to rs1538287 | rs3135473, rs1135317, rs1770213, rs1770220, rs11119627, rs1501569, rs1393026, rs11119658, rs4620600, rs4578265, rs867848, |
| ANK3 | 10 | rs1050745 to rs1551684 | rs1049862, rs7911953, rs2393607, rs12261793, rs10733757, rs7907721, rs4568956, rs2241540, rs2393596, rs11596260, rs3750800, rs10218875, rs4948254, rs6479694 |
| KCNQ1 | 11 | rs11022827 to rs2239897 | rs2283155, rs6578273, rs34320941, rs4930127, rs2283174, rs45478697, rs45606931, rs45497392, rs231348, rs17215465, rs760419, rs231899, rs63934, rs45603932, rs1057128, rs81205, rs45594640, rs34516117, rs1800172, rs34150427, rs11601907, rs8234 |
| KCNC1 | 11 | rs7949069 to rs1236205 | rs2299637, rs4757587, rs757514, rs10766434, rs7942518 |
| Cell Adhesion and Related Genes | | | |
| RP1-21O18.1 | 1 | rs9663010 to rs2235789 | rs7546786, rs6663699, rs1316257, rs938249, rs6674129, rs2073091, rs2076563, rs12057431, rs4661572 |
| CTNND1 | 11 | rs558653 to rs652908 | rs2156638, rs11570176, rs10896644, rs11570194, rs483030, rs11570199, rs612688, rs11570222, rs708228 |
| DACT1 | 14 | rs464582 to rs160472 | rs167481, rs150722, rs167481, rs863091,, rs34015825, rs17832998, rs17094821, rs698025, rs11541 |
| CDH11 | 16 | rs35148 to rs7204464 | rs35147, rs35145978, rs35144, rs35229, rs35213, rs4424934, rs35195, rs35186, rs1520233, rs7188625 |
| Vesicle Related Genes | | | |
| VAMP4 | 1 | rs10913508 to rs7556644 | rs15655, rs15655, rs10913530, rs2073484, rs66672082, rs12096984 |
| SYT14 | 1 | rs9429830 to rs11119426 | rs227221, rs4844923, rs2205989, rs11119392, rs227227, rs2307890, rs11119415, rs17188183, rs4609425 |
| BRSK2 | 11 | rs7395835 to rs1554857 | rs10833086, rs7932863, rs9651643, rs34893167, rs1881504, rs11029039, rs3829225, rs1574122 |
| SYT13 | 11 | rs2863172 to rs11038382 | rs4992029, rs8929, rs2863174, rs4755941, rs7103871, rs12362429, rs2863182 |
| STX2 | 12 | rs2632601 to rs7962097 | rs6486602, rs1236, rs4759517, rs2277336, rs6486600, rs4759794, rs7301926, rs6486602, rs10848210, rs10848210 |
| RTN1 | 14 | rs17255975 to rs7144589 | rs7161094, rs1950785, rs4898998, rs12717467, rs34431036, rs35707243, rs35645652, rs35645652, rs35864480, rs10145080, rs17310036 |
| UNC13C | 15 | rs11071015 to rs9920150 | rs17731958, rs2115827, rs2163195, rs12594549, rs1897069, rs12910912, rs12910912, rs11856476, rs4776216, rs7183952, rs12917364, rs12914912, rs8035356, rs1158075, rs1849210, rs12913366, rs489526, rs8025195, rs16974691, rs9302181, rs11639005, rs1520411, rs9920139 |
| SV2B | 15 | rs11630131 to rs7169918 | rs2073967, rs35575298, rs8027498, rs1075840, rs16945475, rs2301665, |

TABLE B-continued

Delimiting and Exemplary SNPs for Novel SZ Genes

| Gene | CHR | Delimiting SNPs | Exemplary SNPS |
|------|-----|-----------------|----------------|
|      |     |                 | rs3743444, rs1117388, rs1117388, rs16945529 |

Genes Related to Glutamate Pathways

| Gene | CHR | Delimiting SNPs | Exemplary SNPS |
|------|-----|-----------------|----------------|
| Gcom1 | 15 | rs1908202 to rs1808478 | rs4774275, rs1908206, rs2470357, rs2069133,, rs16977629, rs16977631, rs986868, rs2733617, rs16977644, rs2733619, rs2470361, rs11854917 |
| GRINL1A | 15 | rs1908202 to rs1808478 | rs4774275, rs1908206, rs2470357, rs2069133,, rs16977629, rs16977631, rs986868, rs2733617, rs16977644, rs2733619, rs2470361, rs11854917 |
| GOT2 | 16 | rs2042445 to rs4238801 | rs30839, rs6993, rs30842, rs11076256, rs257636, rs257620 |

G-Protein-Coupled Receptor Genes

| Gene | CHR | Delimiting SNPs | Exemplary SNPS |
|------|-----|-----------------|----------------|
| RHOG | 11 | rs1055640 to rs4406820 | rs1451722, rs17173879, rs1049388, rs1451719, rs11030008 |
| GPR135 | 14 | rs17255731 to rs4898989 | rs1612112, rs1253181, rs10138199, rs9323348, rs1752427, rs1752428, rs10136708 |
| AKAP13 | 15 | rs1533124 to rs11637212 | rs16977252, rs8024200, rs7180213, rs6497206, rs2291049, rs2061821, U171, rs2061822, rs34434221, rs2061824, rs745191, rs7177107, rs7177107, rs4075256, rs4075254, rs4843074, rs4843075, rs7162168, rs4842895, rs35079107, rs338523, rs338556, rs11073502, rs11073502, rs2241268, rs2241268, rs1053992 |

Delimiting SNPs for Hormone, Inositol, and Diacylglyceride Related Genes

| Gene | CHR | Delimiting SNPs | Exemplary SNPS |
|------|-----|-----------------|----------------|
| HSD17B12 | 11 | rs12364003 to rs11037691 | rs4573669, rs10838160, rs4755744, rs7129046, rs3802891, rs11555762, rs1061810 |
| TMEM55B | 14 | rs1130409 to rs1760941 | rs17112002, rs1760943, rs35567022 |
| IGF1R | 15 | rs35554027 to rs702497 | rs8028620, rs7170035, rs7174918, rs8038015, rs4966020, rs4965436, rs8030950, rs1879613, rs11247380, rs45445894, rs34516635, rs33958176,, rs33958176, rs45553041, rs2684808, rs3743262, rs1546713, rs2229765, rs2684792, rs17847203, rs3833015 |

Cytoskeletal, Myosin, Actin and Microtubulal Related Genes

| Gene | CHR | Delimiting SNPs | Exemplary SNPS |
|------|-----|-----------------|----------------|
| EVL | 14 | rs1190954 to rs35257667 | rs748354, rs1190956, rs1190974, rs3206354, rs726514, rs941897, rs34073270, rs4905933 |
| KATNAL2 | 18 | rs9304340 to rs1434528 | rs2576042, rs2187092, rs2571030, rs2247221, rs7233515, rs9961383, rs2289130 |

Genes for Carrier Proteins and Transporters

| Gene | CHR | Delimiting SNPs | Exemplary SNPS |
|------|-----|-----------------|----------------|
| SLC6A17 | 1 | rs924181 to rs545849 | rs877068, rs1010892, rs6689641, rs534276, rs534276, rs6685009, rs12133992 |
| SLC16A4 | 1 | rs10857820 to rs12127781 | rs2946571, rs11120, rs6673423, rs2271885, rs35157487, rs3738750, rs1334882, rs884684 |
| SLC6A5 | 11 | rs894747 to rs1401793 | rs2001982, rs2241940, rs1443547, rs7109418, rs1443548, rs34243519, rs894750, rs4923386, rs16906566, rs11827415, rs3740870, rs1805091, rs7944684, rs2298826, rs2276433, rs16906628, rs1401793 |
| SLC17A6 | 11 | rs1155821 to rs2593644 | rs2246710, rs11026523, rs2078352, rs11026532, rs1900586, rs764021, rs7117340, rs1979072, rs1979073 |
| SLCO3A1 | 15 | rs11858120 to rs1060206 | rs12907294, rs4294800, rs2176452, rs12912997, rs1878556, rs2286355, rs1517618, rs6496893, rs2074887, rs2302085, rs8174 |

TABLE B-continued

Delimiting and Exemplary SNPs for Novel SZ Genes

| Gene | CHR | Delimiting SNPs | Exemplary SNPS |
|---|---|---|---|
| Cell Cycle and Tumor Suppressor/Promoter Related Genes ||||
| RERE | 1 | rs1055236 to rs914994 | rs8627, rs1058766, rs13596, rs3753275, rs7530745, rs12136689, rs7532459, rs7554486, rs6698830 |
| FASLG | 1 | rs763110 to rs12135884 | rs929087, rs6700734, rs10458360, rs35178418 |
| DEAF1 | 11 | rs936465 to rs6597990 | rs11822917, rs34114147, rs7109335, rs10902188, rs6597996, rs34094369, rs7935419, rs7121608, rs4963145 |
| HCCA2 | 11 | rs12786504 to rs2334652 | rs7945160, rs9440, rs10219175, rs7396514, rs7945160, rs10742185 |
| PTPN5 | 11 | rs873670 to rs7932938 | rs7946105, rs1550871, rs1550870, rs6483524, rs4757707, rs10766500, rs4272766, rs4274187, rs4345940 |
| CHFR | 12 | rs1531822 to rs3741494 | rs3741489, rs3741492, rs2306536, rs2306537, rs9634239, rs2306541, rs4758954, rs35206714, rs34220055, rs2291253, rs11147144 |
| TTC5 | 14 | rs10130942 to rs10873395 | rs10147548, rs3737220, rs1953552, rs3742945, rs34675160, rs2318864 |
| FUSSEL18 | 18 | rs2137289 to rs892583 | rs7236105, rs17785419, rs10502880, rs2668771 |
| SMAD2 | 18 | rs1792666 to rs2000709 | rs7228393, rs1792682, rs17340985, rs1787176, rs1942158, rs12457664 |
| SMAD7 | 18 | rs9944944 to rs736839 | rs11874392, rs8088297, rs34151545, rs11874392, rs1873190, rs3736242 |
| SMAD4 | 18 | rs620898 to rs12456284 | rs3764465, rs12958604, rs2276163, rs12458752, rs2298617 |
| Genes Involved in Neuronal Development and Plasticity ||||
| DNM3 | 1 | rs6701033 to rs13932 | rs965051, rs2206543, rs7554526, rs2093184, rs3736790, rs10489730, rs3736791, rs3736791, rs4576686, rs4075021, rs4382763, rs34870740, rs9425287, rs2301454, rs10752946, rs7528296 |
| TOLLIP | 11 | rs5744038 to rs5743854 | rs3750920, rs3168046, rs35365323, rs5744015, rs5743899 |
| DUSP8 | 11 | rs6578504 to rs10734456 | rs3740620, rs2008493, rs7934037, rs3740620, rs3740620, rs902224, rs902225 |
| NAV2 | 11 | rs890136 to rs2246192 | rs2278132, rs2042600, rs10766590, rs7119267, rs6483617, rs16937196, rs2585788, rs11025310, rs7935182, rs16937251, rs1372989, rs10833202, rs11025335, rs12284679, rs2707084, rs6483629, rs3802799, rs3802800, rs7125647, rs1442710, rs1867114, rs2028570, rs2289566, rs35891966, rs3802803 |
| LRRC4C | 11 | rs11035693 to rs10128639 | rs998447, rs2953310, rs1551833, rs6485187, rs10837367, rs998447, rs3802787 |
| RTN4RL2 | 11 | rs2729363 to rs2955849 | rs2511986, rs3851117 |
| DTX4 | 11 | rs10896947 to rs544864 | rs6591507, rs6591507, rs656163, rs2211912, rs621162, rs1048444, rs3847, rs5029315 |
| ULK1 | 12 | rs11246867 to rs7978708 | rs3088051, rs9652059, rs11616018, rs12303764, rs11609348, rs3088051, rs3088051 |
| NDRG2 | 14 | rs1263871 to rs1243451 | rs10196, rs1243444, rs1243446, rs1243446, rs1243450, rs10138807 |
| JPH4 | 14 | rs12897422 to rs222732 | rs11844366, rs10149510, rs10149510, rs10150089 |
| DAAM1 | 14 | rs17095965 to rs4127823 | rs17095965, rs17833769, rs1252989, rs1268579, rs4901909, rs1253005, rs4898983, rs10143918, rs12147707, rs8022614, rs941884, rs1958180, rs941886, rs11626926, rs10083442 |
| NEDD4 | 15 | rs4424863 to rs1509408 | rs3088077, rs17238461, rs8028559, rs34478706, rs12232351, rs2303579, rs2303580, rs1912402, rs16976618, rs2271289, rs1553739, rs11632974 |
| RGMA | 15 | rs12438714 to rs4114 | rs2272453, rs13167, rs1997382, rs2091635, rs6497019 |

TABLE B-continued

Delimiting and Exemplary SNPs for Novel SZ Genes

| Gene | CHR | Delimiting SNPs | Exemplary SNPS |
|---|---|---|---|
| N4BP1 | 16 | rs9937623 to rs9936446 | rs3826176, rs1224, rs1039342, rs3826176, rs1120276, rs2354580 |
| NDRG4 | 16 | rs7202037 to rs2280397 | rs13333449, rs2042405, rs2271948, rs2271948, rs42945, rs1058132 |
| CDH8 | 16 | rs4131634 to rs9302540 | rs16963768, rs16963771, rs4636897, rs9922048, rs11862141, rs6498807, rs9939991, rs1369918, rs1978796, rs11075445, rs1397131, rs8057338 |
| BEAN | 16 | rs6499082 to rs12445633 | rs11644279, rs34695237, rs4247350 |
| KIAA0513 | 16 | rs1875246 to rs1466864 | rs7499978, rs3803637, rs4783121, rs12597135, rs12446708, rs3794684, rs3751756 |
| DYM | 18 | rs1288812 to rs17725481 | rs833503, rs357894, rs8096141, rs8092003, rs2276200, rs523373, rs498929, rs35435872, rs10775493, rs1943675 |
| DCC | 18 | rs17753970 to rs2270954 | 49311296, rs11875475, rs1145245, rs1465943, rs6508145, rs8089980, rs13381333, rs1893572, rs1431748, rs2229080, rs950278, rs8096519, rs7506904, rs12457407, rs4940251, rs8097413, rs2278339, rs1393331, rs984274, rs984274, rs6508235 |
| BMP7 | 20 | rs6014947 to rs2208404 | rs162316, rs10375, rs3787381, rs230198, rs193044, rs6025469 |
| TMEPAI | 20 | rs6025689 to rs6015068 | rs6025698, rs427278, rs13043471, rs4811905 |

Calcium/Calmodulin Related Genes

| Gene | CHR | Delimiting SNPs | Exemplary SNPS |
|---|---|---|---|
| CAMTA1 | 1 | rs449250 to rs228651 | rs10864639, rs12044121, rs6688732, rs6577393, rs7554752, rs6577401, rs12070592, rs2067995, rs845197, rs1193219, rs1011124, rs6696544, rs12751990, rs3737907, rs3737906, rs4908473, rs1417986, rs2071986, rs707455 |
| CACNA1E | 1 | rs541886 to rs635118 | rs553042, rs17494681, rs506947, rs3856090, rs199960, rs3766980, rs35606457, rs35737760, rs34488539, rs4652678, rs199930, rs704326, rs638132 |
| CAMK1G | 1 | rs17014820 to rs926387 | rs2356933, rs6690557, rs9430004, rs35618105, rs11119314, rs11119315, rs2272879, rs2206107, rs4140599, rs2076230 |
| RIMBP2 | 12 | rs1496858 to rs7963990 | rs10848094, rs756186, rs749093, rs11060869, rs7303240, rs2277356, rs2292663, rs2292664, rs7952756, rs2277361, rs871568, rs4237817, rs4759708 |

Genes Involved in Hereditary Hearing Loss

| Gene | CHR | Delimiting SNPs | Exemplary SNPS |
|---|---|---|---|
| DPH3 | 3 | rs2292614 to rs2245708 | rs859703, rs842257, rs2245721, rs2245708 |
| EXOC2 | 6 | rs10900954 to rs13205146 | rs11242914, rs12952, rs4072107, rs1473909, rs2493037, rs2064302, rs2277095, rs2493049, rs2294660, rs2294664, rs998777, rs35600069, rs17756886, rs1747599, rs2039713 |
| USH1C | 11 | rs4756895 to rs2073582 | rs2237965, rs1055577, rs1055574, rs2072225, rs1064074, rs34077456, rs10832796, rs16770, rs10766408, rs2240487, rs35336155, rs2041027, rs2237957 |
| OTOG | 11 | rs2073582 to rs11024358 | rs10766410, rs11823045, rs7130190, rs11024323, rs7112749, rs7106548, rs4757548, rs2355466, rs11024333, rs7936324, rs7936354, rs11024335, rs2041028, rs1003490, rs7111528, rs11024350, rs12422210, rs10832824, rs2023483, rs11024357 |
| SERGEF | 11 | rs1236205 to rs1133758 | rs10788, rs1528, rs4757589, rs2237930, rs211146, rs2283233, rs211130, rs172424, rs211137, rs34960078, rs2237908 |

TABLE B-continued

Delimiting and Exemplary SNPs for Novel SZ Genes

| Gene | CHR | Delimiting SNPs | Exemplary SNPS |
|---|---|---|---|
| EML1 | 14 | rs10140193 to rs7149272 | rs10144785, rs7143905, rs12433613, rs11160553, rs6575751, rs746698, rs7144394, rs2273707, rs34198557, rs2250718, rs2273704, rs11160563 |
| PMP22 | 17 | rs230938 to rs179521 | rs231018, rs13422, rs7215851, rs231021 |

Genes Encoding Zinc-Finger Proteins

| Gene | CHR | Delimiting SNPs | Exemplary SNPS |
|---|---|---|---|
| PRDM2 | 1 | rs2487657 to rs979932 | rs1203682, rs1203677, rs2076324, rs17350795, rs1203648 |
| ZFP91-CNTF | 11 | rs1944055 to rs4319530 | rs1938596, rs948562, rs7945889, rs8373, rs1938596, rs11229545 |
| ZNF423 | 16 | rs193907 to rs12443775 | rs729805, rs1344529, rs2287314, rs12597210, rs16947716, rs34611339, rs34214571, rs34214571, rs12924119, rs2292155, rs10852603, rs8060387 |

Brain-Expressed Genes Not Otherwise Specified

| Gene | CHR | Delimiting SNPs | Exemplary SNPS |
|---|---|---|---|
| PER3 | 1 | rs172933 to rs707472 | rs2797685, rs707463, rs707465, rs35426314, rs228669, rs17031601, rs10462020, rs35604043, rs35687686, rs35899625, rs228697, rs2640909, rs10462021 |
| RABGAP1L | 1 | rs6681627 to rs12126129 | rs6425302, rs6425305, rs16847624 |
| PHACS | 11 | rs178512 to rs2285029 | rs16937817, rs2074038, rs33952257, rs2018795, rs178521, rs35514614, rs2074043, rs7950395, rs178529, rs3107275 |
| YPEL4 | 11 | rs1798177 to rs1647394 | rs7947357, rs890036, rs12793139, rs7947357, rs12294735 |
| KIAA1853 | 12 | rs7979864 to rs722307 | rs1568923, rs6490226, rs1405049, rs4766926, rs7134748, rs7969288, rs10849629, rs12422371, rs7297606, rs7136574, rs2723880, rs2723882, rs2555269, rs1541764 |
| KIAA1545 | 12 | rs10870551 to rs7294615 | rs36098511, rs7137911, rs2323991, rs4883568, rs4883556, rs3751315, rs10870472, rs4883513, rs11208 |
| TEP1 | 14 | rs1713418 to rs1760890 | rs2104978, rs938886, rs1713449, rs34811735, rs35929175, rs35165628, rs7150689, rs34895824, rs2297615, rs35517499, rs938887, rs34401320, rs1713456, rs1713457, rs2229100, rs1760904, rs2228041, rs1713458, rs1760903, rs34179031, rs17111188, rs2228035, rs34770935, rs1760898, rs1760897 |
| WDR25 | 14 | rs2273802 to rs10151709 | , rs2273801,,, rs34007610, rs34331240, rs2273800, rs3742387, rs941924, rs4905966, rs10873518, rs4905969, rs4905969 |
| BEGAIN | 14 | rs11628965 to rs7140556 | rs11845025, rs12893951, rs35286207, rs4073549, rs4074037, rs6575793 |
| HERC2 | 15 | rs7495174 to rs1614575 | rs1129038, rs11074322, rs11636232, rs1133496, rs1133496, rs4073541, rs2238289, rs3940272, rs11631797, rs916977, rs1635168, rs1635163 |
| ADAM10 | 15 | rs3764196 to rs514049 | rs6494032, rs12592750, rs7166076, rs8039791, rs12899638, rs7165402, rs12912286, rs4775086, rs2054096, rs653765 |
| KLHL25 | 15 | rs11637212 to rs7181017 | rs2614676, rs2554, rs3743335, rs2430838, rs36031133, rs35582838, rs11073537, rs2002909, rs2946365 |
| NETO2 | 16 | rs1551188 to rs7184206 | rs16952126, rs16952126, rs9923731, rs11859615, rs3095622 |
| CBLN1 | 16 | rs3743777 to rs9935379 | rs11076478, rs1510977, rs1437105 |
| KIAA0182 | 16 | rs4240810 to rs3815795 | rs35869664, rs3815794, rs736845, rs2303203, rs9940601, rs1049868 |
| C16orf74 | 16 | rs11644122 to rs301143 | rs373835, rs2305357, rs386061, rs408988 |
| COX10 | 17 | rs4792434 to rs7218697 | rs2302107, rs16948978, rs34342426, rs16948986, rs8077302, rs2159132, rs8070339, rs2230354, rs11078233 |

TABLE B-continued

Delimiting and Exemplary SNPs for Novel SZ Genes

| Gene | CHR | Delimiting SNPs | Exemplary SNPS |
|---|---|---|---|
| KIAA0427 | 18 | rs1039989 to rs752151 | rs2175565, rs7229395, rs2306514, rs2277712, rs8094634, rs10853569, rs8095199, rs1038308, rs4939813, rs3764481, rs937021 |

Additionally, a number of exemplary SNPs in linkage disequilibrium with the SNPs in Table B were evaluated for impact on SZ risk, pharmacological response, and specific psychiatric phenotypes (endophenotypes). These exemplary SNPs in linkage disequilibrium with those in Table B are listed in Table C.

TABLE C

Exemplary SNPs in Linkage Disequilibrium with Table B SNPs

| Gene | SNPs in linkage disequilibrium with those in Table B |
|---|---|
| ADAM10 | rs7164844, rs7161889, rs605928 |
| AKAP13 | rs12440599, rs2291048, rs2241268, rs16949988, rs2430838, rs870689, rs2241269, rs2241266, rs8025135, rs10520596, rs16941653, rs17623915, rs745191 |
| ANK3 | rs11596260, rs10761451, rs10761446, rs1551683, rs2393602, rs1078534, rs1050745 |
| BEAN | rs11075635, rs1063438 |
| BMP7 | rs6123669, rs6127980, rs162313, rs230191, rs230198 |
| BRSK2 | rs1108991, rs1554857, rs7396009 |
| C16orf74 | rs442069, rs394623, rs386061, rs11644122 |
| CACNA1E | rs17494681, rs16857457, rs678643, rs553042, rs7513540, rs3856093, rs10797729, rs7554158, rs1953690, rs7534913, rs704331, rs17693196, rs546191 |
| CAMK1G | rs10489339, rs7516885, rs9429821, rs713075, rs7512091, rs6683256 |
| CAMTA1 | rs1616122, rs277675, rs17030082, rs845265, rs2097518, rs9919223, rs707463, rs697686, rs2301488, rs10864255, rs2071918, rs9434833, rs6698901, rs4908575, rs6657847, rs11121029, rs4243823 |
| CBLN1 | rs9935379, rs12598711, rs1469906, rs893175 |
| CDH11 | rs35216, rs35195, rs35186, rs35144, rs40115, rs35140, rs4625747, rs35164, rs35162, rs35165, rs4967886 |
| CDH8 | rs11075445, rs1397126, rs13336134, rs9302540, rs9925201, rs7189354, rs4784163, rs6498806, rs4416006, rs16964164, rs11641508, rs11862752 |
| CHFR | rs4758911, rs11147101, rs7297261 |
| COX10 | rs8077302, rs1003060 |
| CTNND1 | rs1786438 |
| DAAM1 | rs7143953, rs10873113, rs8004164, rs10483710, rs1271513, rs941886, rs4901909, rs12590850, rs1958180, rs1547199, rs12589351, rs4901921, rs2053298, rs1957409, rs6573250, rs2099636, rs17096088 |
| DACT1 | rs863091 |
| DCC | rs1031062, rs882333, rs4998815, rs12967277, rs7228674, rs9954344, rs7506909, rs2270954, rs9949949, rs11082964, rs2036415, rs8089980, rs9966074, rs10515959, rs17504520, rs11876282, rs1502229, rs4940259, rs12605899, rs17506154, rs8088048, rs16954731, rs7504750, rs9953016, rs9807201, rs10853622, rs10853621, rs12455180, rs10502969 |
| DEAF1 | rs10902190, rs936465, rs7123677 |
| DNM3 | rs6690848, rs9425606, rs9425598, rs4072117, rs12410416, rs12075807, rs10910966, rs7540873, rs1063412, rs6701929, rs7550558, rs2586389, rs2586392, rs10158839 |
| DPH3 | rs842252, rs842264, rs842261, rs2470508, rs842251, rs842259, rs842254 |
| DTX4 | rs2211912, rs3847, rs544864 |
| DUSP8 | rs1554857, rs7396009, rs1108991, rs10734456 |
| DYM | rs577979, rs7239949, rs357894, rs16950298 |
| EML1 | rs8013843, rs12435250, rs3818279, rs4900447, rs11160554, rs1957509, rs1191109, rs11623084, rs17099031, rs10150225, rs10131519, rs1005766, rs8020741, rs2250718, rs12590861, rs975252, rs11850280, rs3783322 |
| EVL | rs1190967, rs10148930, rs2400848, rs10136836, rs12431406 |
| EXOC2 | rs12154040, rs2073008, rs1150856, rs9405242, rs2473484, rs17135931 |
| FASLG | rs10458360 |
| FUSSEL18 | rs2164098, rs11877471, rs8086549, rs9304344, rs9965170, rs11082575, rs11663646, rs17785419, rs7244178 |
| GCOM1 | rs2470360, rs1873993, rs9302201, rs1425948, rs9806498, rs16977629, rs7176042, rs11638184, rs11071337 |
| GPR135 | rs1253103, rs2774052, rs4898989, rs1273156, rs1253170 |
| GRINL1A | rs2470360, rs9302201, rs11071337, rs9806498, rs7176042, rs11638184, rs1873995, rs16977629, rs1873993 |
| HCCA2 | rs7396009, rs1554857, rs1108991, rs10734456 |
| HERC2 | rs8041209, rs2346050, rs6497292, rs916977, rs6497272 |

TABLE C-continued

Exemplary SNPs in Linkage Disequilibrium with Table B SNPs

| Gene | SNPs in linkage disequilibrium with those in Table B |
|---|---|
| HSD17B12 | rs7482725, rs10838166, rs10768983, rs11037691, rs10838186, rs17596617, rs10838184, rs938942, rs7116641 |
| IGF1R | rs1879613, rs4966012, rs11633717, rs1879612, rs1521481, rs7165181, rs11634874, rs4966036, rs951715, rs7173377, rs3743258 |
| KATNAL2 | rs2010834, rs4986203, rs2571034, rs2576040 |
| KCNA10 | rs1281177 |
| KCNC1 | rs10766426, rs2299637 |
| KCND3 | rs584096, rs1373291, rs544941, rs197412 |
| KCNH1 | rs10863854, rs1777264, rs1340127, rs1777256, rs1875438, rs7529770, rs4951495, rs11119679, rs1501555, rs7546472 |
| KCNQ1 | rs2283179 |
| KIAA0182 | rs1053328, rs9940601, rs732460, rs736845 |
| KIAA0427 | rs2337099, rs12458062, rs1384227, rs1023943, rs12456253, rs9952398, rs8083702, rs1994559, rs937021 |
| KIAA0513 | rs3794682, rs8063083, rs715707 |
| KIAA1545 | rs4242909 |
| KIAA1853 | rs4298970, rs4767783, rs1541764, rs4075945, rs7966721, rs1568922, rs10851061, rs7298478 |
| KLHL25 | rs870689, rs17623915, rs10520595, rs11637212, rs8025135, rs2241266, rs2430838 |
| LRRC4C | rs2953310, rs10501227, rs10501225, rs1377106 |
| N4BP1 | rs8046716, rs2129243 |
| NAV2 | rs10732471, rs2255677, rs2119981, rs12099330, rs2625312, rs1867116, rs11025328, rs1982265, rs1559665, rs10500860, rs7119267 |
| NDRG2 | rs1243446 |
| NDRG4 | rs1058132, rs16960170, rs40359 |
| NEDD4 | rs11630780, rs4520787, rs9972348, rs12916104, rs10518831, rs1509408, rs2175104 |
| NETO2 | rs9928466 |
| OTOG | rs734640, rs869108, rs11024348, rs2237959, rs972676, rs10766410, rs4757560, rs757982, rs7111528, rs11024357 |
| PER3 | rs697686, rs707463, rs228688, rs228652 |
| PHACS | rs7950395, rs3134907 |
| PMP22 | rs231020, rs230915, rs192046, rs2323653, rs10852830, rs230911, rs11656487 |
| PTPN5 | rs7117716, rs4757718, rs4075664, rs755796, rs11024782, rs7950091, rs11024786 |
| RABGAP1L | rs1793319, rs10912854 |
| RERE | rs4581300, rs6577499, rs12024032, rs10779702 |
| RHOG | rs11030008, rs1869002, rs1055640 |
| RIMBP2 | rs4759462, rs1877978 |
| RP1-21O18.1 | rs761288, rs4501834, rs1000313, rs4661563, rs6665012, rs10803343 |
| RTN1 | rs1957311, rs17731838, rs1884737, rs12878097, rs17256003, rs1951366 |
| SERGEF | rs4141243, rs11024415, rs2299628, rs2283233, rs4757589 |
| SLC16A4 | rs3768458 |
| SLC17A6 | rs1562445, rs2078352, rs11026546, rs721840 |
| SLC6A17 | rs17671169, rs6689641, rs2784140, rs1571346 |
| SLC6A5 | rs16906507 |
| SLCO3A1 | rs8027160, rs975721, rs12905912, rs11630872, rs207954, rs8032981 |
| SMAD2 | rs10502890, rs1792670 |
| SMAD4 | rs7243135, rs1789223 |
| SMAD7 | rs2337153, rs12953717 |
| STX2 | rs10848205, rs7956851 |
| SV2B | rs1117387, rs1002556, rs11631712, rs6496778, rs17516708, rs2269799, rs1079535, rs6496780, rs2106692, rs11630131, rs2239994 |
| SYT13 | rs7943596, rs1075778, rs1077491, rs6485608, rs7118408, rs7124508, rs12362444, rs4755941, rs7117240 |
| SYT14 | rs6701631, rs7543650, rs12029138 |
| TEP1 | rs1760909, rs1713448, rs1713449, rs1713419 |
| TOLLIP | rs2672812, rs2014486 |
| TTC5 | rs2318864, rs11623837, rs4981148, rs4981951, rs8022565, rs4981948 |
| ULK1 | rs10794440 |
| UNC13C | rs8023723, rs500853, rs8025195, rs573320, rs12912762, rs934192, rs7163424, rs8024165, rs12917023, rs16974712, rs12900128, rs1961635, rs1864416, rs2115820, rs8024845, rs2115825, rs12148800, rs1897069, rs9920150, rs17731958 |
| USH1C | rs4756895, rs1076311, rs2237961, rs2041032, rs972676, rs1064074, rs10766410, rs2237959 |
| VAMP4 | rs9943293, rs10913529 |
| WDR25 | rs11160589, rs7492607 |
| YPEL4 | rs1798173 |
| ZFP91-CNTF | rs2509920, rs948562 |
| ZNF423 | rs4785185 |

Identification of Additional Markers by Linkage Disequilibrium Analysis

Linkage disequilibrium (LD) is a measure of the degree of association between alleles in a population. One of skill in the art will appreciate that haplotypes involving markers in LD with the polymorphisms described herein can also be used in a similar manner to those described herein. Methods of calculating LD are known in the art (see, e.g., Morton et al., Proc Natl Acad Sci USA 98(9):5217-21 (2001); Tapper et al., Proc Natl Acad Sci USA 102(33):11835-11839 (2005); Maniatis et al., Proc Natl Acad Sci USA 99:2228-2233 (2002)).

Thus, in some embodiments, the methods include analysis of polymorphisms that are in LD with a polymorphism described herein. Methods are known in the art for identifying such polymorphisms; for example, the International HapMap Project provides a public database that can be used, see hapmap.org, as well as The International HapMap Consortium, Nature 426:789-796 (2003), and The International HapMap Consortium, Nature 437:1299-1320 (2005). Generally, it will be desirable to use a HapMap constructed using data from individuals who share ethnicity with the subject, e.g., a HapMap for African Americans would ideally be used to identify markers in LD with an exemplary marker described herein for use in genotyping a subject of African American descent.

Alternatively, methods described herein can include analysis of polymorphisms that show a correlation coefficient ($r^2$) of value $\geq 0.5$ with the markers described herein. Results can be obtained, e.g., from on line public resources such as HapMap.org. The correlation coefficient is a measure of LD, and reflects the degree to which alleles at two loci (for example two SNPs) occur together, such that an allele at one SNP position can predict the correlated allele at a second SNP position, in the case where $r^2$ is >0.

Incorporation of Additional Haplotypes Associated with SZ, Pharmacological Response, and Psychiatric Endophenotypes In some embodiments, the methods described herein can include determining the presence of a haplotype that includes one or more additional polymorphisms associated with SZ, pharmacological response, and psychiatric endophenotypes.

By way of example, numerous studies have implicated various phosphatidylinositol kinases in SZ, including PIP5K2A (Bakker et al., Genes Brain Behav. 6:113-119 (2007)) and PI3K via interaction with AKT (Kalkman, Pharmacol. Ther. 110:117-134 (2006)). The use of variants in the PI4K2B gene in SZ diagnosis and pharmacogenomics has been described, see, e.g., International Patent Application No. PCT/US2007/078399. Additionally, insulin and diacylglycerol interact with the inositol pathways. As described herein, combining such findings with protein-protein interaction data, pathway analyses, and the large literature on genetic linkage studies for neuropsychiatric illnesses, has allowed the present inventors to identify a number of inositol, insulin and diacylglycerol genes that can be used for SZ risk assessment, diagnosis and pharmacogenomics.

As a second example, potassium channels and potassium current signaling molecules interact with many pathways including dopamine signaling pathways (Canavier et al., J. Neurophysiol. 98:3006-3022 (2007)). The potassium channel gene KCNIP4 has been implicated in schizophrenia risk, see, e.g., International Patent Application No. PCT/US2007/078399. Other groups have reported the possible involvement of KCNN3 polymorphisms in SZ (Ivkovic et al., Int. J. Neurosci. 116:157-164 (2006). As described herein, several additional potassium channel genes, as well as genes that produce proteins that interact with potassium pathways, have been identified that are predicted to play a role in SZ risk and/or drug response.

In some embodiments, the methods described herein can include determining the presence of a haplotype that includes one or more polymorphisms near D22S526 and/or the polymorphisms in the Sult4a1 gene and/or polymorphisms within 1 LDU of these markers, e.g., as described in U.S. Pat. Pub. No. 2006-0177851, incorporated herein in its entirety.

In some embodiments, the methods described herein can include determining the presence of a haplotype that includes one or more polymorphisms in the PI4K2B gene and/or polymorphisms in the KCNIP4 gene and/or polymorphisms in the CERK gene and/or polymorphisms in the SHANK3 gene and/or polymorphisms within 1 LDU of these markers, e.g., as described in International Pat. Application No. PCT/US2007/078399 and US Pat. Pub. No. 2009-0012371, incorporated herein in its entirety.

In some embodiments, the methods described herein can include determining the presence of a haplotype that includes one or more polymorphisms in the HPCAL1 gene and/or the polymorphisms in the SV2C gene and/or polymorphisms in linkage disequilibrium with these markers, e.g., as described in International Pat. Application No. PCT/US2008/088061, incorporated herein in its entirety.

In some embodiments, the methods include determining the presence of a haplotype that includes one or more polymorphisms in the novel SZ-spectrum genes and/or the polymorphisms in linkage disequilibrium with specific markers in these genes, e.g., as described in PCT/US2009/030057, incorporated herein in its entirety.

Identification of Additional Markers for Use in the Methods Described Herein

In general, genetic markers can be identified using any of a number of methods well known in the art. For example, numerous polymorphisms in the regions described herein are known to exist and are available in public databases, which can be searched using methods and algorithms known in the art. Alternately, polymorphisms can be identified by sequencing either genomic DNA or cDNA in the region in which it is desired to find a polymorphism. According to one approach, primers are designed to amplify such a region, and DNA from a subject is obtained and amplified. The DNA is sequenced, and the sequence (referred to as a "subject sequence" or "test sequence") is compared with a reference sequence, which can represent the "normal" or "wild type" sequence, or the "affected" sequence. In some embodiments, a reference sequence can be from, for example, the human draft genome sequence, publicly available in various databases, or a sequence deposited in a database such as GenBank. In some embodiments, the reference sequence is a composite of ethnically diverse individuals.

In general, if sequencing reveals a difference between the sequenced region and the reference sequence, a polymorphism has been identified. The fact that a difference in nucleotide sequence is identified at a particular site that determines that a polymorphism exists at that site. In most instances, particularly in the case of SNPs, only two polymorphic variants will exist at any location. However, in the case of SNPs, up to four variants may exist since there are four naturally occurring nucleotides in DNA. Other polymorphisms, such as insertions and deletions, may have more than four alleles.

Other Genetic Markers of Schizophrenia

The methods described herein can also include determining the presence or absence of other markers known or suspected to be associated with SZ, or with SD, or SPD, e.g., markers outside of a region identified herein, see, e.g., Harrison and Owen, Lancet, 361(9355):417-419 (2003), including, for example, markers on chromosome 22 and other chromosomes, e.g., in the region of 22q12.3 (e.g., near D22S283), 22q11.2, 22q11.2, 22g11-q13, 1q42.1, 1q42.1, 1q21-q22, 2p, 2q, 3p25, 4p, 4q, 5q11.2-q13.3, 6p22.3, 6p23, 6q13-q26, 7q, 8p12-21, 8q, 9p, 10p15-p13 (e.g., near D105189), 10q22.3, 11q14-q21, 12q24, 13q34, 13q32, 14q32.3, 15q15, 16p, 17q, 18p, 18q, 19p. 20p, 21q, Xq, and/or the X/Y pseudoautosomal region. In some embodiments, the methods include determining the presence or absence of one or more other markers that are or may be associated with SZ, or with SZ, SD or SPD, e.g., in one or more genes, e.g., ACE (Illi et al., Eur Neuropsychopharmacol 13:147-151 (2003)); ADRA1A (Clark et al., Biol Psychiatry. 58(6):435-9 (2005)); ADH1B (Xu et al., Mol Psychiatry. 9(5):510-21 (2004); Vawter et al., Hum Genet. 119(5):558-70 (2006)); AHI1 (Eur J Hum Genet. 14(10): 1111-9 (2006)); AKT1 (Emamian et al., Nature Genet. 36:131-137 (2004)); ALDH3B1 (Sun et al. Sci. China C. Life. Sci. 48(3):263-9 (2005)); ALK (Kunagi et al., J Neural Transm. 113(10):1569-73 (2006)); APC (Cui et al., Mol Psychiatry (7):669-77 (2005)); APOE (Liu et al., Schizophr Res 62: 225-230 (2003)); ARSA (Marcao et al., Mol Genet Metab. 79(4):305-7 (2003); ARVCF (Chen et al., Schizophr Res. 72(2-3):275-7 (2005)); ATXN1 (Pujana et al Hum Genet 99:772-775 (1997); Joo et al., Psychiatr Genet 9:7-11 (1999); Fallin et al., Am J Hum Genet 77:918-936 (2005)); BDNF (Neves-Pereira et al., Molec. Psychiat. 10:208-212 (2005)); BRD1 (Severinsen et al., Mol Psychiatry. 11(12):1126-38 (2006)); BZRP (Kurumaji et al., J Neural Transm. 107(4): 491-500 (2000)); DAO (Owen et al., Trends Genet. 21(9): 518-25 (2005)); DAOA (Owen et al., 2005, supra); CAPON (Brzustowicz et al., Am J Hum Genet. 74(5):1057-63 (2004)); CCKAR (Zhang et al., Mol Psychiatry 5:239-240 (2000); Sanjuan et al., Eur Psychiatry 19:349-353 (2004)); CHGB (Kitao et al., Psychiatr Genet 10:139-143 (2000); Zhang et al., Neurosci Lett 323:229-233 (2002)); CHI3L1 (Zhao et al., Am J Hum Genet. 80(1):12-8 (2007)); CHRNA2 (Blaveri et al., Europ. J. Hum. Genet. 9: 469-472 (2001)); CHRNA7 (Leonard et al. Arch Gen Psychiatry. 2002 59:1085-1096 (2002); De Luca et al. Neuropsychobiology. 50:124-127 (2004)); CLDN5 (Sun et al., Eur Psychiatry 19:354-357 (2004); Wei and Hemmings, Prostaglandins Leukot Essent Fatty Acids 73(6)4:41-445 (2005)); COMT (Shifman et al., Am. J. Hum. Genet. 71:1296-1302 (2002)); CNR1 (Ujike et al., Mol Psychiatry 7:515-518 (2002)); CPLX2 (Lee et al., Behav Brain Funct. 1:15 (2005)); DGCR8 (Jacquet et al., Hum Mol Genet. 11(19):2243-9 (2002)); DISC1 (Owen et al., 2005, supra; see, e.g., the D1S2709 marker (Ekelend et al., Hum. Molec. Genet. 10:1611-1617 (2001), DDR1 (Roig et al., Mol Psychiatry. 12(9); 833-41 (2007); DRD4 (Lung et al., Schizophr Res 57:239-245 (2002)); DDR3 (Williams et al., Mol Psychiatry 3:141-149 (1998)); DRD5 (Williams et al., Psychiatr Genet 7:83-85 (1997); Muir et al., Am J Med Genet 105:152-158 (2001)); HEP3 haplotype, Hennah et al., Hum. Molec. Genet. 12: 3151-3159 (2003), and Leu607Pro, Hodgkinson et al., Am. J. Hum. Genet. 75:862-872 (2004), Erratum: Am. J. Hum. Genet. 76:196 (2005)); DISC2 (Millar et al., Ann Med. 36(5):367-78 (2004)); DPYSL2 (Hong et al., Am J Med Genet B Neuropsychiatr Genet. 136(1):8-11 (2005)); DRD1 (Coon et al., Am. J. Hum. Genet. 52: 327-334 (1993)); DRD2 (Glatt et al., Am. J. Psychiat. 160:469-476 (2003)); DRD3 (Rybakowski et al., Molec. Psychiat. 6:718-724 (2001)); DTNBP1 (Owen et al., 2005, supra); EGR3 (Yamada et al., Proc Natl Acad Sci 104(8):2815-20 (2007)); EPSIN4 (Am J Hum Genet. 76(5):902-7 (2005)); ErbB; EGF (Futamura et al., Am. J. Hum. Genet. 52: 327-334 (2002)); ENTH (Pimm et al., Am J Hum Genet 76:902-907 (2005); Tang et al., Mol Psychiatry 11:395-399 (2006)); ERBB4 (Norton et al., Am J Med Genet B Neuropsychiatr Genet 14;11;96-101 (2005)); Silberberg et al., Am J Med Genet B Neuropsychiatr Genet 141B;2;142-148 (2006)); FEZ1 (Yamada et al., Biol Psychiatry 56:683-690(2004)); FOXP2 (Sanjuan et al., Psychiatr Genet. 16(2):67-72 (2006)); FXYD6 (Choudhury et al., Am J Hum Genet. 80(4):664-72 (2007)); FZD3 (Katsu et al., Neurosci Lett 353:53-56 (2003); Yang et al., Biol Psychiatry 54:1298-1301 (2003); Zhang et al., Am J Med Genet 129B:16-19 (2004)); GABRA1, GABRA2, GABRA6, GABRP (Petryshen et al., Mol Psychiatry. 10(12):1057 (2005)); GABBR1 (Zai et al. Eur Neuropsychopharmacol. 15:347-52 (2005); Le-Niculescu et al. Am J Med Genet B Neuropsychiatr Genet. 144:129-58 (2007)); GAD1 (Addington et al., Mol Psychiatry 10:581-588(2005)); GFRA1 (Semba et al., Brain Res Mol Brain Res. 124(1):88-95 (2004)); GCLM (Tosic et al., Am J Hum Genet. 79(3):586-92 (2006)); GNB3 (Kunugi et al., J. Neural Transm. 109(2):213-8 (2002)); GPR78 (Underwood et al., Mol Psychiatry. 11(4):384-94 (2006)); GRIA1 (Magri et al., Am J Med Genet B Neuropsychiatr Genet 141(3):287-93 (2006)); GNPAT (Lin et al., Biol Psychiatry. 60(6):554-62 (2006)); GRID1 (Fallin et al., Am J Hum Genet 77:918-936 (2005)); GRIK1 (Shibata et al., Psychiatr Genet. 11(3):139-44 (2001)); GRIK2 (Shibata et al., Psychiatry Res. 113(1-2): 59-67 (2002)); GRIK3 (Shibata al., Psychiatry Res. 30: 141 (1): 39-51 (2006)); GRIK4 (Pikard et al., Mol Psychiatry 11(9):847-57(2006)); GRIN1 (Qin et al., Eur J Hum Genet. 13(7):807-14 (2005)); GRIN2A, GRIN2B (Abdolmaleky et al., Am J Pharmacogenomics. 5(3):149-60 (2005)); GRIN2D (Makino et al., Psychiatr Genet. 15(3):215-21 (2005)); GRM3 (Egan et al., Proc Natl Acad Sci USA. 101(34):12604-9 (2004)); GRM4 (Ohtsuki et al., Psychiatr Genet. 11(2):79-83 (2001)); GRM5 (Devon et al., Mol Psychiatry. 6(3):311-4 (2001)); GSTM1 (Harada et al., Biochem Biophys Res Commun 281:267-271 (2001); Pae et al., Psychiatr Genet 14:147-150 (2004)); G30/G72 (Schulze et al., Am J Psychiatry. 162(11):2101-8 (2005)); HTR2A (Baritaki et al., Eur J Hum Genet. 12(7):535-41 (2004)); HLA-DRB1 (Schwab et al., Am J Med Genet. 114(3):315-20 (2002)); HLA-BRB3 (Yu et al., Zhonghua Liu Xing Bing Xue Za Zhi. 24(9):815-8 (2003)); HTR5A (Abdolmaleky et al., Schizophr Res 67:53-62 (2004)); HTR6 (Tsai et al., Neurosci Lett. 271 (2):135-7 (1999)); IL1B (Katila et al., Mol Psychiatry 4:179-181(1999); Meisenzahal et al., Am J Psychiatry 158:1316-1319 (2001); Zanardini et al., J Psychiatr Res 37:457-462 (2003)); IL1RN (Zanardini et al., J Psychiatr Res 37:457-462 (2003); Kim et al., Psychiatr Genet 14:165-167 (2004); Papiol et al., Neuroimage 27:1002-1006 (2005)); IL10 (Chiavetto et al., Biol Psychiatry 51:480-484 (2002); Jun et al., Psychiatry Clin Neurosci 56:177-180 (2002)); IL2RB (Schwab et al., Am J Med Genet. 60(5):436-43 (1995)); KCNN3 (Ujike et al., Psychiatry Res. 101(3):203-7 (2001)); KIF13A (Jamain et al., Genomics. 74(1):36-44 (2001)); KIF2A (Li et al., Neurosci Letters 407(2) 151-5 (2006)); KPNA3 (Wei and Hemmings, Neurosci Res. 52(4):342-6 (2005)); LGI1 (Fallin et al. A J Hum Genet. 77:918-36 (2005)); MAG (Wan et al., Neurosci Lett. 388(3):126-31 (2005)); MAOA (Jonsson et al., Schizophr Res 61:31-37 (2003); Wei and Hemmings. Psychiatr Genet 9, 177-181 (1999)); MED12 (Sandhu et al., Am J Med Genet B Neuropsychiatr Genet. 123B: 33-38 (2003); Spinks et al., Am J Med Genet B Neuropsychiatr Genet. 127B:20-27 (2004)); MLC1 (Verma et al., Biol Psychiatry. 58(1):16-22 (2005)); MTHFR (Lewis et al., Am. J. Med. Genet. (Neuropsychiat. Genet.) 135B:2-4 (2005)); MTR (Kempisty et al., Psychiatr Genet. 17(3):177-81 (2007)); MTHFD1 (Kempisty et al., Psychiatr Genet. 17(3):177-81 (2007)); NCAM1 (Sullivan et al., Biol Psychiatry. 61(7):902-10 (2007)); NDE1 (Hennah et al., Hum Mol Genet. 16(5):453-62 (2006)); NDUFV2 (Waskizuka et al., Am J Med Genet B Neuropsychiatr Genet. 141(3):301-4 (2006)); NOS1 (Liou et al., Schizophr Res. 65(1):57-9 (2003)); NOTCH4 (Wei and Hemmings, (Letter) Nature Genet. 25:376-377 (2000)); NPAS3 (Kamnasaran et al., J Med Genet 40:325-332 (2003)); NRG1 (Owen et al., 2005, supra); NRG3 (Fallin et al. A J Hum Genet. 77:918-36 (2005)); NTNG1 (Fukawasa et al., J Med Dent Sci 51:121-128 (2004); Aoki-Suzuki et al., Biol Psychiatry 57:382-393 (2005)); NTNG2 (Aoki-Suzuki et al., Biol Psychiatry 57:382-393 (2005)); NTF3 (Jonsson et al., Acta Psychiatr Scand 95:414-419 (1997)); OLIG2 (Georgieva et al., Proc Natl Acad Sci 103(33):12469-74 (2006)); PCQAP (Sandhu et al., Psychiatr Genet. 14(3):169-72 (2004)); PDE4B (Millar et al., Science 310:1187-1191 (2005)); PDLIM5 (Horiuchi et al., Biol Psychiatry 59(5):434-9 (2005)); PICK1 (Hong et al., Neuroreport 15:1965-1967 (2004); Fujii et al., Molecular Psychiatry 11:150-157 (2005)); PIK3C3 (Stopkova et al., Biol Psychiatry 55:981-988 (2004); Duan et al., Neurosci Lett., 379:32-36 (2005)); PIK4CA (Saito et al., Am J Med Genet B Neuropsychiatr Genet. 116(1):77-83 (2003)); PIP5K2A (Stopkova et al., Psychiatr Genet. 15(3): 223-7 (2005)); PLA2G4A PLA2G4C (Yu et al., Prostaglandins Leukot Essent Fatty Acids. 73(5):351-4 (2005)); PLA2G4B (Tao et al., Am J Med Genet B Neuropsychiatr Genet 137:56-58 (2005)); PLXNA2 (Mah et al., Molecular Psychiatry 11:471-478 (2006)); PTGS2 (Wei and Hemmings. Prostaglandins Leukot Essent Fatty Acids 70:413-415 (2004)); PPP3CC (Gerber et al., Proc Natl Acad Sci USA. 100(15): 8993-8 (2003)); PNOC (Blaveri et al., 2001); PRODH (Chakravarti, Proc. Nat. Acad. Sci. 99:4755-4756 (2002)); QKI (Aberg et al., Am J Med Genet B Neuropsychiatr Genet. 2005 Dec. 9; [Epub ahead of print]); RGS4 (Chowdari et al., Hum. Molec. Genet. 11:1373-1380 (2002), Erratum: Hum. Molec. Genet. 12:1781 (2003)); RELN (Costa et al., Mol Interv. 2(1):47-57 (2002)); RTN4 (Novak et al., Brain Res Mol Brain Res 107:183-189 (2002); Tan et al., Brain Res Mol Brain Res 139:212-216 (2005)); SCAT (Culkjovic et al., Am J Med Genet. 96(6):884-7 (2000)); SLC15A1 (Maheshwari et al., BMC Genomics. 3(1):30 (2002)); SLC18A1 (Bly, Schizophr Res. 78(2-3):337-8 (2005)); SLC18A2 (Gutierrez et al. Am J Med Genet B Neuropsychiatr Genet. 144(4):502-7 (2007)); SLC6A4 (Fan and Sklar, Mol Psychiatry. 10(10): 928-38, 891 (2005)); SNAP29 (Saito et al., Mol Psychiatry 6(2):193-201 (2001); Erratum in: Mol Psychiatry 6(5):605 (2001); SULT4A1 (Brennan and Chondra. Am J Med Genet B Neuropsychiatr Genet. 139(1):69-72 (2005)); SYNGR1 (Verma et al., Biol Psychiatry. 55(2):196-9 (2004)); SYN2 (Chen et al., Bio. Psychiat. 56:177-181 (2004)); SYN3 (Porton et al. Biol Psychiatry. 55(2):118-25 (2004)); TAAR4 (Duan et al., Am J Hum Genet 75:624-638 (2004)); TBP/SCA17 (Chen et al., Schizophr Res. 78(2-3):131-6 (2005)); TH (Kurumaji et al., J Neural Transm 108:489-495 (2001); Meloni et al., C R Acad Sci III 318:803-809 (1995)); TNFA (Morar et al., Am J Med Genet B Neuropsychiatr Genet. 144(3):318-24 (2007)); TPH1 (Nolan et al., Psychiatr Genet 10:109-115 (2000); Hong et al., Schizophr Res 49:59-63 (2001); Sekizawa et al., Am J Med Genet B Neuropsychiatr Genet 128:24-26 (2004)); TPP2 (Fallin et al. A J Hum Genet. 77:918-36 (2005)); TPS3 (Park et al., Schizophr Res 67:71-74 (2004); Ni et al., Neurosci Lett 388:173-178 (2005)); TRAR4 (Duan et al., Am J Hum Genet. 75(4):624-38 (2004)); TRAX (Thomson et al., Mol Psychiatry. 10(7):657-68, 616 (2005)); UFD1L (De Luca et al., Am J Med Genet. 105(6):529-33 (2001)); UCP2 (Yasuno et al., Am J Med Genet B Neuropsychiatr Genet. 144(2):250-3 (2007)); UCP4 (Yasuno et al., : Am J Med Genet B Neuropsychiatr Genet. 144(2):250-3 (2007)); UHMK1 (Puri et al., Biol Psychiatry 61(7):873-9 (2007)); XBP1 (Chen et al., Biochem Biophys Res Commun 319:866-870 (2004); Kakiuchi et al., Psychiatry Clin Neurosci 58:438-440 (2004)); YWHAH (Toyooka et al., Am J Med Genet. 88(2):164-7 (1999)); ZDHHC8 (Mukai et al., Nature Genet. 36:725-731 (2004)); or ZNF74 (Takase et al., Schizophr Res. 52(3):161-5 (2001)). See also, e.g., OMIM entry no. 181500 (SCZD).

Methods of Determining the Presence or Absence of a Haplotype Associated with SZ, Pharmacological Response, and Psychiatric Endophenotypes The methods described herein include determining the presence or absence of haplotypes associated with SZ, pharmacological response, and psychiatric endophenotypes. In some embodiments, an association with SZ is determined by the presence of a shared haplotype between the subject and an affected reference individual, e.g., a first or second-degree relation of the subject, or population of affected individuals, and the absence of the haplotype in an unaffected reference individual. In some embodiments, an association with a pharmacological response is determined by the presence of a shared haplotype between the subject and a reference individual (or population) who had an identified response to a pharmacological treatment. In some embodiments, an association with a specific psychiatric endophenotype is determined by the presence of a shared haplotype between the subject and a reference subject or population with (or without) the specific endophenotype. Thus the methods can also include obtaining and analyzing a sample from a suitable reference individual.

Samples that are suitable for use in the methods described herein contain genetic material, e.g., genomic DNA (gDNA). Non-limiting examples of sources of samples include urine, blood, and tissue. The sample itself will typically consist of nucleated cells (e.g., blood or buccal cells), tissue, etc., removed from the subject. The subject can be an adult, child, fetus, or embryo. In some embodiments, the sample is obtained prenatally, either from a fetus or embryo or from the mother (e.g., from fetal or embryonic cells in the maternal circulation). Methods and reagents are known in the art for obtaining, processing, and analyzing samples. In some embodiments, the sample is obtained with the assistance of a health care provider, e.g., to draw blood. In some embodiments, the sample is obtained without the assistance of a health care provider, e.g., where the sample is obtained non-invasively, such as a sample comprising buccal cells that is obtained using a buccal swab or brush, or a mouthwash sample.

The sample may be further processed before the detecting step. For example, DNA in a cell or tissue sample can be separated from other components of the sample. The sample can be concentrated and/or purified to isolate DNA. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al., 2003, supra. All samples obtained from a subject, including those subjected to any sort of further processing, are considered to be obtained from the subject.

The absence or presence of a haplotype associated with SZ, pharmacological response, and/or psychiatric endophenotypes, as described herein can be determined using methods known in the art, e.g., gel electrophoresis, capillary electrophoresis, size exclusion chromatography, sequencing, and/or arrays to detect the presence or absence of the marker(s) of the haplotype. Amplification of nucleic acids, where desirable, can be accomplished using methods known in the art, e.g., PCR.

Methods of nucleic acid analysis to detect polymorphisms and/or polymorphic variants include, e.g., microarray analysis. Hybridization methods, such as Southern analysis, Northern analysis, or in situ hybridizations, can also be used (see *Current Protocols in Molecular Biology*, Ausubel, F. et al., eds., John Wiley & Sons 2003). To detect microdeletions, fluorescence in situ hybridization (FISH) using DNA probes that are directed to a putatively deleted region in a chromosome can be used. For example, probes that detect all or a part of a microsatellite marker can be used to detect microdeletions in the region that contains that marker.

Other methods include direct manual sequencing (Church and Gilbert, Proc. Natl. Acad. Sci. USA 81:1991-1995 (1988); Sanger et al., Proc. Natl. Acad. Sci. 74:5463-5467 (1977); Beavis et al. U.S. Pat. No. 5,288,644); automated fluorescent sequencing; single-stranded conformation polymorphism assays (SSCP); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., Proc. Natl. Acad. Sci. USA 86:232-236 (1989)), mobility shift analysis (Orita et al., Proc. Natl. Acad. Sci. USA 86:2766-2770 (1989)), restriction enzyme analysis (Flavell et al., Cell 15:25 (1978); Geever et al., Proc. Natl. Acad. Sci. USA 78:5081 (1981)); quantitative real-time PCR (Raca et al., Genet Test 8(4):387-94 (2004)); heteroduplex analysis; chemical mismatch cleavage (CMC) (Cotton et al., Proc. Natl. Acad. Sci. USA 85:4397-4401 (1985)); RNase protection assays (Myers et al., Science 230:1242 (1985)); use of polypeptides that recognize nucleotide mismatches, e.g., *E. coli* mutS protein; allele-specific PCR, for example. See, e.g., U.S. Patent Publication No. 2004/0014095, to Gerber et al., which is incorporated herein by reference in its entirety. In some embodiments, the methods described herein include determining the sequence of the entire region of the genes listed in Tables A and B e.g. between and including the delimiting SNPs for the particular gene. In some embodiments, the sequence is determined on both strands of DNA.

In order to detect polymorphisms and/or polymorphic variants, it will frequently be desirable to amplify a portion of genomic DNA (gDNA) encompassing the polymorphic site. Such regions can be amplified and isolated by PCR using oligonucleotide primers designed based on genomic and/or cDNA sequences that flank the site. See e.g., *PCR Primer: A Laboratory Manual*, Dieffenbach and Dveksler, (Eds.); McPherson et al., *PCR Basics: From Background to Bench* (Springer Verlag, 2000); Mattila et al., Nucleic Acids Res., 19:4967 (1991); Eckert et al., *PCR Methods and Applications*, 1:17 (1991); PCR (eds. McPherson et al., IRL Press, Oxford); and U.S. Pat. No. 4,683,202. Other amplification methods that may be employed include the ligase chain reaction (LCR) (Wu and Wallace, Genomics, 4:560 (1989), Landegren et al., Science, 241:1077 (1988), transcription amplification (Kwoh et al., Proc. Natl. Acad. Sci. USA, 86:1173 (1989)), self-sustained sequence replication (Guatelli et al., Proc. Nat. Acad. Sci. USA, 87:1874 (1990)), and nucleic acid based sequence amplification (NASBA). Guidelines for selecting primers for PCR amplification are well known in the art. See, e.g., McPherson et al., *PCR Basics: From Background to Bench*, Springer-Verlag, 2000. A variety of computer programs for designing primers are available, e.g., 'Oligo' (National Biosciences, Inc, Plymouth Minn.), MacVector (Kodak/IBI), and the GCG suite of sequence analysis programs (Genetics Computer Group, Madison, Wis. 53711).

In one example, a sample (e.g., a sample comprising genomic DNA), is obtained from a subject. The DNA in the sample is then examined to determine a haplotype as described herein. The haplotype can be determined by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular polymorphic variant.

In some embodiments, a peptide nucleic acid (PNA) probe can be used instead of a nucleic acid probe in the hybridization methods described above. PNA is a DNA mimetic with a peptide-like, inorganic backbone, e.g., N-(2-aminoethyl)glycine units, with an organic base (A, G, C, T or U) attached to the glycine nitrogen via a methylene carbonyl linker (see, e.g., Nielsen et al., *Bioconjugate Chemistry*, The American Chemical Society, 5:1 (1994)). The PNA probe can be designed to specifically hybridize to a nucleic acid comprising a polymorphic variant conferring susceptibility to or indicative of the presence of SZ.

In some embodiments, restriction digest analysis can be used to detect the existence of a polymorphic variant of a polymorphism, if alternate polymorphic variants of the polymorphism result in the creation or elimination of a restriction site. A sample containing genomic DNA is obtained from the individual. Polymerase chain reaction (PCR) can be used to amplify a region comprising the polymorphic site, and restriction fragment length polymorphism analysis is conducted (see Ausubel et al., *Current Protocols in Molecular Biology*, supra). The digestion pattern of the relevant DNA fragment indicates the presence or absence of a particular polymorphic variant of the polymorphism and is therefore indicative of the presence or absence of susceptibility to SZ.

Sequence analysis can also be used to detect specific polymorphic variants. A sample comprising DNA or RNA is obtained from the subject. PCR or other appropriate methods can be used to amplify a portion encompassing the polymorphic site, if desired. The sequence is then ascertained, using any standard method, and the presence of a polymorphic variant is determined.

Allele-specific oligonucleotides can also be used to detect the presence of a polymorphic variant, e.g., through the use of dot-blot hybridization of amplified oligonucleotides with allele-specific oligonucleotide (ASO) probes (see, for example, Saiki et al., Nature (London) 324:163-166 (1986)). An "allele-specific oligonucleotide" (also referred to herein as an "allele-specific oligonucleotide probe") is typically an oligonucleotide of approximately 10-50 base pairs, preferably approximately 15-30 base pairs, that specifically hybridizes to a nucleic acid region that contains a polymorphism. An allele-specific oligonucleotide probe that is specific for particular a polymorphism can be prepared using standard methods (see Ausubel et al., *Current Protocols in Molecular Biology*, supra).

Generally, to determine which of multiple polymorphic variants is present in a subject, a sample comprising DNA is obtained from the individual. PCR can be used to amplify a portion encompassing the polymorphic site. DNA containing the amplified portion may be dot-blotted, using standard methods (see Ausubel et al., *Current Protocols in Molecular Biology*, supra), and the blot contacted with the oligonucleotide probe. The presence of specific hybridization of the probe to the DNA is then detected. Specific hybridization of an allele-specific oligonucleotide probe (specific for a polymorphic variant indicative of susceptibility to SZ) to DNA from the subject is indicative of susceptibility to SZ.

In some embodiments, fluorescence polarization template-directed dye-terminator incorporation (FP-TDI) is used to determine which of multiple polymorphic variants of a polymorphism is present in a subject (Chen et al., (1999) Genome Research, 9(5):492-498). Rather than involving use of allele-specific probes or primers, this method employs primers that terminate adjacent to a polymorphic site, so that extension of the primer by a single nucleotide results in incorporation of a nucleotide complementary to the polymorphic variant at the polymorphic site.

Real-time pyrophosphate DNA sequencing is yet another approach to detection of polymorphisms and polymorphic variants (Alderborn et al., (2000) Genome Research, 10(8): 1249-1258). Additional methods include, for example, PCR amplification in combination with denaturing high performance liquid chromatography (dHPLC) (Underhill, P. A., et al., Genome Research, Vol. 7, No. 10, pp. 996-1005, 1997).

The methods can include determining the genotype of a subject with respect to both copies of the polymorphic site present in the genome. For example, the complete genotype may be characterized as −/−, as −/+, or as +/+, where a minus sign indicates the presence of the reference or wild type sequence at the polymorphic site, and the plus sign indicates the presence of a polymorphic variant other than the reference sequence. If multiple polymorphic variants exist at a site, this can be appropriately indicated by specifying which ones are present in the subject. Any of the detection means described herein can be used to determine the genotype of a subject with respect to one or both copies of the polymorphism present in the subject's genome.

In some embodiments, it is desirable to employ methods that can detect the presence of multiple polymorphisms (e.g., polymorphic variants at a plurality of polymorphic sites) in parallel or substantially simultaneously. Oligonucleotide arrays represent one suitable means for doing so. Other methods, including methods in which reactions (e.g., amplification, hybridization) are performed in individual vessels, e.g., within individual wells of a multi-well plate or other vessel may also be performed so as to detect the presence of multiple polymorphic variants (e.g., polymorphic variants at a plurality of polymorphic sites) in parallel or substantially simultaneously according to certain embodiments of the invention.

Probes

Nucleic acid probes can be used to detect and/or quantify the presence of a particular target nucleic acid sequence within a sample of nucleic acid sequences, e.g., as hybridization probes, or to amplify a particular target sequence within a sample, e.g., as a primer. Probes have a complimentary nucleic acid sequence that selectively hybridizes to the target nucleic acid sequence. In order for a probe to hybridize to a target sequence, the hybridization probe must have sufficient identity with the target sequence, i.e., at least 70%, e.g., 80%, 90%, 95%, 98% or more identity to the target sequence. The probe sequence must also be sufficiently long so that the probe exhibits selectivity for the target sequence over non-target sequences. For example, the probe will be at least 20, e.g., 25, 30, 35, 50, 100, 200, 300, 400, 500, 600, 700, 800, 900 or more, nucleotides in length. In some embodiments, the probes are not more than 30, 50, 100, 200, 300, 500, 750, or 1000 nucleotides in length. Probes are typically about 20 to about $1 \times 10^6$ nucleotides in length. Probes include primers, which generally refers to a single-stranded oligonucleotide probe that can act as a point of initiation of template-directed DNA synthesis using methods such as PCR (polymerase chain reaction), LCR (ligase chain reaction), etc., for amplification of a target sequence.

In some embodiments, the probe is a test probe, e.g., a probe that can be used to detect polymorphisms in a region described herein, e.g., polymorphisms as described herein. In some embodiments, the probe can hybridize to a target sequence within a region delimited by delimiting SNPs, SNP1 and SNP2, inclusive as specified for the particular genes in Tables A and B.

In some embodiments, the probe can bind to another marker sequence associated with SZ as described herein.

Control probes can also be used. For example, a probe that binds a less variable sequence, e.g., repetitive DNA associated with a centromere of a chromosome, can be used as a control. Probes that hybridize with various centromeric DNA and locus-specific DNA are available commercially, for example, from Vysis, Inc. (Downers Grove, Ill.), Molecular Probes, Inc. (Eugene, Oreg.), or from Cytocell (Oxfordshire, UK). Probe sets are available commercially, e.g., from Applied Biosystems, e.g., the Assays-on-Demand SNP kits Alternatively, probes can be synthesized, e.g., chemically or in vitro, or made from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, Biotechnic. Histochem., 1998, 73(1):6-22, Wheeless et al., Cytometry 1994, 17:319-326, and U.S. Pat. No. 5,491,224.

In some embodiments, the probes are labeled, e.g., by direct labeling, with a fluorophore, an organic molecule that fluoresces after absorbing light of lower wavelength/higher energy. A directly labeled fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker The fluorophore then is covalently attached to the transaminated deoxycytidine nucleotides. See, e.g., U.S. Pat. No. 5,491,224.

Fluorophores of different colors can be chosen such that each probe in a set can be distinctly visualized. For example, a combination of the following fluorophores can be used: 7-amino-4-methylcoumarin-3-acetic acid (AMCA), Texas Red™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethyl-rhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4, 4-difluoro-5,7-dimethyl-4-bora-3a,4a diaza-3-indacenepropionic acid, eosin-5-isothiocyanate, erythrosin-5-isothiocyanate, and Cascade™ blue acetylazide (Molecular Probes, Inc., Eugene, Oreg.). Fluorescently labeled probes can be viewed with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the probes. Fluorescence-based arrays are also known in the art.

In other embodiments, the probes can be indirectly labeled with, e.g., biotin or digoxygenin, or labeled with radioactive isotopes such as $^{32}$P and $^{3}$H. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Oligonucleotide probes that exhibit differential or selective binding to polymorphic sites may readily be designed by one of ordinary skill in the art. For example, an oligonucleotide that is perfectly complementary to a sequence that encompasses a polymorphic site (i.e., a sequence that includes the polymorphic site, within it or at one end) will generally hybridize preferentially to a nucleic acid comprising that sequence, as opposed to a nucleic acid comprising an alternate polymorphic variant.

Arrays and Uses Thereof

In another aspect, the invention features arrays that include a substrate having a plurality of addressable areas, and methods of using them. At least one area of the plurality includes a nucleic acid probe that binds specifically to a sequence comprising a polymorphism listed in Table B, and can be used to detect the absence or presence of said polymorphism, e.g., one or more SNPs, microsatellites, minisatellites, or indels, as described herein, to determine a haplotype. For example, the array can include one or more nucleic acid probes that can be used to detect a polymorphism listed in Table B. In some embodiments, the array further includes at least one area that includes a nucleic acid probe that can be used to specifically detect another marker associated with SZ as described herein. The substrate can be, e.g., a two-dimensional substrate known in the art such as a glass slide, a wafer (e.g., silica or plastic), a mass spectroscopy plate, or a three-dimensional substrate such as a gel pad. In some embodiments, the probes are nucleic acid capture probes.

Methods for generating arrays are known in the art and include, e.g., photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145). The array typically includes oligonucleotide probes capable of specifically hybridizing to different polymorphic variants. According to the method, a nucleic acid of interest, e.g., a nucleic acid encompassing a polymorphic site, (which is typically amplified) is hybridized with the array and scanned. Hybridization and scanning are generally carried out according to standard methods. See, e.g., Published PCT Application Nos. WO 92/10092 and WO 95/11995, and U.S. Pat. No. 5,424,186. After hybridization and washing, the array is scanned to determine the position on the array to which the nucleic acid hybridizes. The hybridization data obtained from the scan is typically in the form of fluorescence intensities as a function of location on the array.

Arrays can include multiple detection blocks (i.e., multiple groups of probes designed for detection of particular polymorphisms). Such arrays can be used to analyze multiple different polymorphisms. Detection blocks may be grouped within a single array or in multiple, separate arrays so that varying conditions (e.g., conditions optimized for particular polymorphisms) may be used during the hybridization. For example, it may be desirable to provide for the detection of those polymorphisms that fall within G-C rich stretches of a genomic sequence, separately from those falling in A-T rich segments.

Additional description of use of oligonucleotide arrays for detection of polymorphisms can be found, for example, in U.S. Pat. Nos. 5,858,659 and 5,837,832. In addition to oligonucleotide arrays, cDNA arrays may be used similarly in certain embodiments of the invention.

The methods described herein can include providing an array as described herein; contacting the array with a sample, e.g., a portion of genomic DNA that includes at least a portion of human chromosome 1, 3, 6, 10, 11, 12, 13, 14, 15, 15, 17, 18, 19, and/or 20, e.g., a region between delimiting SNPs, SNP1 and SNP2 for each of the genes listed in Tables A and B, and/or optionally, a different portion of genomic DNA, e.g., a portion that includes a different portion of human chromosomes 1, 3, 6, 10, 11, 12, 13, 14, 15, 15, 17, 18, 19, and/or 20, or another chromosome, e.g., including another region associated with SZ, pharmacological response, and/or psychiatric endophenotypes, and detecting binding of a nucleic acid from the sample to the array. Optionally, the method includes amplifying nucleic acid from the sample, e.g., genomic DNA that includes a portion of a human chromosome described herein, and, optionally, a region that includes another region associated with SZ, pharmacological response, and/or psychiatric endophenotypes, prior to or during contact with the array.

In some aspects, the methods described herein can include using an array that can ascertain differential expression patterns or copy numbers of one or more genes in samples from normal and affected individuals (see, e.g., Redon et al., Nature. 444(7118):444-54 (2006)). For example, arrays of probes to a marker described herein can be used to measure polymorphisms between DNA from a subject having SZ and control DNA, e.g., DNA obtained from an individual that does not have SZ and has no familial risk factors for SZ. Since the clones on the array contain sequence tags, their positions on the array are accurately known relative to the genomic sequence. Different hybridization patterns between DNA from an individual afflicted with SZ and DNA from a normal individual at areas in the array corresponding to markers in human chromosome 1, 3, 6, 10, 11, 12, 13, 14, 15, 15, 17, 18, 19, and/or 20 as described herein, and, optionally, one or more other regions associated with SZ, SD, or SPD, are indicative of a risk of SZ-spectrum disorders. Methods for array production, hybridization, and analysis are described, e.g., in Snijders et al., (2001) *Nat. Genetics* 29:263-264; Klein et al., (1999) Proc. Natl Acad. Sci. U.S.A. 96:4494-4499; Albertson et al., (2003) Breast Cancer Research and Treatment 78:289-298; and Snijders et al. "BAC microarray based comparative genomic hybridization." In: Zhao et al. (eds), *Bacterial Artificial Chromosomes: Methods and Protocols*, Methods in Molecular Biology, Humana Press, 2002. Real time quantitative PCR can also be used to determine copy number.

In another aspect, the invention features methods of determining the absence or presence of a haplotype associated with SZ, pharmacological response, and/or psychiatric endophenotypes, as described herein, using an array described above. For example, in some embodiments the methods include providing a two dimensional array having a plurality of addresses, each address of the plurality being positionally distinguishable from each other address of the plurality having a unique nucleic acid capture probe, contacting the array with a first sample from a test subject who is suspected of having or being at risk for SZ, and comparing the binding of the first sample with one or more references, e.g., binding of a sample from a subject who is known to have SZ and/or binding of a sample from a subject who is unaffected, e.g., a control sample from a subject that does not have SZ. In some embodiments, the methods include contacting the array with a second sample from a subject who has SZ; and comparing the binding of the first sample with the binding of the second sample. In some embodiments, the methods include contacting the array with a third sample from a subject that does not have SZ; and comparing the binding of the first sample with the binding of the third sample. In some embodiments, the second and third samples are from first or second-degree relatives of the test subject. Binding, e.g., in the case of a nucleic acid hybridization, with a capture probe at an address of the plurality, can be detected by any method known in the art, e.g., by detection of a signal generated from a label attached to the nucleic acid.

Schizophrenia, Schizotypal Personality Disorder, and Schizoaffective Disorder

The methods described herein can be used to determine an individual's risk of developing schizophrenia (SZ), which as defined herein includes narrowly defined SZ as well as schizotypal personality disorder (SPD), and/or schizoaffective disorder (SD).

Schizophrenia (SZ)

SZ is considered a clinical syndrome, and is probably a constellation of several pathologies. Substantial heterogeneity is seen between cases; this is thought to reflect multiple overlapping etiologic factors, including both genetic and environmental contributions. A diagnosis of SZ is typically indicated by chronic psychotic symptoms, e.g., hallucinations and delusions. Disorganization of thought and behavior are common and are considered distinguishing factors in the diagnosis of SZ. Patients typically have some subtle impairments in cognition. Reduced emotional experience and expression, low drive, and impaired speech are observed in a subgroup of patients. Cognitive, emotional and social impairments often appear early in life, while the psychotic symptoms typically manifest in late adolescence or early adulthood in men, a little later in women.

A diagnosis of SZ can be made according to the criteria reported in the *Diagnostic and Statistical Manual of Mental Disorders, Fourth Edition, Text Revision*, American Psychiatric Association, 2000, (referred to herein as DSM-IV) as follows:

Diagnostic Criteria for SZ

All six criteria must be met for a diagnosis of SZ.

A. Characteristic symptoms: Two (or more) of the following, each present for a significant portion of time during a one month period (or less if successfully treated):

(1) delusions
(2) hallucinations
(3) disorganized speech (e.g., frequent derailment or incoherence)
(4) grossly disorganized or catatonic behavior
(5) negative symptoms, e.g., affective flattening, alogia, or avolition Only one criterion A symptom is required if delusions are bizarre or hallucinations consist of a voice keeping up a running commentary on the person's behavior or thoughts, or two or more voices conversing with each other.

B. Social/occupational dysfunction: For a significant portion of the time since the onset of the disturbance, one or more major areas of functioning such as work, interpersonal relations, or self-care are markedly below the level achieved prior to the onset (or when the onset is in childhood or adolescence, failure to achieve expected level of interpersonal, academic, or occupational achievement).

C. Duration: Continuous signs of the disturbance persist for at least 6 months. This 6-month period must include at least 1 month of symptoms (or less if successfully treated) that meet Criterion A (i.e., active-phase symptoms) and may include periods of prodromal or residual symptoms. During these prodromal or residual periods, the signs of the disturbance may be manifested by only negative symptoms or two or more symptoms listed in Criterion A present in an attenuated form (e.g., odd beliefs, unusual perceptual experiences).

D. Schizoaffective and Mood Disorder Exclusion: Schizoaffective Disorder and Mood Disorder With Psychotic Features have been ruled out because either (1) no major depressive, manic, or mixed episodes have occurred concurrently with the active-phase symptoms; or (2) if mood episodes have occurred during active-phase symptoms, their total duration has been brief relative to the duration of the active and residual periods.

E. Substance/General Medical Condition Exclusion: The disturbance is not due to the direct physiological effects of a substance (e.g., a drug of abuse, a medication) or a general medical condition.

F. Relationship to a Pervasive Developmental Disorder: If the patient has a history of Autistic Disorder or another Pervasive Developmental Disorder, the additional diagnosis of SZ is made only if prominent delusions or hallucinations are also present for at least a month (or less if successfully treated).

Schizoaffective Disorder (SD)

SD is characterized by the presence of affective (depressive or manic) symptoms and schizophrenic symptoms within the same, uninterrupted episode of illness.

Diagnostic Criteria for Schizoaffective Disorder

The DSM-IV Criteria for a diagnosis of schizoaffective disorder is as follows:

An uninterrupted period of illness during which, at some time, there is either (1) a Major Depressive Episode (which must include depressed mood), (2) a Manic Episode, or (3) a Mixed Episode, concurrent with symptoms that meet (4) Criterion A for SZ, above.

A. Criteria for Major Depressive Episode

At least five of the following symptoms must be present during the same 2-week period and represent a change from previous functioning; at least one of the symptoms is either (1) depressed mood or (2) loss of interest or pleasure.

(1) depressed mood most of the day, nearly every day, as indicated by either subjective report (e.g., feels sad or empty) or observation made by others (e.g., appears tearful). In children and adolescents, this can be an irritable mood.

(2) markedly diminished interest or pleasure in all, or almost all, activities most of the day, nearly every day (as indicated by either subjective account or observation made by others)

(3) significant weight loss when not dieting or weight gain (e.g., a change of more than 5% of body weight in a month), or decrease or increase in appetite nearly every day. (In children, failure to make expected weight gains is considered).

(4) insomnia or hypersomnia nearly every day (5) psychomotor agitation or retardation nearly every day (observable by others, not merely subjective feelings of restlessness or being slowed down)

(6) fatigue or loss of energy nearly every day (7) feelings of worthlessness or excessive or inappropriate guilt (which may be delusional) nearly every day (not merely self-reproach or guilt about being sick)

(8) diminished ability to think or concentrate, or indecisiveness, nearly every day (either by subjective account or as observed by others)

(9) recurrent thoughts of death (not just fear of dying), recurrent suicidal ideation without a specific plan, or a suicide attempt or a specific plan for committing suicide In addition, the symptoms do not meet criteria for a Mixed Episode. The symptoms cause clinically significant distress or impairment in social, occupational, or other important areas of functioning. The symptoms are not due to the direct physiological effects of a substance (e.g., a drug of abuse, a medication) or a general medical condition (e.g., hypothyroidism).

The symptoms are not better accounted for by Bereavement, i.e., after the loss of a loved one, the symptoms persist for longer than 2 months, or are characterized by marked functional impairment, morbid preoccupation with worthlessness, suicidal ideation, psychotic symptoms, or psychomotor retardation.

B. Criteria for Manic Episode

A manic episode is a distinct period of abnormally and persistently elevated, expansive, or irritable mood, lasting at least one week (or any duration, if hospitalization is necessary).

During the period of mood disturbance, three (or more) of the following symptoms have persisted (four if the mood is only irritable) and have been present to a significant degree:

(1) inflated self-esteem or grandiosity (2) decreased need for sleep (e.g., feels rested after only 3 hours of sleep)

(3) more talkative than usual or pressure to keep talking (4) flight of ideas or subjective experience that thoughts are racing (5) distractibility (i.e., attention too easily drawn to unimportant or irrelevant external stimuli)

(6) increase in goal-directed activity (either socially, at work or school, or sexually) or psychomotor agitation (7) excessive involvement in pleasurable activities that have a high potential for painful consequences (e.g., engaging in unrestrained buying sprees, sexual indiscretions, or foolish business investments)

The symptoms do not meet criteria for a Mixed Episode. The mood disturbance is sufficiently severe to cause marked impairment in occupational functioning or in usual social activities or relationships with others, or to necessitate hospitalization to prevent harm to self or others, or there are psychotic features. The symptoms are not due to the direct physiological effects of a substance (e.g., a drug of abuse, a medication, or other treatment) or a general medical condition (e.g., hyperthyroidism).

C. Criteria for Mixed Episode

A mixed episode occurs when the criteria are met both for a Manic Episode and for a Major Depressive Episode (except for duration) nearly every day during at least a 1-week period. The mood disturbance is sufficiently severe to cause marked impairment in occupational functioning or in usual social activities or relationships with others, or to necessitate hospitalization to prevent harm to self or others, or there are psychotic features.

The symptoms are not due to the direct physiological effects of a substance (e.g., a drug of abuse, a medication, or other treatment) or a general medical condition (e.g., hyperthyroidism).

D. Criterion A of SZ

See above.

E. Types of SD

The type of SD may be may be specifiable, as either Bipolar Type, if the disturbance includes a Manic or a Mixed Episode (or a Manic or a Mixed Episode and Major Depressive Episodes), or Depressive Type, if the disturbance only includes Major Depressive Episodes.

F. Associated Features

Features associated with SD include Learning Problems, Hypoactivity, Psychotic, Euphoric Mood, Depressed Mood, Somatic/Sexual Dysfunction, Hyperactivity, Guilt/Obsession, Odd/Eccentric/Suspicious Personality, Anxious/Fearful/Dependent Personality, and Dramatic/Erratic/Antisocial Personality.

Schizotypal Personality Disorder (SPD)

Diagnostic Criteria for SPD

A diagnosis of SPD under the criteria of the DSM-IV is generally based on a pervasive pattern of social and interpersonal deficits marked by acute discomfort with, and reduced capacity for, close relationships as well as by cognitive or perceptual distortions and eccentricities of behavior, beginning by early adulthood and present in a variety of contexts, as indicated by five (or more) of the following:

(1) ideas of reference (excluding delusions of reference)

(2) odd beliefs or magical thinking that influences behavior and is (3) inconsistent with subcultural norms (e.g., superstitiousness, belief in clairvoyance, telepathy, or "sixth sense;" in children and adolescents, bizarre fantasies or preoccupations)

(4) unusual perceptual experiences, including bodily illusions (5) odd thinking and speech (e.g., vague, circumstantial, metaphorical, overelaborate, or stereotyped)

(6) suspiciousness or paranoid ideation (7) inappropriate or constricted affect (8) behavior or appearance that is odd, eccentric, or peculiar (9) lack of close friends or confidants other than first-degree relatives

(10) excessive social anxiety that does not diminish with familiarity and tends to be associated with paranoid fears rather than negative judgments about self SPD is diagnosed if the symptoms do not occur exclusively during the course of SZ, a Mood Disorder With Psychotic Features, another Psychotic Disorder, or a Pervasive Developmental Disorder, and the disturbance is not due to the direct physiological effects of a substance (e.g., a drug of abuse, a medication) or a general medical condition.

Associated features of SPD include Depressed Mood and Odd/Eccentric/Suspicious Personality.

Psychiatric Endophenotypes in SZ

A number of endophenotypes, i.e., intermediate phenotypes, that may more closely reflect biological mechanisms behind SZ, have been suggested, such as prepulse inhibition, structural abnormalities evident in MRI scans, specific domains of cognition (e.g., executive function), fine motor performance, working memory, etc.

Endophenotypes can also include clinical manifestations such as hallucinations, paranoia, mania, depression, obsessive-compulsive symptoms, etc., as well as response or lack of response to drugs and comorbidity for substance and alcohol abuse. See, e.g., Kendler et al., Am J Psychiatry 152(5): 749-54 (1995); Gottesman and Gould, Am J Psychiatry 160 (4):636-45 (2003); Cadenhead, Psychiatric Clinics of North America. 25(4):837-53 (2002); Gottesman and Gould, American Journal of Psychiatry. 160(4):636-45 (2003); Heinrichs, Neuroscience & Biobehavioral Reviews. 28(4):379-94 (2004); and Zobel and Maier, Nervenarzt. 75(3):205-14 (2004). There is now evidence that some candidate genes that were identified using DSM-IV type categorical definitions for "affected" individuals may influence specific endophenotypes, see, e.g., Baker et al., Biol Psychiatry 58(1):23-31 (2005); Cannon et al., Arch Gen Psychiatry 62(11):1205-13 (2005); Gothelf et al., Nat Neurosci 8(11):1500-2 (2005); Hallmayer et al., Am J Hum Genet 77(3):468-76 (2005); Callicott et al., Proc Natl Acad Sci USA 102(24):8627-32 (2005); Gornick et al., J Autism Dev Disord 1-8 (2005). Thus, the methods described herein can be used to associate haplotypes with specific psychiatric endophenotypes.

Positive and Negative Syndrome Scale (PANSS)

The Positive and Negative Syndrome Scale (PANSS) is a comprehensive psychometric scale used to classify psychopathology for severe neuropsychiatric diseases, including SZ. It measures a number of psychiatric endophenotypes or dimensions using quantitative scales based on the scoring of patients by clinicians. It is widely used to classify patients into specific subtypes, and is commonly used for measuring the improvement of symptoms in response to clinical interventions (Kay et al., Schizophr. Bull. 13:261-276 (1987); Kay et al., Br. J. Psychiatry Suppl 59-67 (1989); Leucht et al., Schizophr. Res. 79:231-238 (2005)).

Detailed information on PANSS and Scoring Criteria can be found in the art, e.g., on the world wide web at panss.org, or in the book by Kay, *Positive and Negative Syndromes in Schizophrenia*, (Routledge, 1991) which is incorporated herein in its entirety by reference. Based on these sources, the methodology is summarized briefly below.

PANSS comprises 30 individual subscales. Seven constitute a Positive Symptom Scale, seven the Negative Symptom Scale, and the remaining 16 items make up a General Psychopathology Scale. The scores for these scales are arrived at by summation of ratings across component items. Therefore, the potential ranges are 7 to 49 for the Positive and Negative Scales, and 16 to 112 for the General Psychopathology Scale (Source: The PANSS Institute).

Each of the 30 items is accompanied by a specific definition as well as detailed anchoring criteria for all seven rating points. These seven points represent increasing levels of psychopathology, as follows:

1—absent
2—minimal
3—mild
4—moderate
5—moderate severe
6—severe
7—extreme

The PANSS Individual subscales are described below.

P1. DELUSIONS—Beliefs which are unfounded, unrealistic and idiosyncratic.

P2. CONCEPTUAL DISORGANISATION—Disorganized process of thinking characterized by disruption of goal-directed sequencing, e.g., circumstantiality, loose associations, tangentiality, gross illogicality or thought block.

P3. HALLUCINATORY BEHAVIOUR—Verbal report or behaviour indicating perceptions which are not generated by external stimuli. These may occur in the auditory, visual, olfactory or somatic realms.

P4. EXCITEMENT—Hyperactivity as reflected in accelerated motor behaviour, heightened responsivity to stimuli, hypervigilance or excessive mood lability.

P5. GRANDIOSITY—Exaggerated self-opinion and unrealistic convictions of superiority, including delusions of extraordinary abilities, wealth, knowledge, fame, power and moral righteousness.

P6. SUSPICIOUSNESS/PERSECUTION—Unrealistic or exaggerated ideas of persecution, as reflected in guardedness, ad distrustful attitude, suspicious hypervigilance or frank delusions that others mean harm.

P7. HOSTILITY—Verbal and nonverbal expressions of anger and resentment, including sarcasm, passive-aggressive behavior, verbal abuse and assualtiveness.

N1. BLUNTED AFFECT—Diminished emotional responsiveness as characterized by a reduction in facial expression, modulation of feelings and communicative gestures.

N2. EMOTIONAL WITHDRAWAL—Lack of interest in, involvement with, and affective commitment to life's events.

N3. POOR RAPPORT—Lack of interpersonal empathy, openness in conversation and sense of closeness, interest or involvement with the interviewer. This is evidenced by interpersonal distancing and reduced verbal and nonverbal communication.

N4. PASSIVE/APATHETIC SOCIAL WITHDRAWAL—Diminished interest and initiative in social interactions due to passivity, apathy, anergy or avolition. This leads to reduced interpersonal involvements and neglect of activities of daily living.

N5. DIFFICULTY IN ABSTRACT THINKING—Impairment in the use of the abstract-symbolic mode of thinking, as evidenced by difficulty in classification, forming generalizations and proceeding beyond concrete or egocentric thinking in problem-solving tasks.

N6. LACK OF SPONTANEITY AND FLOW OF CONVERSATION—Reduction in the normal flow of communication associated with apathy, avolition, defensiveness or cognitive deficit. This is manifested by diminished fluidity and productivity of the verbal interactional process.

N7. STEREOTYPED THINKING—Decreased fluidity, spontaneity and flexibility of thinking, as evidenced in rigid, repetitious or barren thought content.

G1. SOMATIC CONCERN—Physical complaints or beliefs about bodily illness or malfunctions. This may range from a vague sense of ill being to clear-cut delusions of catastrophic physical disease.

G2. ANXIETY—Subjective experience of nervousness, worry, apprehension or restlessness, ranging from excessive concern about the present or future to feelings of panic.

G3. GUILT FEELINGS—Sense of remorse or self-blame for real or imagined misdeeds in the past.

G4. TENSION—Overt physical manifestations of fear, anxiety, and agitation, such as stiffness, tremor, profuse sweating and restlessness.

G5. MANNERISMS AND POSTURING—Unnatural movements or posture as characterized be an awkward, stilted, disorganized, or bizarre appearance.

G6. DEPRESSION—Feelings of sadness, discouragement, helplessness and pessimism.

G7. MOTOR RETARDATION—Reduction in motor activity as reflected in slowing or lessening or movements and speech, diminished responsiveness of stimuli, and reduced body tone.

G8. UNCOOPERATIVENESS—Active refusal to comply with the will of significant others, including the interviewer, hospital staff or family, which may be associated with distrust, defensiveness, stubbornness, negativism, rejection of authority, hostility or belligerence.

G9. UNUSUAL THOUGHT CONTENT—Thinking characterized by strange, fantastic or bizarre ideas, ranging from those which are remote or atypical to those which are distorted, illogical and patently absurd.

G10. DISORIENTATION—Lack of awareness of one's relationship to the milieu, including persons, place and time, which may be due to confusion or withdrawal.

G11. POOR ATTENTION—Failure in focused alertness manifested by poor concentration, distractibility from internal and external stimuli, and difficulty in harnessing, sustaining or shifting focus to new stimuli.

G12. LACK OF JUDGEMENT AND INSIGHT—Impaired awareness or understanding of one's own psychiatric condition and life situation. This is evidenced by failure to recognize past or present psychiatric illness or symptoms, denial of need for psychiatric hospitalization or treatment, decisions characterized by poor anticipation or consequences, and unrealistic short-term and long-range planning G13. DISTURBANCE OF VOLITION—Disturbance in the willful initiation, sustenance and control of one's thoughts, behavior, movements and speech.

G14. POOR IMPULSE CONTROL—Disordered regulation and control of action on inner urges, resulting in sudden, unmodulated, arbitrary or misdirected discharge of tension and emotions without concern about consequences.

G15. PREOCCUPATION—Absorption with internally generated thoughts and feelings and with autistic experiences to the detriment of reality orientation and adaptive behavior.

G16. ACTIVE SOCIAL AVOIDANCE—Diminished social involvement associated with unwarranted fear, hostility, or distrust.

Use of PANSS Score for Differential Diagnosis

Each patient's disease manifestation and process is unique. PANSS provides a structured, objective way of describing the various aspects of psychopathology of a given patient. However, proper implementation of the PANSS requires highly trained personnel to conduct the assessment and to interpret the results, and there is potential for site to site variability, especially outside the research setting.

Each of the PANSS composite scales and subscales can be considered a clinical endophenotype. The ability to link genetic profiles to these clinical endophenotypes, as described in the examples, will enable clinicians to refine a patient's diagnosis and develop a personalized therapeutic strategy for each patient. For example, the "A" allele of rs4832524, located in the KCNS3 gene, is associated with lower Negative Symptom burden as shown in the regression analysis in Table 14. Another example is the "A" allele of rs9823803, located in the GADL1 gene, which is significantly associated with lower scores on the Grandiosity Subscale as shown in the regression analysis in Table 15. By identifying these genetic contributions to specific endophenotypes, the physician can create a personalized diagnosis and treatment regime for the patient.

Current Treatment of SZ

Subjects with SZ typically require acute treatment for psychotic exacerbations, and long-term treatment including maintenance and prophylactic strategies to sustain symptom improvement and prevent recurrence of psychosis. Subjects with schizoaffective disorder experience the symptoms of both SZ and affective disorder (manic and/or depressive), thus require the specific treatments for each disorder. Subjects with SPD sometimes require medication for acute psychotic episodes but are often treated using psychosocial methods. The methods described herein can include the administration of one or more accepted or experimental treatment modalities to a person identified as at risk of developing SZ, SPD, or a SD, based on the presence of a haplotype associated with SZ, SPD, or SD. Currently accepted treatments presently include both pharmacologic and psychosocial management, and occasionally electroconvulsive therapy (ECT).

Standard pharmacologic therapies for SZ and SD include the administration of one or more antipsychotic medications, which are typically antagonists acting at postsynaptic $D_2$ dopamine receptors in the brain. Antipsychotic medications include conventional, or first generation, antipsychotic agents, which are sometimes referred to as neuroleptics because of their neurologic side effects, and second generation antipsychotic agents, which are less likely to exhibit neuroleptic effects and have been termed atypical antipsychotics.

In some embodiments, the methods described herein include the administration of one or more antipsychotic medications to a person identified by a method described herein as being at risk of developing SZ. Antipsychotic medications substantially reduce the risk of relapse in the stable phase of illness. In some embodiments, the methods include the administration of a first generation antipsychotic medication at a dose that is around the "extrapyramidal symptom (EPS) threshold" (i.e., the dose that will induce extrapyramidal side effects, e.g., bradykinesia, rigidity, or dyskinesia, with minimal rigidity detectable on physical examination, and/or a second-generation antipsychotics at a dose that is therapeutic, yet below the EPS threshold.

Standard pharmacologic therapies for SD also include the administration of a combination of antidepressant, and anti-anxiety medication. Suitable antidepressants include serotonergic antidepressants, e.g., fluoxetine or trazodone. Suitable anxiolytics include benzodiazepines, e.g., lorazepam, clonazepam. Lithium can also be administered. Thus, in some embodiments, the methods can include the administration of one or more antidepressant and/or anti-anxiety medications to a person identified as at risk of developing SZ.

The methods can also include psychosocial and rehabilitation interventions, e.g., interventions that are generally accepted as therapeutically beneficial, e.g., cognitive-behavioral therapy for treatment-resistant positive psychotic symptoms; supportive, problem-solving, educationally oriented psychotherapy; family therapy and education programs aimed at helping patients and their families understand the patient's illness, reduce stress, and enhance coping capabilities; social and living skills training; supported employment programs; and/or the provision of supervised residential living arrangements.

Currently accepted treatments for SZ are described in greater detail in the *Practice Guideline for the Treatment of Patients With Schizophrenia*, American Psychiatric Association, Second Edition, American Psychiatric Association, 2004, which is incorporated herein by reference in its entirety.

Methods of Determining Treatment Regimens and Methods of Treating SZ

As described herein, the presence of certain haplotypes described herein has been correlated with an increased risk of developing or having SZ; in addition, haplotypes are described herein that are correlated with altered response to a treatment, e.g., a pharmacological treatment. An altered response can be, for example, a positive response (i.e., an improvement in one or more symptoms of the disease), negative response (worsening of one or more symptoms of the disease), no response, or the presence or absence of side effects. Thus, the new methods can also include selecting a treatment regimen for a subject determined to have SZ or to be at risk for developing SZ, based upon the absence or presence of a haplotype described herein. The determination of a treatment regimen can also be based upon the absence or presence of other risk factors associated with SZ, e.g., as described herein. Therefore, the methods of the invention can include selecting a treatment regimen for a subject having one or more risk factors for SZ, and having a haplotype described herein. The methods can also include administering a selected treatment regimen to a subject having, or at risk for developing, SZ, to thereby treat, prevent or delay further progression of the disease. A treatment regimen can include the administration of a selected antipsychotic medications to a subject identified as at risk of developing SZ, before the onset of any psychotic episodes. The medications can be selected based on the presence of a haplotype that is associated with, for example, positive response, or the absence of significant side effects.

As used herein, the term "treat" or "treatment" is defined as the application or administration of a treatment regimen, e.g., a therapeutic agent or modality, to a subject, e.g., a patient. The subject can be a patient having SZ a symptom of SZ or at risk of developing (i.e., a predisposition toward) SZ. The treatment can be to cure, heal, alleviate, relieve, alter, remedy, ameliorate, palliate, improve or affect SZ, the symptoms of SZ or the predisposition toward SZ.

The methods described herein, e.g., methods of determining a treatment regimen and methods of treatment or prevention of SZ can further include the step of monitoring the subject, e.g., for a change (e.g., an increase or decrease) in one or more of the diagnostic criteria for SZ listed herein, or any other parameter related to clinical outcome. The subject can be monitored in one or more of the following periods: prior to beginning of treatment; during the treatment; or after one or more elements of the treatment have been administered. Monitoring can be used to evaluate the need for further treatment with the same or a different therapeutic agent or modality. Generally, a decrease in one or more of the parameters described above is indicative of the improved condition of the subject, although with red blood cell and platelet levels, an increase can be associated with the improved condition of the subject.

The methods can be used, e.g., to evaluate the suitability of, or to choose between alternative treatments, e.g., a particular dosage, mode of delivery, time of delivery, inclusion of adjunctive therapy, e.g., administration in combination with a second agent, or generally to determine the subject's probable drug response genotype. In a preferred embodiment, a treatment for SZ can be evaluated by administering the same treatment or combinations or treatments to a subject having SZ and a haplotype as described herein and to a subject that has SZ but does not have a haplotype as described herein. The effects of the treatment or combination of treatments on each of these subjects can be used to determine if a treatment or combination of treatments is particularly effective on a subgroup of subjects having SZ. In other embodiments, various treatments or combinations of treatments can be evaluated by administering two different treatments or combinations of treatments to at least two different subjects having SZ, and a haplotype as described herein. Such methods can be used to determine if a particular treatment or combination of treatments is more effective than others in treating this subset of SZ patients.

Various treatment regimens are known for treating SZ, e.g., as described herein.

Pharmacogenomics

With regards to both prophylactic and therapeutic methods of treatment of SZ, such treatments may be specifically tailored or modified, based on knowledge obtained from the field of pharmacogenomics. "Pharmacogenomics," as used herein, refers to the application of genomics technologies such as structural chromosomal analysis, to drugs in clinical development and on the market. See, for example, Eichelbaum et al., Clin. Exp. Pharmacol. Physiol. 23:983-985 (1996) and Linder et al., Clin. Chem. 43:254-266 (1997). Specifically, as used herein, the term refers the study of how a patient's genes determine his or her response to a drug (e.g., a patient's "drug response phenotype," or "drug response genotype"). Thus, another aspect of the invention provides methods for tailoring an individual's prophylactic or therapeutic treatment according to that individual's drug response genotype.

Information generated from pharmacogenomic research using a method described herein can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when administering a therapeutic composition, e.g., a cytotoxic agent or combination of cytotoxic agents, to a patient, as a means of treating or preventing SZ.

In one embodiment, a physician or clinician may consider applying knowledge obtained in relevant pharmacogenomics studies, e.g., using a method described herein, when determining whether to administer a pharmaceutical composition, e.g., an antipsychotic agent or a combination of antipsychotic agents, to a subject. In another embodiment, a physician or clinician may consider applying such knowledge when determining the dosage, e.g., amount per treatment or frequency of treatments, of a treatment, e.g., a antipsychotic agent or combination of antipsychotic agents, administered to a patient.

As one example, a physician or clinician may determine (or have determined, e.g., by a laboratory) the haplotype of a subject as described herein, and optionally one or more other markers associated with SZ of one or a group of subjects who may be participating in a clinical trial, wherein the subjects have SZ, and the clinical trial is designed to test the efficacy of a pharmaceutical composition, e.g., an antipsychotic or combination of antipsychotic agents, and wherein the physician or clinician attempts to correlate the genotypes of the subjects with their response to the pharmaceutical composition.

As another example, information regarding a haplotype associated with an altered pharmacogenomic response for SZ as described herein, can be used to stratify or select a subject population for a clinical trial. The information can, in some embodiments, be used to stratify individuals that may exhibit a toxic response to a treatment from those that will not. In other cases, the information can be used to separate those that are more likely to be non-responders from those who will be responders. The haplotypes described herein can be used in pharmacogenomics-based design and to manage the conduct of a clinical trial, e.g., as described in U.S. Pat. Pub. No. 2003/0108938.

As another example, information regarding a haplotype associated with an increased risk of SZ, or with altered pharmacogenomic response for SZ, as described herein, can be used to stratify or select human cells or cell lines for drug testing purposes. Human cells are useful for studying the effect of a polymorphism on physiological function, and for identifying and/or evaluating potential therapeutic agents for the treatment of SZ e.g., anti-psychotics. Thus the methods can include performing the present methods on genetic material from a cell line. The information can, in some embodiments, be used to separate cells that respond particular drugs from those that do not respond, e.g. which cells show altered second messenger signaling.

Theranostics

Also included herein are compositions and methods for the identification and treatment of subjects who have an increased risk of SZ, or altered clinical presentation of SZ, such that a theranostic approach can be taken to test such individuals to determine the effectiveness of a particular therapeutic intervention (e.g., a pharmaceutical or non-pharmaceutical intervention as described herein) and to alter the intervention to 1) reduce the risk of developing adverse outcomes and 2) enhance the effectiveness of the intervention. Thus, in addition to diagnosing or confirming the predisposition to SZ, the methods and compositions described herein also provide a means of optimizing the treatment of a subject having SZ. Provided herein is a theranostic approach to treating and preventing SZ, by integrating diagnostics and therapeutics to improve the real-time treatment of a subject. Practically, this means creating tests that can identify which patients are most suited to a particular therapy, and providing feedback on how well a drug is working to optimize treatment regimens.

Within the clinical trial setting, a theranostic method or composition of the invention can provide key information to optimize trial design, monitor efficacy, and enhance drug safety. For instance, "trial design" theranostics can be used for patient stratification, determination of patient eligibility (inclusion/exclusion), creation of homogeneous treatment groups, and selection of patient samples that are representative of the general population. Such theranostic tests can therefore provide the means for patient efficacy enrichment, thereby minimizing the number of individuals needed for trial recruitment. "Efficacy" theranostics are useful for monitoring therapy and assessing efficacy criteria. Finally, "safety" theranostics can be used to prevent adverse drug reactions or avoid medication error.

The methods described herein can include retrospective analysis of clinical trial data as well, both at the subject level and for the entire trial, to detect correlations between a haplotype as described herein and any measurable or quantifiable parameter relating to the outcome of the treatment, e.g., efficacy (the results of which may be binary (i.e., yes and no) as well as along a continuum), side-effect profile (e.g., weight gain, metabolic dysfunction, lipid dysfunction, movement disorders, or extrapyramidal symptoms), treatment maintenance and discontinuation rates, return to work status, hospitalizations, suicidality, total healthcare cost, social functioning scales, response to non-pharmacological treatments, and/or dose response curves. The results of these correlations can then be used to influence decision-making, e.g., regarding treatment or therapeutic strategies, provision of services, and/or payment. For example, a correlation between a positive outcome parameter (e.g., high efficacy, low side effect profile, high treatment maintenance/low discontinuation rates, good return to work status, low hospitalizations, low suicidality, low total healthcare cost, high social function scale, favorable response to non-pharmacological treatments, and/or acceptable dose response curves) and a selected haplotype can influence treatment such that the treatment is recommended or selected for a subject having the selected haplotype.

Kits

Also within the scope of the invention are kits comprising a probe that hybridizes with a region of human chromosome as described herein and can be used to detect a polymorphism described herein. The kit can include one or more other elements including: instructions for use; and other reagents, e.g., a label, or an agent useful for attaching a label to the probe. Instructions for use can include instructions for diagnostic applications of the probe for assessing risk of SZ in a method described herein. Other instructions can include instructions for attaching a label to the probe, instructions for performing in situ analysis with the probe, and/or instructions for obtaining a sample to be analyzed from a subject. As discussed above, the kit can include a label, e.g., any of the labels described herein. In some embodiments, the kit includes a labeled probe that hybridizes to a region of human chromosome as described herein, e.g., a labeled probe as described herein.

The kit can also include one or more additional probes that hybridize to the same chromosome, e.g., chromosome 1, 3, 6, 10, 11, 12, 13, 14, 15, 15, 17, 18, 19, or 20, or another chromosome or portion thereof that can have an abnormality associated with risk for SZ. For example, the additional probe or probes can be: a probe that hybridizes to human chromosome 22q11-12 or a portion thereof, (e.g., a probe that detects a sequence associated with SZ or BD in this region of chromosome 22), or probes that hybridize to all or a portion of 22q12.3 (e.g., near D22S283), 22q11.2, 22q11.2, 22q11-q13, 1q42.1, 1q42.1, 1q21-q22, 2p, 2q, 3p25, 4p, 4q, 5q11.2-q13.3, 6p22.3, 6p23, 6q13-q26, 7q, 8p12-21, 8q, 9q, 10p-15-p13 (e.g., near D10S189), 10q22.3, 11q14-q21, 12q24, 13q34, 13q32, 14q32.3, 15q15, 16p, 17q, 18p, 18q, 19p. 20p, 21q, Xq, and/or the X/Y pseudoautosomal region. A kit that includes additional probes can further include labels, e.g., one or more of the same or different labels for the probes. In other embodiments, the additional probe or probes provided with the kit can be a labeled probe or probes. When the kit further includes one or more additional probe or probes, the kit can further provide instructions for the use of the additional probe or probes.

Kits for use in self-testing can also be provided. For example, such test kits can include devices and instructions that a subject can use to obtain a sample, e.g., of buccal cells or blood, without the aid of a health care provider. For example, buccal cells can be obtained using a buccal swab or brush, or using mouthwash.

Kits as provided herein can also include a mailer, e.g., a postage paid envelope or mailing pack, that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms, e.g., the test requisition form, and the container holding the sample, can be coded, e.g., with a bar code, for identifying the subject who provided the sample.

Databases

Also provided herein are databases that include a list of polymorphisms as described herein, and wherein the list is largely or entirely limited to polymorphisms identified as useful in performing genetic diagnosis of or determination of susceptibility to SZ as described herein. The list is stored, e.g., on a flat file or computer-readable medium. The databases can further include information regarding one or more subjects, e.g., whether a subject is affected or unaffected, clinical information such as endophenotype, age of onset of symptoms, any treatments administered and outcomes (e.g., data relevant to pharmacogenomics, diagnostics or theranostics), and other details, e.g., about the disorder in the subject, or environmental or other genetic factors. The databases can be used to detect correlations between a particular haplotype and the information regarding the subject, e.g., to detect correlations between a haplotype and a particular endophenotype, or treatment response.

Engineered Cells

Also provided herein are engineered cells that harbor one or more polymorphism described herein, e.g., one or more polymorphisms that constitute a haplotype associated with SZ, altered drug response or a specific endophenotype. Such cells are useful for studying the effect of a polymorphism on physiological function, and for identifying and/or evaluating potential therapeutic agents for the treatment of SZ-spectrum disorders e.g., anti-psychotics.

As one example, included herein are cells in which one of the various alleles of the genes described herein has be recreated that is associated with an increased risk of SZ. Methods are known in the art for generating cells, e.g., by homologous recombination between the endogenous gene and an exogenous DNA molecule introduced into a cell, e.g., a cell of an animal. In some embodiments, the cells can be used to generate transgenic animals using methods known in the art.

The cells are preferably mammalian cells, e.g., neuronal type cells, in which an endogenous gene has been altered to include a polymorphism as described herein. Techniques such as targeted homologous recombinations, can be used to insert the heterologous DNA as described in, e.g., Chappel, U.S. Pat. No. 5,272,071; WO 91/06667, published in May 16, 1991.

EXAMPLES

The invention is further described in the following examples, which do not limit the scope of the invention described in the claims.

Example 1

Novel Markers Associated with SZ

The Clinical Antipsychotic Trials of Intervention Effectiveness (CATIE), a large federally funded clinical trial designed to assess the efficacy of antipsychotics in a real world setting, is a valuable resource for determining the role of genes in drug response (Stroup et al., Schizophr. Bull. 29:15-31 (2003); Lieberman et al., N. Engl. J. Med. 353: 1209-1223 (2005)). As part of the CATIE trial, SNP genotyping was performed for roughly half of the trial participants (Sullivan et al., Mol. Psychiatry 13:570-584 (2008)). When combined with disease status, PANSS scores, and clinical drug response data, the genotyping data allows the identification of genetic variants (e.g., SNPs) that are statistically associated with increased risk of developing SZ.

The design of the CATIE study has been described in detail by others (see, e.g., Stroup et al., Schizophr. Bull. 29:15-31 (2003); Lieberman et al., N. Engl. J. Med. 353:1209-1223 (2005)). Briefly, 1460 subjects were randomly assigned one of several antipsychotics and those who did not respond or chose to quit their current medication were re-randomized to another drug. Details regarding SNP genotyping and quality control have been recently published (Sullivan et al., Mol. Psychiatry 13:570-584 (2008)).

Genotype and phenotype data for the CATIE trial were made available to qualified researchers through the NIMH Center for Collaborative Genetic Studies on Mental Disorders. Data for 417 patients with schizophrenia and 419 unaffected controls self reported as having exclusively European ancestry were evaluated. This same patient population was described in a recent study by Sullivan and coworkers, which confirmed that there is no hidden stratification in the sample (Sullivan et al., Mol. Psychiatry 13:570-584 (2008)).

In addition, for this example, genotyping and phenotype data were obtained from the Genetic Analysis Information Network (GAIN) Database found at ncbi.nlm.nih.gov through dbGaP, at accession number PHS000017.v1.p1. Genotypes and associated phenotype data for the GAIN Genome-Wide Association Study of Schizophrenia were provided by P. Gejman, and genotyping of these samples was provided through the Genetic Association Information Network (GAIN). Data for 1172 cases and 1378 controls with Caucasian ancestry were evaluated for the GAIN sample.

For both the CATIE and GAIN studies, individual cases were diagnosed as having SZ based on DSM-III/IV criteria.

Statistical Methods:

Genetic analysis to document the influence of haplotypes on SZ risk was performed using the PLINK 1.03 whole genome analysis toolset developed by Purcell and coworkers (Purcell et al., Am. J. Hum. Genet. 81:559-575 (2007)). PLINK calculates P values for the allele-specific chi-squared test and the odds ratio (OR; or relative risk) associated with the minor allele.

Confirmation of Novel Markers Associated with SZ Risk:

Table 1 provides numerous examples of SNP-based alleles that influence SZ risk. Table 1 reports the minor allele frequencies, P values, and ORs for numerous SNPs, in Tables B and C, that affect SZ risk. ORs of >1.0 indicate that the minor SNP allele is associated with greater susceptibility, and ORs of <1.0 indicate that the minor SNP allele is associated with decreased susceptibility to SZ.

Note in Table 1 that haplotype blocks result in the same Test SNP being in linkage disequilibrium with multiple SNPs in Table B. Similarly, haplotype blocks result in multiple Test SNPs that can be used for each SNP listed in Table B, though such redundant examples are not presented in Table 1, unless the test SNP was evaluated in both the CATIE and GAIN samples.

TABLE 1

Confirmation of Novel Markers Associated with SZ risk

| Gene Name | Table B SNP | Test SNP in linkage disequilibrium | r² | Allele | Frequency in Cases | P | OR | Study |
| --- | --- | --- | --- | --- | --- | --- | --- | --- |
| CAMTA1 | rs10864639 | rs1542899 | 1.00 | C | 0.086 | 0.008304 | 0.78 | GAIN |
| CAMTA1 | rs845197 | rs2097518 | 0.71 | C | 0.249 | 0.02548 | 0.87 | GAIN |
| CAMTA1 | rs2071986 | rs9919223 | 1.00 | T | 0.267 | 0.0347 | 0.88 | GAIN |
| RERE | rs12136689 | rs10779702 | 0.76 | A | 0.355 | 0.006746 | 1.18 | GAIN |
| RERE | rs8627 | rs10779702 | 0.52 | A | 0.355 | 0.006746 | 1.18 | GAIN |
| RP1-21O18.1 | rs7546786 | rs7546786 | N/A | C | 0.211 | 0.0356 | 0.78 | CATIE |
| RP1-21O18.1 | rs2073091 | rs761288 | 0.69 | C | 0.269 | 0.04654 | 1.14 | GAIN |
| RP1-21O18.1 | rs4661572 | rs761288 | 0.56 | C | 0.269 | 0.04654 | 1.14 | GAIN |
| RP1-21O18.1 | rs12057431 | rs10803343 | 1.00 | C | 0.016 | 0.03243 | 3.20 | CATIE |
| KCND3 | rs4838924 | rs1373291 | 0.86 | T | 0.224 | 0.04121 | 1.28 | CATIE |

TABLE 1-continued

Confirmation of Novel Markers Associated with SZ risk

| Gene Name | Table B SNP | Test SNP in linkage disequilibrium | r² | Allele | Frequency in Cases | P | OR | Study |
|---|---|---|---|---|---|---|---|---|
| VAMP4 | rs10913530 | rs9943293 | 1.00 | T | 0.311 | 0.01885 | 1.29 | CATIE |
| VAMP4 | rs12096984 | rs9943293 | 1.00 | T | 0.311 | 0.01885 | 1.29 | CATIE |
| VAMP4 | rs2073484 | rs9943293 | 1.00 | T | 0.311 | 0.01885 | 1.29 | CATIE |
| VAMP4 | rs6672082 | rs9943293 | 1.00 | T | 0.311 | 0.01885 | 1.29 | CATIE |
| VAMP4 | rs15655 | rs10913529 | 1.00 | C | 0.182 | 0.00696 | 0.83 | GAIN |
| DNM3 | rs2093184 | rs7540873 | 0.62 | T | 0.282 | 0.03038 | 0.88 | GAIN |
| DNM3 | rs7554526 | rs7540873 | 0.61 | T | 0.282 | 0.03038 | 0.88 | GAIN |
| DNM3 | rs9425287 | rs10158839 | 1.00 | C | 0.513 | 0.04037 | 1.12 | GAIN |
| FASLG | rs10458360 | rs10458360 | N/A | G | 0.474 | 0.02088 | 1.14 | GAIN |
| FASLG | rs12135884 | rs10458360 | 0.56 | G | 0.474 | 0.02088 | 1.14 | GAIN |
| CACNA1E | rs553042 | rs553042 | N/A | A | 0.304 | 0.006968 | 1.18 | GAIN |
| CACNA1E | rs17494681 | rs17494681 | N/A | A | 0.188 | 0.01055 | 1.21 | GAIN |
| CACNA1E | rs506947 | rs7554158 | 1.00 | A | 0.109 | 0.01115 | 0.80 | GAIN |
| CACNA1E | rs638132 | rs546191 | 0.67 | T | 0.193 | 0.01582 | 0.75 | CATIE |
| CAMK1G | rs6690557 | rs9429821 | 0.69 | C | 0.317 | 0.04072 | 0.88 | GAIN |
| SYT14 | rs9429830 | rs7543650 | 0.52 | T | 0.236 | 0.02059 | 0.77 | CATIE |
| SYT14 | rs9429830 | rs227193 | 0.90 | G | 0.400 | 0.0183 | 0.87 | GAIN |
| KCNH1 | rs1770220 | rs1340127 | 0.51 | G | 0.437 | 0.01888 | 0.87 | GAIN |
| ANK3 | rs1050745 | rs1050745 | N/A | T | 0.209 | 0.02123 | 0.86 | GAIN |
| ANK3 | rs2393607 | rs1078534 | 0.82 | C | 0.173 | 0.01647 | 0.74 | CATIE |
| ANK3 | rs11596260 | rs11596260 | N/A | T | 0.351 | 0.03773 | 0.89 | GAIN |
| ANK3 | rs2241540 | rs11596260 | 1.00 | T | 0.351 | 0.03773 | 0.89 | GAIN |
| ANK3 | rs1551684 | rs1551683 | 1.00 | T | 0.114 | 0.0462 | 0.75 | CATIE |
| KCNQ1 | rs2283174 | rs2283179 | 0.52 | C | 0.132 | 0.04204 | 1.19 | GAIN |
| KCNQ1 | rs231348 | rs10832405 | 0.80 | A | 0.126 | 0.0203 | 1.45 | CATIE |
| RHOG | rs11030008 | rs1869002 | 0.67 | G | 0.312 | 0.007693 | 1.34 | CATIE |
| USH1C | rs2237965 | rs1076311 | 0.63 | G | 0.472 | 0.03922 | 1.23 | CATIE |
| USH1C | rs10766408 | rs2237959 | 0.53 | G | 0.454 | 0.01149 | 1.29 | CATIE |
| USH1C | rs2041027 | rs10766410 | 0.54 | A | 0.461 | 0.0002016 | 1.45 | CATIE |
| USH1C | rs2237957 | rs10766410 | 0.62 | A | 0.461 | 0.0002016 | 1.45 | CATIE |
| OTOG | rs10766410 | rs10766410 | N/A | A | 0.461 | 0.0002016 | 1.45 | CATIE |
| OTOG | rs2073582 | rs10766410 | 0.55 | A | 0.461 | 0.0002016 | 1.45 | CATIE |
| SERGEF | rs4757589 | rs4757589 | N/A | G | 0.497 | 0.001605 | 1.19 | GAIN |
| NAV2 | rs10766590 | rs10500860 | 0.59 | G | 0.308 | 0.02614 | 1.15 | GAIN |
| NAV2 | rs2042600 | rs1559665 | 0.93 | T | 0.480 | 0.02766 | 0.88 | GAIN |
| NAV2 | rs2278132 | rs1559665 | 0.87 | T | 0.480 | 0.02766 | 0.88 | GAIN |
| NAV2 | rs7119267 | rs7119267 | N/A | C | 0.346 | 0.02078 | 1.15 | GAIN |
| NAV2 | rs2028570 | rs2255677 | 0.58 | A | 0.441 | 0.01665 | 1.15 | GAIN |
| NAV2 | rs2289566 | rs10732471 | 0.57 | A | 0.227 | 0.009299 | 0.84 | GAIN |
| SLC17A6 | rs11026532 | rs1155331 | 0.96 | T | 0.265 | 0.02007 | 0.86 | GAIN |
| LRRC4C | rs1551833 | rs4237678 | 0.54 | C | 0.188 | 0.002021 | 1.26 | GAIN |
| LRRC4C | rs10837367 | rs1377106 | 1.00 | A | 0.067 | 0.00126 | 0.57 | CATIE |
| HSD17B12 | rs1061810 | rs7116641 | 0.54 | G | 0.346 | 0.02577 | 1.27 | CATIE |
| HSD17B12 | rs4755744 | rs7116641 | 0.65 | G | 0.346 | 0.02577 | 1.27 | CATIE |
| HSD17B12 | rs10838160 | rs10838166 | 1.00 | G | 0.383 | 0.003094 | 0.75 | CATIE |
| HSD17B12 | rs3802891 | rs10838166 | 1.00 | G | 0.383 | 0.003094 | 0.75 | CATIE |
| PHACS | rs16937817 | rs7950395 | 0.58 | A | 0.141 | 0.00271 | 1.29 | GAIN |
| PHACS | rs7950395 | rs7950395 | N/A | A | 0.141 | 0.00271 | 1.29 | GAIN |
| SYT13 | rs12362429 | rs7124508 | 0.64 | A | 0.425 | 0.02358 | 0.88 | GAIN |
| SYT13 | rs11038382 | rs1077491 | 1.00 | T | 0.290 | 0.0195 | 0.78 | CATIE |
| SYT13 | rs2863182 | rs1077491 | 0.84 | T | 0.290 | 0.0195 | 0.78 | CATIE |
| SYT13 | rs4992029 | rs1077491 | 0.61 | T | 0.290 | 0.0195 | 0.78 | CATIE |
| SYT13 | rs12362429 | rs7118408 | 0.70 | G | 0.419 | 0.01028 | 0.78 | CATIE |
| ZFP91-CNTF | rs1938596 | rs2509920 | 0.97 | G | 0.404 | 0.01056 | 0.86 | GAIN |
| ZFP91-CNTF | rs4319530 | rs2509920 | 0.90 | G | 0.404 | 0.01056 | 0.86 | GAIN |
| ZFP91-CNTF | rs7945889 | rs948562 | 0.95 | G | 0.160 | 0.04957 | 0.86 | GAIN |
| ZFP91-CNTF | rs948562 | rs948562 | N/A | G | 0.160 | 0.04957 | 0.86 | GAIN |
| DTX4 | rs1048444 | rs3847 | 1.00 | A | 0.353 | 0.01537 | 0.87 | GAIN |
| DTX4 | rs2211912 | rs3847 | 0.77 | A | 0.353 | 0.01537 | 0.87 | GAIN |
| DTX4 | rs3847 | rs3847 | N/A | A | 0.353 | 0.01537 | 0.87 | GAIN |
| DTX4 | rs5029315 | rs3847 | 0.77 | A | 0.353 | 0.01537 | 0.87 | GAIN |
| DTX4 | rs544864 | rs3847 | 0.55 | A | 0.353 | 0.01537 | 0.87 | GAIN |
| DTX4 | rs621162 | rs3847 | 0.55 | A | 0.353 | 0.01537 | 0.87 | GAIN |
| DTX4 | rs656163 | rs3847 | 0.64 | A | 0.353 | 0.01537 | 0.87 | GAIN |
| KIAA1853 | rs1568923 | rs7298478 | 0.69 | G | 0.275 | 0.006263 | 0.84 | GAIN |
| KIAA1853 | rs7134748 | rs4767783 | 0.72 | A | 0.404 | 0.03728 | 1.13 | GAIN |
| KIAA1853 | rs7969288 | rs4767783 | 0.57 | A | 0.404 | 0.03728 | 1.13 | GAIN |
| KIAA1853 | rs7297606 | rs4075945 | 1.00 | T | 0.093 | 0.01915 | 1.27 | GAIN |
| RIMBP2 | rs4237817 | rs1877986 | 0.62 | A | 0.415 | 0.0264 | 0.80 | CATIE |
| CHFR | rs2306541 | rs7297261 | 0.96 | A | 0.315 | 0.04659 | 1.13 | GAIN |
| TTC5 | rs3737220 | rs4981948 | 1.00 | C | 0.175 | 0.006939 | 0.82 | GAIN |
| TTC5 | rs2318864 | rs4981951 | 0.52 | C | 0.185 | 0.01689 | 0.84 | GAIN |
| TTC5 | rs3742945 | rs4981951 | 0.52 | C | 0.185 | 0.01689 | 0.84 | GAIN |
| DACT1 | rs11541 | rs863091 | 1.00 | A | 0.202 | 0.04207 | 1.16 | GAIN |

TABLE 1-continued

Confirmation of Novel Markers Associated with SZ risk

| Gene Name | Table B SNP | Test SNP in linkage disequilibrium | $r^2$ | Allele | Frequency in Cases | P | OR | Study |
|---|---|---|---|---|---|---|---|---|
| DACT1 | rs160472 | rs863091 | 0.54 | A | 0.202 | 0.04207 | 1.16 | GAIN |
| DACT1 | rs863091 | rs863091 | N/A | A | 0.202 | 0.04207 | 1.16 | GAIN |
| DAAM1 | rs4127823 | rs12590850 | 0.61 | A | 0.416 | 0.02325 | 1.26 | CATIE |
| GPR135 | rs10138199 | rs1273156 | 0.81 | T | 0.459 | 0.02265 | 1.25 | CATIE |
| GPR135 | rs1253181 | rs1273156 | 1.00 | T | 0.459 | 0.02265 | 1.25 | CATIE |
| GPR135 | rs17255731 | rs1273156 | 0.62 | T | 0.459 | 0.02265 | 1.25 | CATIE |
| GPR135 | rs4898989 | rs1273156 | 0.81 | T | 0.459 | 0.02265 | 1.25 | CATIE |
| GPR135 | rs9323348 | rs1273156 | 0.81 | T | 0.459 | 0.02265 | 1.25 | CATIE |
| EML1 | rs2273704 | rs12590861 | 0.61 | G | 0.311 | 0.00485 | 1.19 | GAIN |
| EML1 | rs7143905 | rs12590861 | 0.70 | G | 0.311 | 0.00485 | 1.19 | GAIN |
| EML1 | rs746698 | rs11850280 | 0.91 | G | 0.190 | 0.008545 | 1.21 | GAIN |
| EML1 | rs11160553 | rs12435250 | 0.67 | G | 0.254 | 0.02602 | 0.87 | GAIN |
| EML1 | rs12433613 | rs12435250 | 0.56 | G | 0.254 | 0.02602 | 0.87 | GAIN |
| EML1 | rs6575751 | rs12435250 | 0.67 | G | 0.254 | 0.02602 | 0.87 | GAIN |
| EVL | rs3206354 | rs3206354 | N/A | T | 0.053 | 0.03254 | 1.33 | GAIN |
| HERC2 | rs11074322 | rs6497272 | 1.00 | G | 0.017 | 0.03882 | 2.82 | CATIE |
| HERC2 | rs1635168 | rs8041209 | 0.87 | T | 0.087 | 0.0183 | 1.57 | CATIE |
| HERC2 | rs2238289 | rs8041209 | 0.51 | T | 0.087 | 0.0183 | 1.57 | CATIE |
| HERC2 | rs7495174 | rs8041209 | 0.58 | T | 0.087 | 0.0183 | 1.57 | CATIE |
| HERC2 | rs11631797 | rs916977 | 0.86 | T | 0.195 | 0.03981 | 1.30 | CATIE |
| HERC2 | rs916977 | rs916977 | N/A | T | 0.195 | 0.03981 | 1.30 | CATIE |
| UNC13C | rs2115827 | rs12148800 | 0.97 | C | 0.470 | 0.02906 | 0.88 | GAIN |
| UNC13C | rs2163195 | rs2115825 | 0.57 | A | 0.501 | 0.02333 | 1.14 | GAIN |
| UNC13C | rs12594549 | rs934192 | 0.85 | T | 0.175 | 0.001305 | 1.28 | GAIN |
| UNC13C | rs1897069 | rs1897069 | N/A | C | 0.449 | 0.01113 | 0.87 | GAIN |
| UNC13C | rs12910912 | rs12900128 | 0.52 | G | 0.295 | 0.01764 | 1.16 | GAIN |
| UNC13C | rs11856476 | rs12917023 | 0.70 | G | 0.172 | 0.04217 | 1.17 | GAIN |
| NEDD4 | rs4424863 | rs4520787 | 0.90 | A | 0.397 | 0.03785 | 1.24 | CATIE |
| NEDD4 | rs8028559 | rs11630780 | 0.69 | C | 0.396 | 0.01945 | 0.79 | CATIE |
| NEDD4 | rs17238461 | rs2175104 | 0.53 | A | 0.108 | 0.03922 | 1.42 | CATIE |
| NEDD4 | rs1509408 | rs1509408 | N/A | C | 0.225 | 0.03142 | 0.78 | CATIE |
| AKAP13 | rs2291049 | rs16941653 | 0.59 | T | 0.070 | 0.01822 | 0.66 | CATIE |
| AKAP13 | rs338556 | rs2241266 | 1.00 | T | 0.071 | 0.0406 | 0.81 | GAIN |
| KLHL25 | rs2430838 | rs2241266 | 0.91 | T | 0.071 | 0.0406 | 0.81 | GAIN |
| SV2B | rs1075840 | rs2269799 | 0.72 | C | 0.325 | 0.004465 | 1.36 | CATIE |
| SV2B | rs1117388 | rs2269799 | 0.55 | C | 0.325 | 0.004465 | 1.36 | CATIE |
| SV2B | rs2301665 | rs2269799 | 0.59 | C | 0.325 | 0.004465 | 1.36 | CATIE |
| SV2B | rs8027498 | rs2269799 | 0.72 | C | 0.325 | 0.004465 | 1.36 | CATIE |
| SV2B | rs3743444 | rs2239994 | 0.50 | T | 0.113 | 0.01159 | 1.53 | CATIE |
| SLCO3A1 | rs12912997 | rs12905912 | 0.96 | A | 0.297 | 0.03912 | 0.81 | CATIE |
| IGF1R | rs4965436 | rs11634874 | 0.76 | C | 0.111 | 0.02439 | 1.46 | CATIE |
| IGF1R | rs11247380 | rs7165181 | 0.55 | G | 0.194 | 0.03684 | 0.78 | CATIE |
| IGF1R | rs1879613 | rs7165181 | 0.96 | G | 0.194 | 0.03684 | 0.78 | CATIE |
| N4BP1 | rs1039342 | rs8046716 | 0.61 | T | 0.500 | 0.003166 | 1.34 | CATIE |
| N4BP1 | rs1120276 | rs8046716 | 0.61 | T | 0.500 | 0.003166 | 1.34 | CATIE |
| N4BP1 | rs1224 | rs8046716 | 0.61 | T | 0.500 | 0.003166 | 1.34 | CATIE |
| N4BP1 | rs2354580 | rs8046716 | 1.00 | T | 0.500 | 0.003166 | 1.34 | CATIE |
| N4BP1 | rs3826176 | rs8046716 | 1.00 | A | 0.500 | 0.003166 | 1.34 | CATIE |
| N4BP1 | rs9937623 | rs8046716 | 0.59 | T | 0.500 | 0.003166 | 1.34 | CATIE |
| NDRG4 | rs13333449 | rs16960170 | 0.80 | G | 0.311 | 0.02137 | 1.15 | GAIN |
| NDRG4 | rs7202037 | rs16960170 | 0.67 | G | 0.311 | 0.02137 | 1.15 | GAIN |
| KIAA0182 | rs736845 | rs736845 | N/A | A | 0.310 | 0.0005682 | 1.24 | GAIN |
| KIAA0182 | rs9940601 | rs9940601 | N/A | A | 0.403 | 0.01452 | 1.15 | GAIN |
| KIAA0182 | rs3815794 | rs1053328 | 0.73 | A | 0.327 | 0.00984 | 0.86 | GAIN |
| KIAA0182 | rs3815794 | rs1053328 | 0.73 | T | 0.315 | 0.002786 | 0.74 | CATIE |
| C16orf74 | rs11644122 | rs11644122 | N/A | T | 0.293 | 0.03696 | 0.88 | GAIN |
| C16orf74 | rs2305357 | rs394623 | 0.55 | G | 0.403 | 0.0003797 | 1.23 | GAIN |
| C16orf74 | rs373835 | rs394623 | 0.68 | G | 0.403 | 0.0003797 | 1.23 | GAIN |
| C16orf74 | rs386061 | rs394623 | 0.68 | G | 0.403 | 0.0003797 | 1.23 | GAIN |
| PMP22 | rs13422 | rs230915 | 0.76 | C | 0.413 | 0.03188 | 1.13 | GAIN |
| PMP22 | rs230938 | rs230915 | 0.97 | C | 0.413 | 0.03188 | 1.13 | GAIN |
| PMP22 | rs231021 | rs230915 | 0.55 | C | 0.413 | 0.03188 | 1.13 | GAIN |
| FUSSEL18 | rs10502880 | rs8086549 | 0.85 | C | 0.473 | 0.04802 | 1.22 | CATIE |
| FUSSEL18 | rs17785419 | rs8086549 | 0.85 | C | 0.473 | 0.04802 | 1.22 | CATIE |
| FUSSEL18 | rs2668771 | rs8086549 | 0.64 | C | 0.473 | 0.04802 | 1.22 | CATIE |
| FUSSEL18 | rs7236105 | rs8086549 | 1.00 | C | 0.473 | 0.04802 | 1.22 | CATIE |
| SMAD2 | rs12457664 | rs1792670 | 0.85 | G | 0.445 | 0.039 | 0.89 | GAIN |
| SMAD2 | rs1787176 | rs1792670 | 0.97 | G | 0.445 | 0.039 | 0.89 | GAIN |
| SMAD2 | rs1792666 | rs1792670 | 0.71 | G | 0.445 | 0.039 | 0.89 | GAIN |
| SMAD2 | rs1792682 | rs1792670 | 0.94 | G | 0.445 | 0.039 | 0.89 | GAIN |
| SMAD2 | rs2000709 | rs1792670 | 0.84 | G | 0.445 | 0.039 | 0.89 | GAIN |
| SMAD2 | rs7228393 | rs1792670 | 0.91 | G | 0.445 | 0.039 | 0.89 | GAIN |
| KIAA0427 | rs2175565 | rs9952398 | 1.00 | C | 0.253 | 0.003642 | 1.41 | CATIE |
| KIAA0427 | rs8095199 | rs1384227 | 0.51 | C | 0.254 | 0.004491 | 0.84 | GAIN |

TABLE 1-continued

Confirmation of Novel Markers Associated with SZ risk

| Gene Name | Table B SNP | Test SNP in linkage disequilibrium | r² | Allele | Frequency in Cases | P | OR | Study |
|---|---|---|---|---|---|---|---|---|
| KIAA0427 | rs8095199 | rs8083702 | 0.51 | C | 0.251 | 0.04846 | 0.80 | CATIE |
| SMAD4 | rs12458752 | rs1789223 | 0.53 | G | 0.365 | 0.03536 | 0.89 | GAIN |
| SMAD4 | rs12958604 | rs1789223 | 0.53 | G | 0.365 | 0.03536 | 0.89 | GAIN |
| SMAD4 | rs2276163 | rs1789223 | 0.53 | G | 0.365 | 0.03536 | 0.89 | GAIN |
| SMAD4 | rs2298617 | rs1789223 | 0.53 | G | 0.365 | 0.03536 | 0.89 | GAIN |
| SMAD4 | rs3764465 | rs1789223 | 0.53 | G | 0.365 | 0.03536 | 0.89 | GAIN |
| DCC | rs1893572 | rs882333 | 0.76 | T | 0.326 | 0.03294 | 1.26 | CATIE |
| BMP7 | rs162316 | rs162313 | 0.57 | T | 0.109 | 0.01705 | 0.81 | GAIN |
| BMP7 | rs162316 | rs6127980 | 0.57 | A | 0.152 | 0.03952 | 1.35 | CATIE |

Example 2

Novel Markers Associated with Olanzapine Response

To assess drug response, the last observation for each patient in treatment Phase 1 of the CATIE trial was used as a primary assessment of efficacy. The standard FDA registration trial definition of response of ≥20% decrease in Positive and Negative Syndrome Scale (PANSS Total Score) was used to assign subjects to a response category. Individuals having composite ordinal effectiveness outcome (COMPEFF) scores of 1 of 2, indicating efficacy, were combined as were those with scores of 3 or 4, indicating lack of efficacy (Davis et al., Schizophr. Bull. 29:73-80 (2003)). The side effects category consisted of individuals discontinued for safety concerns (COMPEFF score 5).

Genetic analysis to document the influence of haplotypes on olanzapine response was performed using as described in Example 1 with the PLINK 1.03 whole genome analysis toolset developed by Purcell and coworkers (Purcell et al., Am. J. Hum. Genet. 81:559-575 (2007)). PLINK calculates P values for the allele-specific chi-squared test and the odds ratio (OR; or relative risk) associated with the minor allele.

Confirmation of SNP Effects on Olanzapine Response and Side Effects:

Tables 2 and 3 report the minor allele frequencies, P values, and ORs for SNPs in Tables B and C, that affect olanzapine response and side effect rates, respectively. Note in Tables 2 and 3 that haplotype blocks result in the same Test SNP being in linkage disequilibrium with multiple SNPs in Table B. Similarly, haplotype blocks result in multiple Test SNPs that can be used for each SNP listed in Table B, though such redundant examples are not presented in Tables 2 and 3.

Tables 2 and 3, provide numerous examples of SNP-based alleles that predict altered response to olanzapine. For Table 2, ORs of >1.0 indicate that the minor SNP allele is associated with greater clinical improvement, and ORs of <1.0 indicate that the minor SNP allele is associated with decreased susceptibility. For Table 3 ORs of >1.0 indicate that the minor SNP allele is associated with an increase in study ending side effects, and ORs of <1.0 indicate that the minor SNP allele is associated a decrease in study ending side effects.

TABLE 2

Alleles Affecting Positive Response to Olanzapine

| Gene Name | Table B SNP | Test SNP in linkage disequilibrium | r² | Allele | Frequency in responders | P | OR |
|---|---|---|---|---|---|---|---|
| CAMTA1 | rs449250 | rs277675 | 0.82 | C | 0.306 | 0.01603 | 0.47 |
| CAMTA1 | rs6577393 | rs6657847 | 0.51 | T | 0.264 | 0.01963 | 0.47 |
| CAMTA1 | rs6577401 | rs4243823 | 0.53 | A | 0.361 | 0.0152 | 0.48 |
| CAMTA1 | rs7554752 | rs10864255 | 0.96 | T | 0.458 | 0.0121 | 2.18 |
| PER3 | rs2640909 | rs228652 | 0.70 | A | 0.361 | 0.01662 | 2.21 |
| RP1-21O18.1 | rs4661572 | rs1000313 | 0.63 | G | 0.250 | 0.01139 | 2.69 |
| RP1-21O18.1 | rs6674129 | rs6665012 | 0.74 | G | 0.347 | 0.0226 | 0.50 |
| KCND3 | rs197422 | rs197412 | 0.94 | C | 0.556 | 0.02599 | 1.96 |
| KCND3 | rs3738298 | rs544941 | 0.65 | T | 0.206 | 0.04845 | 2.29 |
| DNM3 | rs10489730 | rs10910966 | 1.00 | C | 0.444 | 0.0202 | 2.06 |
| DNM3 | rs10752946 | rs1063412 | 0.97 | G | 0.542 | 0.04115 | 1.85 |
| DNM3 | rs3736791 | rs10910966 | 0.93 | C | 0.444 | 0.0202 | 2.06 |
| DNM3 | rs4576686 | rs10910966 | 0.79 | C | 0.444 | 0.0202 | 2.06 |
| SYT14 | rs11119426 | rs6701631 | 1.00 | T | 0.250 | 0.01892 | 2.48 |
| DPH3 | rs2245708 | rs2470508 | 0.97 | T | 0.514 | 0.0172 | 2.06 |
| DPH3 | rs2245721 | rs842254 | 1.00 | T | 0.343 | 0.02042 | 0.49 |
| DPH3 | rs842257 | rs842254 | 1.00 | T | 0.343 | 0.02042 | 0.49 |
| DPH3 | rs859703 | rs842254 | 1.00 | T | 0.343 | 0.02042 | 0.49 |
| ANK3 | rs10733757 | rs10761446 | 0.90 | C | 0.306 | 0.01208 | 2.44 |
| ANK3 | rs4568956 | rs10761446 | 0.57 | C | 0.306 | 0.01208 | 2.44 |
| ANK3 | rs7907721 | rs10761446 | 0.50 | C | 0.306 | 0.01208 | 2.44 |
| USH1C | rs16770 | rs2237961 | 0.92 | C | 0.042 | 0.02566 | 0.26 |
| NAV2 | rs2585788 | rs2625312 | 0.84 | A | 0.292 | 0.04703 | 2.02 |
| DAAM1 | rs10143918 | rs6573250 | 0.69 | T | 0.542 | 0.00853 | 2.22 |
| DAAM1 | rs1252989 | rs7143953 | 0.67 | T | 0.286 | 0.03629 | 0.51 |
| DAAM1 | rs1253005 | rs7143953 | 0.66 | T | 0.286 | 0.03629 | 0.51 |

TABLE 2-continued

Alleles Affecting Positive Response to Olanzapine

| Gene Name | Table B SNP | Test SNP in linkage disequilibrium | r² | Allele | Frequency in responders | P | OR |
|---|---|---|---|---|---|---|---|
| DAAM1 | rs1268579 | rs17096088 | 0.60 | G | 0.069 | 0.03473 | 0.34 |
| DAAM1 | rs4127823 | rs12589351 | 0.61 | C | 0.528 | 0.03651 | 1.88 |
| DAAM1 | rs4901909 | rs7143953 | 0.60 | T | 0.286 | 0.03629 | 0.51 |
| DAAM1 | rs8022614 | rs7143953 | 0.93 | T | 0.286 | 0.03629 | 0.51 |
| DAAM1 | rs941884 | rs7143953 | 0.51 | T | 0.286 | 0.03629 | 0.51 |
| GPR135 | rs10136708 | rs1253170 | 0.67 | T | 0.556 | 0.01391 | 2.10 |
| GPR135 | rs10138199 | rs1253170 | 0.54 | T | 0.556 | 0.01391 | 2.10 |
| GPR135 | rs1253181 | rs1253170 | 0.74 | T | 0.556 | 0.01391 | 2.10 |
| GPR135 | rs17255731 | rs1273156 | 0.62 | T | 0.597 | 0.03629 | 1.88 |
| GPR135 | rs4898989 | rs1253170 | 0.54 | T | 0.556 | 0.01391 | 2.10 |
| GPR135 | rs9323348 | rs1253170 | 0.54 | T | 0.556 | 0.01391 | 2.10 |
| EML1 | rs11160553 | rs11623084 | 0.88 | C | 0.485 | 0.0387 | 1.91 |
| EML1 | rs12433613 | rs11623084 | 0.77 | C | 0.485 | 0.0387 | 1.91 |
| EML1 | rs2250718 | rs10150225 | 0.53 | T | 0.667 | 0.01353 | 2.14 |
| EML1 | rs2273707 | rs10150225 | 1.00 | T | 0.667 | 0.01353 | 2.14 |
| EML1 | rs6575751 | rs11623084 | 0.88 | C | 0.485 | 0.0387 | 1.91 |
| HERC2 | rs1635168 | rs8041209 | 0.87 | T | 0.028 | 0.02867 | 0.21 |
| HERC2 | rs2238289 | rs8041209 | 0.51 | T | 0.028 | 0.02867 | 0.21 |
| HERC2 | rs7495174 | rs8041209 | 0.58 | T | 0.028 | 0.02867 | 0.21 |
| UNC13C | rs12910912 | rs12900128 | 0.52 | C | 0.361 | 0.01107 | 2.34 |
| NEDD4 | rs2303579 | rs10518831 | 0.51 | G | 0.194 | 0.02723 | 2.61 |
| NEDD4 | rs2303580 | rs10518831 | 0.51 | G | 0.194 | 0.02723 | 2.61 |
| SV2B | rs11630131 | rs1002556 | 0.83 | C | 0.250 | 0.01139 | 2.69 |
| SV2B | rs2073967 | rs1002556 | 0.51 | C | 0.250 | 0.01139 | 2.69 |
| SLCO3A1 | rs1517618 | rs207954 | 0.72 | T | 0.167 | 0.00355 | 0.35 |
| SLCO3A1 | rs2176452 | rs8027160 | 0.58 | G | 0.444 | 0.02815 | 1.98 |
| IGF1R | rs4966020 | rs11633717 | 0.88 | C | 0.236 | 0.02174 | 0.47 |
| IGF1R | rs7174918 | rs11633717 | 0.88 | C | 0.236 | 0.02174 | 0.47 |
| IGF1R | rs8038015 | rs11633717 | 0.82 | C | 0.236 | 0.02174 | 0.47 |
| NDRG4 | rs1058132 | rs1058132 | N/A | T | 0.371 | 0.02093 | 2.15 |
| NDRG4 | rs2271948 | rs1058132 | 0.74 | T | 0.371 | 0.02093 | 2.15 |
| NDRG4 | rs2280397 | rs1058132 | 0.92 | T | 0.371 | 0.02093 | 2.15 |
| C16orf74 | rs2305357 | rs442069 | 0.77 | G | 0.250 | 0.00821 | 0.42 |
| C16orf74 | rs373835 | rs442069 | 0.93 | G | 0.250 | 0.00821 | 0.42 |
| C16orf74 | rs386061 | rs442069 | 1.00 | G | 0.250 | 0.00821 | 0.42 |
| C16orf74 | rs386061 | rs386061 | N/A | C | 0.278 | 0.01847 | 0.47 |
| KIAA0427 | rs8094634 | rs1023943 | 0.72 | T | 0.208 | 0.0413 | 0.49 |
| SMAD7 | rs11874392 | rs12953717 | 0.65 | T | 0.528 | 0.02717 | 1.95 |
| SMAD7 | rs736839 | rs2337153 | 0.73 | A | 0.486 | 0.00224 | 2.59 |
| DYM | rs498929 | rs577979 | 0.96 | A | 0.125 | 0.01752 | 0.38 |
| DYM | rs833503 | rs577979 | 0.53 | A | 0.125 | 0.01752 | 0.38 |
| NDRG4 | rs1058132 | rs1058132 | N/A | T | 0.371 | 0.02093 | 2.15 |
| UNC13C | rs12910912 | rs12910912 | N/A | G | 0.250 | 0.01139 | 2.69 |
| SV2B | rs11630131 | rs11630131 | N/A | A | 0.222 | 0.01349 | 2.78 |

TABLE 3

Alleles Affecting Negative Side Effects for Olanzapine

| Gene Name | Table B SNP | Test SNP in linkage disequilibrium | r² | Allele | Frequency in discontinuers | P | OR |
|---|---|---|---|---|---|---|---|
| CAMTA1 | rs1417986 | rs2301488 | 0.54 | T | 0.630 | 0.03409 | 2.08 |
| CAMTA1 | rs7554752 | rs17030082 | 0.63 | A | 0.239 | 0.02475 | 0.43 |
| DNM3 | rs10752946 | rs1063412 | 0.97 | G | 0.283 | 0.009837 | 0.39 |
| DNM3 | rs13932 | rs9425606 | 0.75 | G | 0.130 | 0.007451 | 0.30 |
| DNM3 | rs2206543 | rs6690848 | 0.52 | G | 0.500 | 0.03358 | 2.06 |
| DNM3 | rs4075021 | rs12075807 | 0.71 | G | 0.565 | 0.03158 | 2.09 |
| DNM3 | rs4382763 | rs4072117 | 1.00 | C | 0.326 | 0.01406 | 2.55 |
| DNM3 | rs6701033 | rs6690848 | 0.52 | G | 0.500 | 0.03358 | 2.06 |
| DNM3 | rs965051 | rs6690848 | 0.52 | G | 0.500 | 0.03358 | 2.06 |
| RHOG | rs11030008 | rs11030008 | N/A | G | 0.522 | 0.01711 | 2.25 |
| RHOG | rs1451722 | rs11030008 | 0.76 | G | 0.522 | 0.01711 | 2.25 |
| RHOG | rs11030008 | rs11030008 | N/A | G | 0.522 | 0.01711 | 2.25 |
| OTOG | rs1003490 | rs11024348 | 0.77 | T | 0.370 | 0.003588 | 2.93 |
| OTOG | rs10832824 | rs11024348 | 0.52 | T | 0.370 | 0.003588 | 2.93 |
| OTOG | rs11024357 | rs869108 | 0.85 | G | 0.370 | 0.0001953 | 4.10 |
| OTOG | rs11024358 | rs869108 | 0.85 | G | 0.370 | 0.0001953 | 4.10 |
| OTOG | rs2023483 | rs11024348 | 0.50 | T | 0.370 | 0.003588 | 2.93 |
| OTOG | rs11024357 | rs11024357 | N/A | C | 0.370 | 0.0001953 | 4.10 |

TABLE 3-continued

Alleles Affecting Negative Side Effects for Olanzapine

| Gene Name | Table B SNP | Test SNP in linkage disequilibrium | r² | Allele | Frequency in discontinuers | P | OR |
|---|---|---|---|---|---|---|---|
| NAV2 | rs2585788 | rs2625312 | 0.84 | A | 0.065 | 0.00435 | 0.19 |
| NAV2 | rs6483629 | rs12099330 | 0.59 | T | 0.261 | 0.0278 | 2.47 |
| NAV2 | rs7125647 | rs2119981 | 0.61 | A | 0.238 | 0.004283 | 0.33 |
| ULK1 | rs11616018 | rs10794440 | 0.51 | G | 0.087 | 0.02249 | 0.30 |
| ULK1 | rs9652059 | rs10794440 | 0.55 | G | 0.087 | 0.02249 | 0.30 |
| TTC5 | rs1953552 | rs11623837 | 0.60 | G | 0.261 | 0.02693 | 0.44 |
| TEP1 | rs1713418 | rs1713419 | 1.00 | G | 0.283 | 0.04278 | 0.48 |
| DAAM1 | rs4127823 | rs12589351 | 0.61 | C | 0.304 | 0.04536 | 0.49 |
| GPR135 | rs10136708 | rs1253170 | 0.67 | T | 0.304 | 0.0307 | 0.46 |
| GPR135 | rs10138199 | rs1253170 | 0.54 | T | 0.304 | 0.0307 | 0.46 |
| GPR135 | rs1253181 | rs1253170 | 0.74 | T | 0.304 | 0.0307 | 0.46 |
| GPR135 | rs4898989 | rs1253170 | 0.54 | T | 0.304 | 0.0307 | 0.46 |
| GPR135 | rs9323348 | rs1253170 | 0.54 | T | 0.304 | 0.0307 | 0.46 |
| RTN1 | rs10145080 | rs12878097 | 0.55 | C | 0.087 | 0.01469 | 0.28 |
| RTN1 | rs12717467 | rs17731838 | 0.52 | T | 0.087 | 0.01821 | 0.29 |
| RTN1 | rs17310036 | rs1957311 | 0.79 | A | 0.182 | 0.008994 | 0.34 |
| EVL | rs4905933 | rs10148930 | 0.85 | A | 0.283 | 0.004807 | 0.36 |
| EVL | rs726514 | rs10148930 | 0.85 | A | 0.283 | 0.004807 | 0.36 |
| HERC2 | rs1635168 | rs2346050 | 0.87 | C | 0.152 | 0.03438 | 3.05 |
| HERC2 | rs2238289 | rs2346050 | 0.51 | C | 0.152 | 0.03438 | 3.05 |
| HERC2 | rs7495174 | rs2346050 | 0.58 | C | 0.152 | 0.03438 | 3.05 |
| UNC13C | rs11856476 | rs8024165 | 0.84 | T | 0.413 | 0.01984 | 2.28 |
| UNC13C | rs12594549 | rs2115820 | 0.90 | G | 0.068 | 0.04824 | 0.30 |
| UNC13C | rs12914912 | rs8024165 | 0.63 | T | 0.413 | 0.01984 | 2.28 |
| UNC13C | rs4776216 | rs8024165 | 0.52 | T | 0.413 | 0.01984 | 2.28 |
| NEDD4 | rs17238461 | rs9972348 | 0.57 | G | 0.326 | 0.04861 | 2.10 |
| Gcom1 | rs1908202 | rs2470360 | 0.64 | T | 0.413 | 0.03002 | 2.15 |
| GRINL1A | rs2069133 | rs1873993 | 0.84 | G | 0.522 | 0.02761 | 2.12 |
| ADAM10 | rs3764196 | rs7164844 | 0.51 | C | 0.043 | 0.02586 | 0.21 |
| N4BP1 | rs1039342 | rs8046716 | 0.61 | T | 0.348 | 0.04956 | 0.50 |
| N4BP1 | rs1120276 | rs8046716 | 0.61 | T | 0.348 | 0.04956 | 0.50 |
| N4BP1 | rs1224 | rs8046716 | 0.61 | T | 0.348 | 0.04956 | 0.50 |
| N4BP1 | rs2354580 | rs8046716 | 1.00 | T | 0.348 | 0.04956 | 0.50 |
| N4BP1 | rs3826176 | rs8046716 | 1.00 | T | 0.348 | 0.04956 | 0.50 |
| N4BP1 | rs9937623 | rs8046716 | 0.59 | T | 0.348 | 0.04956 | 0.50 |
| CDH8 | rs4636897 | rs11641508 | 1.00 | A | 0.023 | 0.03974 | 0.15 |
| BEAN | rs4247350 | rs4247350 | N/A | C | 0.174 | 0.02628 | 0.40 |
| KIAA0513 | rs4783121 | rs4783121 | N/A | A | 0.087 | 0.01362 | 6.76 |
| KIAA0182 | rs736845 | rs736845 | N/A | T | 0.182 | 0.04535 | 0.43 |
| PMP22 | rs13422 | rs230911 | 0.59 | A | 0.326 | 0.03223 | 0.47 |
| PMP22 | rs230938 | rs230911 | 0.61 | A | 0.326 | 0.03223 | 0.47 |
| PMP22 | rs231018 | rs230911 | 0.75 | A | 0.326 | 0.03223 | 0.47 |
| PMP22 | rs231021 | rs230911 | 0.78 | A | 0.326 | 0.03223 | 0.47 |
| FUSSEL18 | rs892583 | rs7244178 | 0.68 | T | 0.217 | 0.009474 | 0.37 |
| FUSSEL18 | rs892583 | rs892583 | N/A | G | 0.205 | 0.04865 | 0.45 |
| DCC | rs12457407 | rs11876282 | 0.65 | G | 0.591 | 0.04231 | 2.02 |
| DCC | rs1393331 | rs17506154 | 1.00 | C | 0.587 | 0.01453 | 2.30 |
| DCC | rs4940251 | rs17506154 | 0.53 | C | 0.587 | 0.01453 | 2.30 |
| DCC | rs6508145 | rs1031062 | 0.67 | G | 0.065 | 0.01905 | 0.25 |
| DCC | rs6508235 | rs2036415 | 0.58 | G | 0.548 | 0.03016 | 2.14 |
| DCC | rs7506904 | rs11876282 | 0.58 | G | 0.591 | 0.04231 | 2.02 |
| DCC | rs8097413 | rs10502969 | 1.00 | C | 0.196 | 0.01433 | 3.21 |
| DCC | rs950278 | rs11876282 | 0.56 | G | 0.591 | 0.04231 | 2.02 |
| TMEPAI | rs427278 | rs203386 | 0.51 | C | 0.591 | 0.0107 | 2.43 |

Example 3

Novel Markers Associated with Risperidone Response

To assess drug response, the last observation for each patient in treatment Phase 1 of the CATIE trial was used as a primary assessment of efficacy. The standard FDA registration trial definition of response of ≥20% decrease in Positive and Negative Syndrome Scale (PANSS Total Score) was used to assign subjects to a response category. Individuals having composite ordinal effectiveness outcome (COMPEFF) scores of 1 of 2, indicating efficacy, were combined as were those with scores of 3 or 4, indicating lack of efficacy (Davis et al., Schizophr. Bull. 29:73-80 (2003)). The side effects category consisted of individuals discontinued for safety concerns (COMPEFF score 5).

Genetic analysis to document the influence of haplotypes on risperidone response was performed using as described in Example 2 with the PLINK 1.03 whole genome analysis toolset developed by Purcell and coworkers (Purcell et al., Am. J. Hum. Genet. 81:559-575 (2007)). PLINK calculates P values for the allele-specific chi-squared test and the odds ratio (OR; or relative risk) associated with the minor allele.

Confirmation of SNP Effects on Risperidone Response and Side Effects:

Tables 4 and 5 report the minor allele frequencies, P values, and ORs for SNPs, in Tables B and C that affect risperidone response and side effect rates, respectively. Note in Tables 4 and 5 that haplotype blocks result in the same Test SNP being in linkage disequilibrium with multiple SNPs in Table B. Similarly, haplotype blocks result in multiple Test SNPs that can be used for each SNP listed in Table B, though such redundant examples are not presented in Tables 4 and 5.

Tables 4 and 5, provide numerous examples of SNP-based alleles that predict altered response to risperidone. For Table 4, ORs of >1.0 indicate that the minor SNP allele is associated with greater clinical improvement, and ORs of <1.0 indicate that the minor SNP allele is associated with lesser clinical improvement. For Table 5 ORs of >1.0 indicate that the minor SNP allele is associated with an increase in study ending side effects, and ORs of <1.0 indicate that the minor SNP allele is associated a decrease in study ending side effects.

TABLE 4

Alleles Affecting Positive Response to Risperidone

| Gene Name | Table B SNP | Test SNP in linkage disequilibrium | r² | Allele | Frequency in responders | P | OR |
|---|---|---|---|---|---|---|---|
| RERE | rs12136689 | rs10779702 | 0.76 | A | 0.266 | 0.03124 | 0.49 |
| RERE | rs8627 | rs10779702 | 0.52 | A | 0.266 | 0.03124 | 0.49 |
| DNM3 | rs4382763 | rs6701929 | 0.84 | C | 0.156 | 0.04448 | 0.46 |
| RABGAP1L | rs6425302 | rs1793319 | 0.59 | A | 0.500 | 0.02472 | 2.00 |
| CACNA1E | rs199960 | rs3856093 | 0.51 | C | 0.281 | 0.04197 | 0.51 |
| CACNA1E | rs3856090 | rs3856093 | 1.00 | C | 0.281 | 0.04197 | 0.51 |
| ANK3 | rs2393607 | rs2393602 | 0.56 | C | 0.484 | 0.04133 | 1.88 |
| PTPN5 | rs4345940 | rs4757718 | 0.53 | G | 0.219 | 0.04081 | 0.49 |
| SYT13 | rs11038382 | rs7943596 | 1.00 | C | 0.194 | 0.03562 | 0.46 |
| SYT13 | rs2863182 | rs7943596 | 0.84 | C | 0.194 | 0.03562 | 0.46 |
| SYT13 | rs4992029 | rs7943596 | 0.61 | C | 0.194 | 0.03562 | 0.46 |
| CHFR | rs3741494 | rs3741494 | N/A | T | 0.194 | 0.0429 | 2.40 |
| JPH4 | rs12897422 | rs12897422 | N/A | A | 0.188 | 0.00592 | 3.58 |
| DAAM1 | rs4898983 | rs2099636 | 0.96 | A | 0.203 | 0.03748 | 0.48 |
| NEDD4 | rs2303579 | rs10518831 | 0.51 | G | 0.266 | 0.002306 | 3.31 |
| NEDD4 | rs2303580 | rs10518831 | 0.51 | G | 0.266 | 0.002306 | 3.31 |
| GRINL1A | rs4774275 | rs1873995 | 0.51 | G | 0.359 | 0.0403 | 0.53 |
| Gcom1 | rs986868 | rs11071337 | 0.59 | C | 0.609 | 0.01971 | 2.05 |
| SLCO3A1 | rs2286355 | rs11630872 | 0.85 | T | 0.469 | 0.03077 | 1.96 |
| N4BP1 | rs1039342 | rs2129243 | 1.00 | T | 0.258 | 0.03604 | 0.49 |
| N4BP1 | rs1120276 | rs2129243 | 1.00 | T | 0.258 | 0.03604 | 0.49 |
| N4BP1 | rs1224 | rs2129243 | 1.00 | T | 0.258 | 0.03604 | 0.49 |
| N4BP1 | rs2354580 | rs2129243 | 0.61 | T | 0.258 | 0.03604 | 0.49 |
| N4BP1 | rs3826176 | rs2129243 | 0.61 | T | 0.258 | 0.03604 | 0.49 |
| N4BP1 | rs9937623 | rs2129243 | 0.96 | T | 0.258 | 0.03604 | 0.49 |
| CBLN1 | rs11076478 | rs12598711 | 0.89 | G | 0.422 | 0.01435 | 2.19 |
| CBLN1 | rs9935379 | rs12598711 | 0.72 | G | 0.422 | 0.01435 | 2.19 |
| CDH8 | rs1397131 | rs9925201 | 0.76 | G | 0.594 | 0.02591 | 1.98 |
| CDH8 | rs8057338 | rs9925201 | 0.79 | G | 0.594 | 0.02591 | 1.98 |
| CDH8 | rs9302540 | rs9925201 | 0.79 | G | 0.594 | 0.02591 | 1.98 |
| CDH8 | rs9302540 | rs9302540 | N/A | G | 0.563 | 0.04052 | 1.88 |
| SMAD7 | rs736839 | rs2337153 | 0.73 | A | 0.563 | 0.003133 | 2.49 |
| DYM | rs8096141 | rs7239949 | 0.87 | G | 0.113 | 0.04631 | 3.18 |
| TMEPAI | rs427278 | rs203386 | 0.51 | C | 0.258 | 0.03803 | 0.50 |

TABLE 5

Alleles Affecting Negative Side Effects for Risperidone

| Gene Name | Table B SNP | Test SNP in linkage disequilibrium | r² | Allele | Frequency in discontinuers | P | OR |
|---|---|---|---|---|---|---|---|
| CAMTA1 | rs228651 | rs11121029 | 0.51 | A | 0.000 | 0.009148 | 0.00 |
| PER3 | rs2640909 | rs228652 | 0.70 | A | 0.542 | 0.01808 | 2.77 |
| RP1-21O18.1 | rs2073091 | rs761288 | 0.69 | C | 0.542 | 0.004869 | 3.34 |
| RP1-21O18.1 | rs4661572 | rs761288 | 0.56 | C | 0.542 | 0.004869 | 3.34 |
| SLC6A17 | rs12133992 | rs2784140 | 0.90 | G | 0.708 | 0.0434 | 2.54 |
| SLC6A17 | rs534276 | rs2784140 | 0.60 | G | 0.708 | 0.0434 | 2.54 |
| KCND3 | rs197422 | rs197412 | 0.94 | C | 0.167 | 0.01199 | 0.26 |
| DNM3 | rs13932 | rs9425606 | 0.75 | G | 0.500 | 0.00697 | 3.21 |
| DNM3 | rs4382763 | rs12410416 | 1.00 | C | 0.417 | 0.008488 | 3.20 |
| DNM3 | rs4382763 | rs4382763 | N/A | A | 0.375 | 0.0302 | 2.68 |
| KCNH1 | rs1770213 | rs1777264 | 0.94 | C | 0.000 | 0.01943 | 0.00 |
| DPH3 | rs2245708 | rs842252 | 1.00 | A | 0.583 | 0.02254 | 2.68 |
| EXOC2 | rs2493049 | rs12154040 | 0.54 | C | 0.667 | 0.00848 | 3.21 |
| ANK3 | rs1551684 | rs1551683 | 1.00 | T | 0.292 | 0.007594 | 3.71 |
| ANK3 | rs1551684 | rs1551684 | N/A | A | 0.250 | 0.03112 | 3.04 |
| DEAF1 | rs4963145 | rs936465 | 0.53 | G | 0.182 | 0.002149 | 0.20 |
| DEAF1 | rs6597990 | rs10902190 | 0.58 | T | 0.083 | 0.01958 | 0.20 |
| DEAF1 | rs6597996 | rs936465 | 0.58 | G | 0.182 | 0.002149 | 0.20 |
| DEAF1 | rs936465 | rs936465 | N/A | G | 0.182 | 0.002149 | 0.20 |

TABLE 5-continued

Alleles Affecting Negative Side Effects for Risperidone

| Gene Name | Table B SNP | Test SNP in linkage disequilibrium | r² | Allele | Frequency in discontinuers | P | OR |
|---|---|---|---|---|---|---|---|
| PTPN5 | rs4345940 | rs7117716 | 0.97 | T | 0.583 | 0.004185 | 3.42 |
| PTPN5 | rs7932938 | rs7117716 | 0.54 | T | 0.583 | 0.004185 | 3.42 |
| SLC17A6 | rs11026532 | rs1155331 | 0.96 | T | 0.042 | 0.01523 | 0.12 |
| SYT13 | rs4992029 | rs7117240 | 0.55 | C | 0.625 | 0.0497 | 2.37 |
| SYT13 | rs8929 | rs7117240 | 0.54 | C | 0.625 | 0.0497 | 2.37 |
| RTN4RL2 | rs2511986 | rs2649667 | 0.87 | T | 0.000 | 0.006313 | 0.00 |
| KIAA1853 | rs7297606 | rs4075945 | 1.00 | T | 0.333 | 0.0007673 | 4.88 |
| RIMBP2 | rs2277356 | rs4759462 | 0.76 | T | 0.292 | 0.0369 | 2.77 |
| NDRG2 | rs1243444 | rs1243446 | 0.58 | G | 0.167 | 0.01347 | 0.26 |
| NDRG2 | rs1243446 | rs1243446 | N/A | G | 0.167 | 0.01347 | 0.26 |
| DAAM1 | rs17833769 | rs1958180 | 0.95 | G | 0.083 | 0.03279 | 0.22 |
| DAAM1 | rs1958180 | rs1958180 | N/A | G | 0.083 | 0.03279 | 0.22 |
| GPR135 | rs10136708 | rs1253103 | 0.54 | C | 0.250 | 0.04172 | 0.38 |
| GPR135 | rs10138199 | rs1253103 | 0.88 | C | 0.250 | 0.04172 | 0.38 |
| GPR135 | rs1253181 | rs1253103 | 0.71 | C | 0.250 | 0.04172 | 0.38 |
| GPR135 | rs17255731 | rs1253103 | 0.57 | C | 0.250 | 0.04172 | 0.38 |
| GPR135 | rs4898989 | rs1253103 | 0.88 | C | 0.250 | 0.04172 | 0.38 |
| GPR135 | rs9323348 | rs1253103 | 0.88 | C | 0.250 | 0.04172 | 0.38 |
| HERC2 | rs11074322 | rs6497272 | 1.00 | G | 0.083 | 0.003758 | 15.55 |
| HERC2 | rs1635168 | rs6497292 | 0.87 | G | 0.208 | 0.002843 | 5.40 |
| HERC2 | rs2238289 | rs6497292 | 0.51 | G | 0.208 | 0.002843 | 5.40 |
| HERC2 | rs7495174 | rs6497292 | 0.58 | G | 0.208 | 0.002843 | 5.40 |
| UNC13C | rs16974691 | rs16974712 | 0.96 | T | 0.042 | 0.04931 | 0.16 |
| SV2B | rs1117388 | rs1117387 | 1.00 | T | 0.042 | 0.03508 | 0.15 |
| SV2B | rs3743444 | rs1117387 | 0.57 | T | 0.042 | 0.03508 | 0.15 |
| SLCO3A1 | rs2176452 | rs8027160 | 0.58 | G | 0.500 | 0.01784 | 2.78 |
| IGF1R | rs11247380 | rs3743258 | 0.93 | A | 0.500 | 0.02156 | 2.70 |
| IGF1R | rs1879613 | rs3743258 | 0.51 | A | 0.500 | 0.02156 | 2.70 |
| CBLN1 | rs3743777 | rs8052939 | 0.89 | G | 0.167 | 0.03498 | 3.62 |
| CDH8 | rs11075445 | rs13336134 | 0.80 | C | 0.583 | 0.02155 | 2.72 |
| CDH8 | rs1369918 | rs13336134 | 0.80 | C | 0.583 | 0.02155 | 2.72 |
| CDH8 | rs1978796 | rs13336134 | 0.80 | C | 0.583 | 0.02155 | 2.72 |
| CDH8 | rs6498807 | rs13336134 | 1.00 | C | 0.583 | 0.02155 | 2.72 |
| CDH8 | rs9939991 | rs13336134 | 0.55 | C | 0.583 | 0.02155 | 2.72 |
| CDH11 | rs35144 | rs40115 | 1.00 | T | 0.500 | 0.01784 | 2.78 |
| CDH11 | rs35148 | rs40115 | 0.68 | T | 0.500 | 0.01784 | 2.78 |
| CDH11 | rs35186 | rs40115 | 0.56 | T | 0.500 | 0.01784 | 2.78 |
| CDH11 | rs35195 | rs35195 | N/A | A | 0.500 | 0.01938 | 2.74 |
| CDH11 | rs35144 | rs35144 | N/A | C | 0.500 | 0.02156 | 2.70 |
| DCC | rs1393331 | rs1502229 | 0.84 | G | 0.136 | 0.01594 | 0.24 |
| DCC | rs4940251 | rs1502229 | 0.59 | G | 0.136 | 0.01594 | 0.24 |
| DCC | rs6508235 | rs1502229 | 0.58 | G | 0.136 | 0.01594 | 0.24 |

Example 4

Novel Markers Associated with Quetiapine Response

To assess drug response, the last observation for each patient in treatment Phase 1 of the CATIE trial was used as a primary assessment of efficacy. The standard FDA registration trial definition of response of ≥20% decrease in Positive and Negative Syndrome Scale (PANSS Total Score) was used to assign subjects to a response category. Individuals having composite ordinal effectiveness outcome (COMPEFF) scores of 1 of 2, indicating efficacy, were combined as were those with scores of 3 or 4, indicating lack of efficacy (Davis et al., Schizophr. Bull. 29:73-80 (2003)). The side effects category consisted of individuals discontinued for safety concerns (COMPEFF score 5).

Genetic analysis to document the influence of haplotypes on quetiapine response was performed using as described in Example 2 with the PLINK 1.03 whole genome analysis toolset developed by Purcell and coworkers (Purcell et al., Am. J. Hum. Genet. 81:559-575 (2007)). PLINK calculates P values for the allele-specific chi-squared test and the odds ratio (OR; or relative risk) associated with the minor allele.

Confirmation of SNP Effects on Quetiapine Response and Side Effects:

Tables 6 and 7 report the minor allele frequencies, P values, and ORs for SNPs, in Tables B and C that affect quetiapine response and side effect rates, respectively. Note in Tables 6 and 7 that haplotype blocks result in the same Test SNP being in linkage disequilibrium with multiple SNPs in Table B. Similarly, haplotype blocks result in multiple Test SNPs that can be used for each SNP listed in Table B, though such redundant examples are not presented in Tables 6 and 7.

Tables 6 and 7, provide numerous examples of SNP-based alleles that predict altered response to quetiapine. For Table 6, ORs of >1.0 indicate that the minor SNP allele is associated with greater clinical improvement, and ORs of <1.0 indicate that the minor SNP allele is associated with lesser clinical improvement. For Table 7 ORs of >1.0 indicate that the minor SNP allele is associated with an increase in study ending side effects, and ORs of <1.0 indicate that the minor SNP allele is associated a decrease in study ending side effects.

TABLE 6

Alleles Affecting Positive Response to Quetiapine

| Gene Name | Table B SNP | Test SNP in linkage disequilibrium | r² | Allele | Frequency in responders | P | OR |
|---|---|---|---|---|---|---|---|
| RP1-21O18.1 | rs7546786 | rs7546786 | N/A | C | 0.340 | 0.03888 | 2.12 |
| CACNA1E | rs638132 | rs678643 | 0.86 | G | 0.300 | 0.04268 | 2.14 |
| CAMK1G | rs2356933 | rs6683256 | 1.00 | T | 0.208 | 0.02384 | 0.42 |
| EXOC2 | rs2294660 | rs1150856 | 0.55 | C | 0.280 | 0.03354 | 2.28 |
| EXOC2 | rs998777 | rs17135931 | 0.66 | A | 0.300 | 0.0313 | 2.26 |
| YPEL4 | rs1798177 | rs1798173 | 0.84 | T | 0.280 | 0.01513 | 0.42 |
| YPEL4 | rs7947357 | rs1798173 | 0.84 | T | 0.280 | 0.01513 | 0.42 |
| CTNND1 | rs10896644 | rs1786438 | 0.97 | T | 0.313 | 0.007608 | 0.40 |
| CTNND1 | rs11570176 | rs1786438 | 0.97 | T | 0.313 | 0.007608 | 0.40 |
| CTNND1 | rs2156638 | rs1786438 | 1.00 | T | 0.313 | 0.007608 | 0.40 |
| CTNND1 | rs652908 | rs1786438 | 1.00 | T | 0.313 | 0.007608 | 0.40 |
| CTNND1 | rs708228 | rs576859 | 1.00 | A | 0.458 | 0.01184 | 2.36 |
| KIAA1853 | rs7297606 | rs4075945 | 1.00 | T | 0.200 | 0.009895 | 3.30 |
| STX2 | rs1236 | rs10848205 | 1.00 | T | 0.580 | 0.02392 | 2.11 |
| STX2 | rs4759517 | rs10848205 | 0.81 | T | 0.580 | 0.02392 | 2.11 |
| STX2 | rs6486600 | rs10848205 | 0.79 | T | 0.580 | 0.02392 | 2.11 |
| STX2 | rs6486602 | rs10848205 | 0.81 | T | 0.580 | 0.02392 | 2.11 |
| DACT1 | rs464582 | rs464582 | N/A | C | 0.520 | 0.03106 | 2.04 |
| DAAM1 | rs10143918 | rs10873113 | 0.58 | T | 0.280 | 0.0335 | 2.29 |
| DAAM1 | rs11626926 | rs4901921 | 0.85 | T | 0.563 | 0.01108 | 2.36 |
| DAAM1 | rs12147707 | rs10873113 | 0.86 | T | 0.280 | 0.0335 | 2.29 |
| DAAM1 | rs17095965 | rs10873113 | 0.86 | T | 0.280 | 0.0335 | 2.29 |
| DAAM1 | rs4127823 | rs4901921 | 0.60 | T | 0.563 | 0.01108 | 2.36 |
| GPR135 | rs10136708 | rs1253103 | 0.54 | C | 0.280 | 0.04103 | 0.49 |
| GPR135 | rs10138199 | rs1253103 | 0.88 | C | 0.280 | 0.04103 | 0.49 |
| GPR135 | rs1253181 | rs1253103 | 0.71 | C | 0.280 | 0.04103 | 0.49 |
| GPR135 | rs17255731 | rs1253103 | 0.57 | C | 0.280 | 0.04103 | 0.49 |
| GPR135 | rs4898989 | rs1253103 | 0.88 | C | 0.280 | 0.04103 | 0.49 |
| GPR135 | rs9323348 | rs1253103 | 0.88 | C | 0.280 | 0.04103 | 0.49 |
| RTN1 | rs10145080 | rs17731838 | 0.65 | T | 0.100 | 0.008147 | 0.28 |
| RTN1 | rs12717467 | rs17731838 | 0.52 | T | 0.100 | 0.008147 | 0.28 |
| RTN1 | rs17310036 | rs17731838 | 0.81 | T | 0.100 | 0.008147 | 0.28 |
| EML1 | rs2273704 | rs12590861 | 0.61 | C | 0.500 | 0.001846 | 2.84 |
| EML1 | rs7143905 | rs12590861 | 0.70 | C | 0.500 | 0.001846 | 2.84 |
| EML1 | rs2273704 | rs2273704 | N/A | C | 0.520 | 0.01052 | 2.34 |
| EVL | rs3206354 | rs12431406 | 0.58 | C | 0.140 | 0.007758 | 4.53 |
| UNC13C | rs9920139 | rs1961635 | 0.55 | T | 0.200 | 0.03866 | 2.52 |
| UNC13C | rs9920150 | rs1961635 | 0.61 | T | 0.200 | 0.03866 | 2.52 |
| Gcom1 | rs986868 | rs11071337 | 0.59 | C | 0.640 | 0.003757 | 2.64 |
| AKAP13 | rs1053992 | rs12440599 | 0.61 | T | 0.460 | 0.04784 | 1.94 |
| AKAP13 | rs11073502 | rs2291048 | 0.53 | A | 0.174 | 0.03896 | 0.42 |
| AKAP13 | rs2061821 | rs12440599 | 0.96 | T | 0.460 | 0.04784 | 1.94 |
| AKAP13 | rs2061822 | rs12440599 | 0.89 | T | 0.460 | 0.04784 | 1.94 |
| AKAP13 | rs2061824 | rs12440599 | 0.96 | T | 0.460 | 0.04784 | 1.94 |
| AKAP13 | rs338523 | rs12440599 | 0.96 | T | 0.460 | 0.04784 | 1.94 |
| AKAP13 | rs4075254 | rs12440599 | 0.96 | T | 0.460 | 0.04784 | 1.94 |
| AKAP13 | rs4075256 | rs12440599 | 0.96 | T | 0.460 | 0.04784 | 1.94 |
| AKAP13 | rs4842895 | rs12440599 | 0.76 | T | 0.460 | 0.04784 | 1.94 |
| AKAP13 | rs4843074 | rs12440599 | 0.96 | T | 0.460 | 0.04784 | 1.94 |
| AKAP13 | rs4843075 | rs12440599 | 0.96 | T | 0.460 | 0.04784 | 1.94 |
| AKAP13 | rs7162168 | rs12440599 | 0.96 | T | 0.460 | 0.04784 | 1.94 |
| SV2B | rs1075840 | rs1079535 | 0.87 | A | 0.480 | 0.02175 | 2.15 |
| SV2B | rs2301665 | rs1079535 | 0.74 | A | 0.480 | 0.02175 | 2.15 |
| SV2B | rs8027498 | rs1079535 | 0.60 | A | 0.480 | 0.02175 | 2.15 |
| RGMA | rs13167 | rs11074130 | 0.59 | T | 0.180 | 0.003617 | 4.30 |
| IGF1R | rs11247380 | rs1521481 | 0.73 | C | 0.240 | 0.02095 | 0.43 |
| IGF1R | rs2684808 | rs951715 | 0.51 | G | 0.260 | 0.02238 | 0.44 |
| IGF1R | rs8030950 | rs1879612 | 0.66 | C | 0.188 | 0.02051 | 0.40 |
| BEAN | rs4247350 | rs11645280 | 0.61 | G | 0.417 | 0.02122 | 2.22 |
| FUSSEL18 | rs892583 | rs2164098 | 0.95 | G | 0.420 | 0.01515 | 2.30 |
| FUSSEL18 | rs892583 | rs892583 | N/A | G | 0.391 | 0.04015 | 2.08 |
| KIAA0427 | rs2175565 | rs12456253 | 0.68 | G | 0.220 | 0.03731 | 0.46 |
| KIAA0427 | rs4939813 | rs1994559 | 0.53 | A | 0.240 | 0.006482 | 3.18 |
| KIAA0427 | rs937021 | rs12458062 | 0.52 | T | 0.600 | 0.03871 | 1.98 |
| DCC | rs12457407 | rs7506909 | 0.93 | A | 0.520 | 0.01922 | 2.17 |
| DCC | rs1393331 | rs17504520 | 0.78 | G | 0.587 | 0.02781 | 2.12 |
| DCC | rs2229080 | rs9966074 | 0.60 | T | 0.340 | 0.01745 | 0.45 |
| DCC | rs4940251 | rs7506909 | 0.67 | A | 0.520 | 0.01922 | 2.17 |
| DCC | rs6508145 | rs1454731 | 0.82 | C | 0.320 | 0.01176 | 2.57 |
| DCC | rs6508235 | rs10515959 | 0.77 | T | 0.340 | 0.03565 | 2.13 |
| DCC | rs7506904 | rs7506909 | 0.83 | A | 0.520 | 0.01922 | 2.17 |
| DCC | rs950278 | rs9966074 | 0.87 | T | 0.340 | 0.01745 | 0.45 |

TABLE 7

Alleles Affecting Negative Side Effects for Quetiapine

| Gene Name | Table B SNP | Test SNP in linkage disequilibrium | $r^2$ | Allele | Frequency in discontinuers | P | OR |
|---|---|---|---|---|---|---|---|
| CAMTA1 | rs845197 | rs845265 | 0.91 | T | 0.095 | 0.02848 | 0.31 |
| RERE | rs7530745 | rs6577499 | 1.00 | G | 0.273 | 0.03893 | 0.46 |
| RERE | rs7554486 | rs6577499 | 0.65 | G | 0.273 | 0.03893 | 0.46 |
| SLC16A4 | rs10857820 | rs3768458 | 0.65 | T | 0.318 | 0.04016 | 0.48 |
| SLC16A4 | rs1334882 | rs3768458 | 1.00 | T | 0.318 | 0.04016 | 0.48 |
| KCNA10 | rs3768456 | rs7543509 | 1.00 | G | 0.182 | 0.0001722 | 8.11 |
| CACNA1E | rs17494681 | rs17494681 | N/A | T | 0.296 | 0.0268 | 2.40 |
| CACNA1E | rs3856090 | rs7534913 | 0.50 | G | 0.381 | 0.04817 | 0.50 |
| KCNH1 | rs4620600 | rs4951495 | 0.79 | A | 0.068 | 0.01863 | 0.25 |
| ANK3 | rs2393596 | rs10761451 | 0.78 | G | 0.159 | 0.04472 | 0.41 |
| DEAF1 | rs7109335 | rs7123677 | 0.84 | T | 0.227 | 0.03893 | 2.46 |
| DEAF1 | rs7121608 | rs7123677 | 0.92 | T | 0.227 | 0.03893 | 2.46 |
| DEAF1 | rs7935419 | rs7123677 | 0.92 | T | 0.227 | 0.03893 | 2.46 |
| USH1C | rs10766408 | rs2041032 | 0.51 | T | 0.568 | 0.01695 | 2.27 |
| USH1C | rs2041027 | rs2041032 | 0.78 | T | 0.568 | 0.01695 | 2.27 |
| USH1C | rs2237957 | rs2041032 | 0.69 | T | 0.568 | 0.01695 | 2.27 |
| KCNC1 | rs10766434 | rs2299637 | 0.66 | A | 0.455 | 0.01364 | 2.37 |
| KCNC1 | rs2299637 | rs2299637 | N/A | A | 0.455 | 0.01364 | 2.37 |
| KCNC1 | rs757514 | rs2299637 | 0.66 | A | 0.455 | 0.01364 | 2.37 |
| NAV2 | rs10833202 | rs11025328 | 0.61 | A | 0.727 | 0.001805 | 3.13 |
| SLC17A6 | rs11026523 | rs1562445 | 0.79 | A | 0.068 | 0.008164 | 0.22 |
| SLC17A6 | rs1155821 | rs1562445 | 0.96 | A | 0.068 | 0.008164 | 0.22 |
| SLC17A6 | rs2078352 | rs1562445 | 1.00 | A | 0.068 | 0.008164 | 0.22 |
| SLC17A6 | rs2246710 | rs1562445 | 1.00 | A | 0.068 | 0.008164 | 0.22 |
| SLC17A6 | rs2078352 | rs2078352 | N/A | T | 0.068 | 0.01127 | 0.23 |
| LRRC4C | rs10837367 | rs10501225 | 0.69 | A | 0.023 | 0.03099 | 0.14 |
| RTN4RL2 | rs2511986 | rs2649667 | 0.87 | T | 0.409 | 0.04498 | 2.04 |
| KIAA1853 | rs7297606 | rs4075945 | 1.00 | T | 0.023 | 0.04399 | 0.16 |
| CHFR | rs2306536 | rs11147101 | 1.00 | G | 0.091 | 0.04245 | 0.34 |
| CHFR | rs4758954 | rs11147101 | 1.00 | G | 0.091 | 0.04245 | 0.34 |
| GPR135 | rs10136708 | rs1253103 | 0.54 | C | 0.546 | 0.02737 | 2.13 |
| GPR135 | rs10138199 | rs2774052 | 0.72 | A | 0.614 | 0.01223 | 2.38 |
| GPR135 | rs1253181 | rs2774052 | 0.89 | A | 0.614 | 0.01223 | 2.38 |
| GPR135 | rs17255731 | rs2774052 | 0.70 | A | 0.614 | 0.01223 | 2.38 |
| GPR135 | rs4898989 | rs2774052 | 0.72 | A | 0.614 | 0.01223 | 2.38 |
| GPR135 | rs9323348 | rs2774052 | 0.72 | A | 0.614 | 0.01223 | 2.38 |
| EML1 | rs2273704 | rs12590861 | 0.61 | C | 0.182 | 0.02262 | 0.39 |
| EML1 | rs7143905 | rs12590861 | 0.70 | C | 0.182 | 0.02262 | 0.39 |
| EVL | rs1190954 | rs1190967 | 0.96 | G | 0.182 | 0.02583 | 0.40 |
| EVL | rs1190956 | rs1190967 | 0.60 | G | 0.182 | 0.02583 | 0.40 |
| EVL | rs1190974 | rs1190967 | 0.96 | G | 0.182 | 0.02583 | 0.40 |
| WDR25 | rs10873518 | rs7492607 | 0.97 | C | 0.523 | 0.01011 | 2.43 |
| UNC13C | rs11856476 | rs8023723 | 0.53 | G | 0.477 | 0.04506 | 2.00 |
| UNC13C | rs12914912 | rs8023723 | 0.86 | G | 0.477 | 0.04506 | 2.00 |
| UNC13C | rs4776216 | rs8023723 | 1.00 | G | 0.477 | 0.04506 | 2.00 |
| NEDD4 | rs17238461 | rs2175104 | 0.53 | A | 0.048 | 0.04132 | 0.24 |
| AKAP13 | rs338556 | rs870689 | 0.91 | A | 0.136 | 0.009364 | 4.58 |
| KLHL25 | rs2430838 | rs870689 | 1.00 | A | 0.136 | 0.009364 | 4.58 |
| KLHL25 | rs2430838 | rs2430838 | N/A | T | 0.114 | 0.03635 | 3.67 |
| SLCO3A1 | rs2176452 | rs8027160 | 0.58 | G | 0.136 | 0.01379 | 0.33 |
| NETO2 | rs11859615 | rs9928466 | 0.85 | C | 0.000 | 0.03539 | 0.00 |
| NETO2 | rs16952126 | rs9928466 | 0.85 | C | 0.000 | 0.03539 | 0.00 |
| NETO2 | rs7184206 | rs9928466 | 1.00 | C | 0.000 | 0.03539 | 0.00 |
| NETO2 | rs9923731 | rs9928466 | 0.85 | C | 0.000 | 0.03539 | 0.00 |
| ZNF423 | rs12924119 | rs2883977 | 0.51 | C | 0.341 | 0.005838 | 2.86 |
| NDRG4 | rs13333449 | rs16960170 | 0.80 | C | 0.341 | 0.03824 | 2.18 |
| NDRG4 | rs7202037 | rs16960170 | 0.67 | C | 0.341 | 0.03824 | 2.18 |
| CDH8 | rs1397131 | rs16964164 | 0.90 | T | 0.523 | 0.02822 | 2.13 |
| CDH8 | rs8057338 | rs16964164 | 0.93 | T | 0.523 | 0.02822 | 2.13 |
| CDH8 | rs9302540 | rs16964164 | 0.93 | T | 0.523 | 0.02822 | 2.13 |
| CDH11 | rs35144 | rs40115 | 1.00 | T | 0.477 | 0.03109 | 2.12 |
| CDH11 | rs35148 | rs40115 | 0.68 | T | 0.477 | 0.03109 | 2.12 |
| CDH11 | rs35186 | rs40115 | 0.56 | T | 0.477 | 0.03109 | 2.12 |
| CDH11 | rs35195 | rs35195 | N/A | A | 0.477 | 0.04506 | 2.00 |
| CDH11 | rs35186 | rs35186 | N/A | T | 0.619 | 0.03313 | 2.13 |
| BEAN | rs4247350 | rs1063438 | 0.59 | A | 0.182 | 0.006152 | 0.32 |
| KIAA0427 | rs2306514 | rs2306514 | N/A | G | 0.500 | 0.02294 | 2.19 |
| KIAA0427 | rs752151 | rs2337099 | 0.83 | G | 0.136 | 0.003807 | 5.76 |
| KIAA0427 | rs937021 | rs12458062 | 0.52 | T | 0.341 | 0.044 | 0.49 |
| TMEPAI | rs427278 | rs203386 | 0.51 | C | 0.250 | 0.02943 | 0.44 |

Example 5

Novel Markers Associated with Perphenazine Response

To assess drug response, the last observation for each patient in treatment Phase 1 of the CATIE trial was used as a primary assessment of efficacy. The standard FDA registration trial definition of response of ≥20% decrease in Positive and Negative Syndrome Scale (PANSS Total Score) was used to assign subjects to a response category. Individuals having composite ordinal effectiveness outcome (COMPEFF) scores of 1 of 2, indicating efficacy, were combined as were those with scores of 3 or 4, indicating lack of efficacy (Davis et al., Schizophr. Bull. 29:73-80 (2003)). The side effects category consisted of individuals discontinued for safety concerns (COMPEFF score 5).

Genetic analysis to document the influence of haplotypes on perphenazine response was performed using as described in Example 2 with the PLINK 1.03 whole genome analysis toolset developed by Purcell and coworkers (Purcell et al., Am. J. Hum. Genet. 81:559-575 (2007)). PLINK calculates P values for the allele-specific chi-squared test and the odds ratio (OR; or relative risk) associated with the minor allele.

Confirmation of SNP Effects on Perphenazine Response and Side Effects:

Tables 8 and 9 report the minor allele frequencies, P values, and ORs for SNPs, in Tables B and C that affect perphenazine response and side effect rates, respectively. Note in Tables 8 and 9 that haplotype blocks result in the same Test SNP being in linkage disequilibrium with multiple SNPs in Table B. Similarly, haplotype blocks result in multiple Test SNPs that can be used for each SNP listed in Table B, though such redundant examples are not presented in Tables 8 and 9.

Tables 8 and 9, provide numerous examples of SNP-based alleles that predict altered response to perphenazine. For Table 8, ORs of >1.0 indicate that the minor SNP allele is associated with greater clinical improvement, and ORs of <1.0 indicate that the minor SNP allele is associated with lesser clinical improvement. For Table 9 ORs of >1.0 indicate that the minor SNP allele is associated with an increase in study ending side effects, and ORs of <1.0 indicate that the minor SNP allele is associated a decrease in study ending side effects.

TABLE 8

Alleles Affecting Positive Response to Perphenazine

| Gene Name | Table B SNP | Test SNP in linkage disequilibrium | $r^2$ | Allele | Frequency in responders | P | OR |
|---|---|---|---|---|---|---|---|
| CAMTA1 | rs6577393 | rs6657847 | 0.51 | T | 0.391 | 0.04251 | 2.04 |
| CAMTA1 | rs6577401 | rs6698901 | 0.59 | G | 0.641 | 0.03272 | 2.03 |
| RP1-21O18.1 | rs4661572 | rs4501834 | 0.60 | C | 0.242 | 0.02391 | 2.68 |
| CACNA1E | rs199960 | rs1953690 | 0.81 | A | 0.422 | 0.04061 | 2.01 |
| CAMK1G | rs9430004 | rs9430004 | N/A | T | 0.563 | 0.01262 | 2.27 |
| KCNH1 | rs1393026 | rs7529770 | 0.52 | G | 0.323 | 0.01484 | 0.44 |
| KCNH1 | rs1770220 | rs1777256 | 1.00 | A | 0.266 | 0.007082 | 0.39 |
| ANK3 | rs3750800 | rs3750800 | N/A | A | 0.281 | 0.03529 | 0.48 |
| TOLLIP | rs3168046 | rs2672812 | 0.85 | G | 0.375 | 0.03841 | 0.51 |
| TOLLIP | rs3750920 | rs2672812 | 0.85 | G | 0.375 | 0.03841 | 0.51 |
| HCCA2 | rs7396514 | rs10734456 | 0.55 | C | 0.141 | 0.03102 | 0.41 |
| DUSP8 | rs10734456 | rs10734456 | N/A | C | 0.141 | 0.03102 | 0.41 |
| DUSP8 | rs902224 | rs10734456 | 0.74 | C | 0.141 | 0.03102 | 0.41 |
| KCNC1 | rs10766434 | rs10766426 | 0.78 | G | 0.484 | 0.01735 | 2.21 |
| KCNC1 | rs2299637 | rs10766426 | 0.56 | G | 0.484 | 0.01735 | 2.21 |
| KCNC1 | rs757514 | rs10766426 | 0.78 | G | 0.484 | 0.01735 | 2.21 |
| SERGEF | rs172424 | rs2299628 | 0.65 | G | 0.281 | 0.02554 | 0.46 |
| SERGEF | rs211130 | rs2299628 | 0.65 | G | 0.281 | 0.02554 | 0.46 |
| SERGEF | rs211137 | rs2299628 | 0.65 | G | 0.281 | 0.02554 | 0.46 |
| SERGEF | rs211146 | rs2299628 | 1.00 | G | 0.281 | 0.02554 | 0.46 |
| SERGEF | rs2283233 | rs2299628 | 1.00 | G | 0.281 | 0.02554 | 0.46 |
| SERGEF | rs1528 | rs1528 | N/A | C | 0.188 | 0.007483 | 4.11 |
| SERGEF | rs2283233 | rs2283233 | N/A | C | 0.274 | 0.02958 | 0.47 |
| NAV2 | rs2585788 | rs2625312 | 0.84 | A | 0.203 | 0.04449 | 0.47 |
| SLC17A6 | rs1979072 | rs11026546 | 1.00 | A | 0.250 | 0.009104 | 3.15 |
| SLC17A6 | rs1979073 | rs11026546 | 1.00 | A | 0.250 | 0.009104 | 3.15 |
| SLC17A6 | rs2593644 | rs11026546 | 0.88 | A | 0.250 | 0.009104 | 3.15 |
| SLC17A6 | rs764021 | rs721840 | 0.97 | C | 0.242 | 0.02368 | 0.44 |
| PHACS | rs3107275 | rs3134907 | 0.79 | C | 0.203 | 0.02318 | 0.43 |
| KIAA1853 | rs1568923 | rs10851061 | 0.58 | G | 0.188 | 0.03528 | 0.45 |
| KIAA1545 | rs10870551 | rs4418881 | 1.00 | G | 0.234 | 0.0243 | 0.44 |
| KIAA1545 | rs4883513 | rs4883513 | N/A | T | 0.233 | 0.01119 | 0.40 |
| RTN1 | rs17255975 | rs1884737 | 0.75 | G | 0.234 | 0.01716 | 2.89 |
| UNC13C | rs11856476 | rs8024165 | 0.84 | T | 0.438 | 0.01674 | 2.27 |
| UNC13C | rs12914912 | rs8024165 | 0.63 | T | 0.438 | 0.01674 | 2.27 |
| UNC13C | rs4776216 | rs8024165 | 0.52 | T | 0.438 | 0.01674 | 2.27 |
| UNC13C | rs9920139 | rs9920150 | 0.91 | G | 0.047 | 0.04211 | 0.28 |
| UNC13C | rs9920150 | rs9920150 | N/A | G | 0.047 | 0.04211 | 0.28 |
| NEDD4 | rs1509408 | rs1509408 | N/A | C | 0.281 | 0.03119 | 2.38 |
| GRINL1A | rs16977631 | rs11638184 | 0.52 | A | 0.063 | 0.004306 | 0.22 |
| GCOM1 | rs2733619 | rs2733619 | N/A | C | 0.016 | 0.04231 | 0.15 |
| AKAP13 | rs338556 | rs8025135 | 0.71 | G | 0.297 | 0.0149 | 2.63 |
| KLHL25 | rs2430838 | rs8025135 | 0.64 | G | 0.297 | 0.0149 | 2.63 |
| SLCO3A1 | rs2286355 | rs11630872 | 0.85 | T | 0.422 | 0.01222 | 2.39 |
| SLCO3A1 | rs6496893 | rs11638063 | 1.00 | A | 0.047 | 0.04211 | 0.28 |
| CBLN1 | rs11076478 | rs893175 | 0.53 | C | 0.484 | 0.007589 | 2.46 |

TABLE 8-continued

Alleles Affecting Positive Response to Perphenazine

| Gene Name | Table B SNP | Test SNP in linkage disequilibrium | r² | Allele | Frequency in responders | P | OR |
|---|---|---|---|---|---|---|---|
| CBLN1 | rs3743777 | rs8052939 | 0.89 | G | 0.094 | 0.01269 | 9.62 |
| CBLN1 | rs9935379 | rs893175 | 0.69 | C | 0.484 | 0.007589 | 2.46 |
| CDH11 | rs35144 | rs35164 | 0.68 | T | 0.145 | 0.04592 | 0.43 |
| CDH11 | rs35148 | rs35164 | 1.00 | T | 0.145 | 0.04592 | 0.43 |
| BEAN | rs11644279 | rs11075635 | 0.59 | C | 0.266 | 0.02787 | 2.47 |
| COX10 | rs4792434 | rs8077302 | 0.55 | G | 0.597 | 0.01289 | 2.28 |
| COX10 | rs8077302 | rs8077302 | N/A | G | 0.597 | 0.01289 | 2.28 |
| KATNAL2 | rs2247221 | rs4986203 | 0.53 | A | 0.468 | 0.04996 | 1.95 |
| KATNAL2 | rs2571030 | rs4986203 | 0.53 | A | 0.468 | 0.04996 | 1.95 |
| KATNAL2 | rs9961383 | rs4986203 | 0.53 | A | 0.468 | 0.04996 | 1.95 |
| FUSSEL18 | rs10502880 | rs11082575 | 0.55 | G | 0.339 | 0.01242 | 0.43 |
| FUSSEL18 | rs17785419 | rs11082575 | 0.55 | G | 0.339 | 0.01242 | 0.43 |
| FUSSEL18 | rs2668771 | rs9965170 | 0.56 | A | 0.406 | 0.02724 | 0.49 |
| FUSSEL18 | rs7236105 | rs9965170 | 0.88 | A | 0.406 | 0.02724 | 0.49 |
| DCC | rs12457407 | rs9949949 | 0.83 | A | 0.453 | 0.03236 | 2.06 |
| DCC | rs1893572 | rs7228674 | 0.77 | T | 0.156 | 0.03404 | 0.42 |
| DCC | rs4940251 | rs9949949 | 0.82 | A | 0.453 | 0.03236 | 2.06 |
| DCC | rs7506904 | rs9949949 | 0.93 | A | 0.453 | 0.03236 | 2.06 |
| BMP7 | rs230198 | rs230191 | 0.97 | T | 0.406 | 0.02724 | 0.49 |
| TMEPAI | rs6015068 | rs6015068 | N/A | T | 0.484 | 0.01161 | 2.33 |

TABLE 9

Alleles Affecting Negative Side Effects for Perphenazine

| Gene Name | Table B SNP | Test SNP in linkage disequilibrium | r² | Allele | Frequency in discontinuers | P | OR |
|---|---|---|---|---|---|---|---|
| CAMTA1 | rs12070592 | rs9434833 | 1.00 | T | 0.333 | 0.02671 | 2.92 |
| SLC6A17 | rs924181 | rs1571346 | 0.64 | G | 0.583 | 0.03113 | 2.59 |
| KCNC4 | rs11578913 | rs11578913 | N/A | A | 0.167 | 0.04276 | 0.33 |
| SLC16A4 | rs10857820 | rs3768458 | 0.65 | T | 0.625 | 0.04343 | 2.47 |
| SLC16A4 | rs1334882 | rs3768458 | 1.00 | T | 0.625 | 0.04343 | 2.47 |
| CAMK1G | rs11119315 | rs11119315 | N/A | A | 0.292 | 0.02755 | 3.04 |
| CAMK1G | rs6690557 | rs713075 | 0.80 | A | 0.500 | 0.02324 | 2.72 |
| KCNH1 | rs1770220 | rs10863854 | 0.65 | T | 0.292 | 0.04383 | 0.39 |
| TOLLIP | rs3168046 | rs2014486 | 0.85 | A | 0.667 | 0.0345 | 2.62 |
| TOLLIP | rs3750920 | rs2014486 | 0.85 | A | 0.667 | 0.0345 | 2.62 |
| OTOG | rs2041028 | rs734640 | 0.55 | G | 0.083 | 0.03774 | 0.23 |
| OTOG | rs2355466 | rs734640 | 0.55 | G | 0.083 | 0.03774 | 0.23 |
| OTOG | rs4757548 | rs734640 | 0.50 | G | 0.083 | 0.03774 | 0.23 |
| OTOG | rs7111528 | rs734640 | 0.55 | G | 0.083 | 0.03774 | 0.23 |
| SERGEF | rs172424 | rs4141243 | 0.65 | C | 0.625 | 0.009037 | 3.19 |
| SERGEF | rs211130 | rs4141243 | 0.65 | C | 0.625 | 0.009037 | 3.19 |
| SERGEF | rs211137 | rs4141243 | 0.65 | C | 0.625 | 0.009037 | 3.19 |
| SERGEF | rs211146 | rs4141243 | 1.00 | C | 0.625 | 0.009037 | 3.19 |
| SERGEF | rs2283233 | rs4141243 | 1.00 | C | 0.625 | 0.009037 | 3.19 |
| SERGEF | rs2283233 | rs2283233 | N/A | C | 0.583 | 0.02427 | 2.71 |
| PTPN5 | rs4274187 | rs4075664 | 0.67 | C | 0.667 | 0.04808 | 2.47 |
| HSD17B12 | rs1061810 | rs10768983 | 0.87 | G | 0.455 | 0.03089 | 2.72 |
| HSD17B12 | rs4755744 | rs10768983 | 1.00 | G | 0.455 | 0.03089 | 2.72 |
| ZFP91-CNTF | rs1938596 | rs2509920 | 0.97 | C | 0.625 | 0.04343 | 2.47 |
| ZFP91-CNTF | rs4319530 | rs2509920 | 0.90 | C | 0.625 | 0.04343 | 2.47 |
| KIAA1545 | rs10870551 | rs4418881 | 1.00 | G | 0.542 | 0.01977 | 2.80 |
| EML1 | rs2250718 | rs3783322 | 0.70 | G | 0.250 | 0.02801 | 0.34 |
| UNC13C | rs11639005 | rs7163424 | 0.62 | T | 0.167 | 0.03824 | 0.32 |
| UNC13C | rs12914912 | rs12912762 | 0.71 | A | 0.591 | 0.0436 | 2.53 |
| UNC13C | rs4776216 | rs12912762 | 0.77 | A | 0.591 | 0.0436 | 2.53 |
| UNC13C | rs9302181 | rs7163424 | 0.64 | T | 0.167 | 0.03824 | 0.32 |
| AKAP13 | rs16977252 | rs17623915 | 0.75 | C | 0.375 | 0.005111 | 3.73 |
| KLHL25 | rs2554 | rs17623915 | 0.62 | C | 0.375 | 0.005111 | 3.73 |
| SLCO3A1 | rs12912997 | rs12912997 | N/A | G | 0.542 | 0.02862 | 2.62 |
| IGF1R | rs11247380 | rs7165181 | 0.55 | G | 0.292 | 0.04586 | 2.74 |
| IGF1R | rs1879613 | rs7165181 | 0.96 | G | 0.292 | 0.04586 | 2.74 |
| CDH8 | rs11075445 | rs11075445 | N/A | G | 0.208 | 0.02023 | 0.31 |
| CDH8 | rs1369918 | rs11075445 | 1.00 | G | 0.208 | 0.02023 | 0.31 |
| CDH8 | rs1978796 | rs11075445 | 1.00 | G | 0.208 | 0.02023 | 0.31 |
| CDH8 | rs6498807 | rs11075445 | 0.80 | G | 0.208 | 0.02023 | 0.31 |
| CDH8 | rs9939991 | rs4784163 | 0.55 | G | 0.167 | 0.04276 | 0.33 |
| KIAA0513 | rs3794684 | rs3794682 | 0.69 | A | 0.250 | 0.03871 | 0.36 |

TABLE 9-continued

Alleles Affecting Negative Side Effects for Perphenazine

| Gene Name | Table B SNP | Test SNP in linkage disequilibrium | r² | Allele | Frequency in discontinuers | P | OR |
|---|---|---|---|---|---|---|---|
| KIAA0513 | rs4783121 | rs715707 | 1.00 | A | 0.125 | 0.01543 | 6.24 |
| KIAA0513 | rs4783121 | rs4783121 | N/A | A | 0.125 | 0.03696 | 4.64 |
| COX10 | rs2302107 | rs1003060 | 0.89 | T | 0.042 | 0.0156 | 0.12 |
| FUSSEL18 | rs10502880 | rs17785419 | 1.00 | A | 0.292 | 0.02612 | 0.35 |
| FUSSEL18 | rs17785419 | rs17785419 | N/A | A | 0.292 | 0.02612 | 0.35 |
| FUSSEL18 | rs2668771 | rs17785419 | 0.54 | A | 0.292 | 0.02612 | 0.35 |
| FUSSEL18 | rs7236105 | rs17785419 | 0.85 | A | 0.292 | 0.02612 | 0.35 |
| FUSSEL18 | rs892583 | rs892583 | N/A | G | 0.500 | 0.001787 | 3.96 |
| DYM | rs8096141 | rs16950298 | 0.61 | C | 0.167 | 0.04251 | 3.63 |
| DCC | rs6508145 | rs1031062 | 0.67 | G | 0.250 | 0.02271 | 3.39 |

Example 6

Novel Markers Associated with Ziprasidone Response

To assess drug response, the last observation for each patient in treatment Phase 1 of the CATIE trial was used as a primary assessment of efficacy. The standard FDA registration trial definition of response of ≥20% decrease in Positive and Negative Syndrome Scale (PANSS Total Score) was used to assign subjects to a response category. Individuals having composite ordinal effectiveness outcome (COMPEFF) scores of 1 of 2, indicating efficacy, were combined as were those with scores of 3 or 4, indicating lack of efficacy (Davis et al., Schizophr. Bull. 29:73-80 (2003)). The side effects category consisted of individuals discontinued for safety concerns (COMPEFF score 5).

Genetic analysis to document the influence of haplotypes on ziprasidone response was performed using as described in Example 2 with the PLINK 1.03 whole genome analysis toolset developed by Purcell and coworkers (Purcell et al., Am. J. Hum. Genet. 81:559-575 (2007)). PLINK calculates P values for the allele-specific chi-squared test and the odds ratio (OR; or relative risk) associated with the minor allele.

Confirmation of SNP Effects on Ziprasidone Response and Side Effects:

Tables 10 and 11 report the minor allele frequencies, P values, and ORs for SNPs, in Tables B and C that affect ziprasidone response and side effect rates, respectively. Note in Tables 10 and 11 that haplotype blocks result in the same Test SNP being in linkage disequilibrium with multiple SNPs in Table B. Similarly, haplotype blocks result in multiple Test SNPs that can be used for each SNP listed in Table B, though such redundant examples are not presented in Tables 10 and 11.

Tables 10 and 11, provide numerous examples of SNP-based alleles that predict altered response to ziprasidone. For Table 10, ORs of >1.0 indicate that the minor SNP allele is associated with greater clinical improvement, and ORs of <1.0 indicate that the minor SNP allele is associated with lesser clinical improvement. For Table 11 ORs of >1.0 indicate that the minor SNP allele is associated with an increase in study ending side effects, and ORs of <1.0 indicate that the minor SNP allele is associated a decrease in study ending side effects.

TABLE 10

Alleles Affecting Positive Response to Ziprasidone

| Gene Name | Table B SNP | Test SNP in linkage disequilibrium | r2 | Allele | Frequency in responders | P | OR |
|---|---|---|---|---|---|---|---|
| RP1-21O18.1 | rs2073091 | rs761288 | 0.69 | C | 0.235 | 0.0481 | 0.40 |
| RP1-21O18.1 | rs4661572 | rs761288 | 0.56 | C | 0.235 | 0.0481 | 0.40 |
| KCND3 | rs4838924 | rs1373291 | 0.86 | T | 0.147 | 0.03358 | 0.32 |
| RABGAP1L | rs16847624 | rs10912854 | 0.84 | C | 0.125 | 0.03253 | 0.29 |
| RABGAP1L | rs6425302 | rs10912854 | 0.96 | C | 0.125 | 0.03253 | 0.29 |
| CACNA1E | rs199960 | rs3856093 | 0.51 | C | 0.206 | 0.0147 | 0.31 |
| CACNA1E | rs3856090 | rs3856093 | 1.00 | C | 0.206 | 0.0147 | 0.31 |
| CACNA1E | rs506947 | rs16857457 | 0.93 | G | 0.219 | 0.009356 | 5.69 |
| DPH3 | rs2245721 | rs842264 | 0.57 | T | 0.618 | 0.03373 | 2.49 |
| DPH3 | rs842257 | rs842264 | 0.57 | T | 0.618 | 0.03373 | 2.49 |
| DPH3 | rs859703 | rs842264 | 0.57 | T | 0.618 | 0.03373 | 2.49 |
| EXOC2 | rs2294660 | rs2073008 | 0.54 | T | 0.000 | 0.008039 | 0.00 |
| EXOC2 | rs998777 | rs2073008 | 0.74 | T | 0.000 | 0.008039 | 0.00 |
| BRSK2 | rs1554857 | rs7396009 | 0.81 | T | 0.529 | 0.04022 | 2.41 |
| HCCA2 | rs7396514 | rs7396009 | 1.00 | T | 0.529 | 0.04022 | 2.41 |
| HCCA2 | rs7945160 | rs7396009 | 0.55 | T | 0.529 | 0.04022 | 2.41 |
| HCCA2 | rs9440 | rs7396009 | 0.55 | T | 0.529 | 0.04022 | 2.41 |
| DUSP8 | rs10734456 | rs7396009 | 0.55 | T | 0.529 | 0.04022 | 2.41 |
| DUSP8 | rs902224 | rs7396009 | 0.81 | T | 0.529 | 0.04022 | 2.41 |
| KCNQ1 | rs231348 | rs231348 | N/A | T | 0.294 | 0.003769 | 5.08 |
| OTOG | rs11024357 | rs11024357 | N/A | C | 0.353 | 0.03601 | 2.73 |
| OTOG | rs11024358 | rs11024357 | 1.00 | C | 0.353 | 0.03601 | 2.73 |
| PTPN5 | rs4757707 | rs11024786 | 0.64 | T | 0.471 | 0.01003 | 3.18 |

TABLE 10-continued

Alleles Affecting Positive Response to Ziprasidone

| Gene Name | Table B SNP | Test SNP in linkage disequilibrium | r2 | Allele | Frequency in responders | P | OR |
|---|---|---|---|---|---|---|---|
| NAV2 | rs7125647 | rs2119981 | 0.61 | A | 0.618 | 0.01558 | 2.83 |
| SLC6A5 | rs2001982 | rs7950354 | 0.57 | C | 0.147 | 0.02376 | 0.30 |
| LRRC4C | rs2953310 | rs2953310 | N/A | C | 0.235 | 0.01582 | 0.33 |
| HSD17B12 | rs1061810 | rs17596617 | 0.54 | T | 0.147 | 0.02376 | 0.30 |
| HSD17B12 | rs10838160 | rs938942 | 0.59 | T | 0.618 | 0.04616 | 2.36 |
| HSD17B12 | rs3802891 | rs938942 | 0.59 | T | 0.618 | 0.04616 | 2.36 |
| HSD17B12 | rs4755744 | rs17596617 | 0.65 | T | 0.147 | 0.02376 | 0.30 |
| ZFP91-CNTF | rs1938596 | rs2509920 | 0.97 | C | 0.559 | 0.04351 | 2.37 |
| ZFP91-CNTF | rs4319530 | rs2509920 | 0.90 | C | 0.559 | 0.04351 | 2.37 |
| DTX4 | rs1048444 | rs544864 | 0.55 | T | 0.147 | 0.03358 | 0.32 |
| DTX4 | rs2211912 | rs2211912 | N/A | A | 0.353 | 0.03477 | 0.40 |
| DTX4 | rs3847 | rs544864 | 0.55 | T | 0.147 | 0.03358 | 0.32 |
| DTX4 | rs5029315 | rs2211912 | 1.00 | A | 0.353 | 0.03477 | 0.40 |
| DTX4 | rs544864 | rs544864 | N/A | T | 0.147 | 0.03358 | 0.32 |
| DTX4 | rs621162 | rs544864 | 1.00 | T | 0.147 | 0.03358 | 0.32 |
| DTX4 | rs656163 | rs2211912 | 0.88 | A | 0.353 | 0.03477 | 0.40 |
| TTC5 | rs10873395 | rs8022565 | 0.77 | C | 0.441 | 0.02702 | 2.68 |
| TTC5 | rs2318864 | rs8022565 | 0.73 | C | 0.441 | 0.02702 | 2.68 |
| TTC5 | rs3742945 | rs8022565 | 0.73 | C | 0.441 | 0.02702 | 2.68 |
| TTC5 | rs2318864 | rs2318864 | N/A | G | 0.441 | 0.04178 | 2.47 |
| TEP1 | rs1713449 | rs1760909 | 0.96 | T | 0.059 | 0.01999 | 0.19 |
| TEP1 | rs7150689 | rs1760909 | 0.87 | T | 0.059 | 0.01999 | 0.19 |
| TEP1 | rs938886 | rs1760909 | 1.00 | T | 0.059 | 0.01999 | 0.19 |
| TEP1 | rs938887 | rs1760909 | 0.67 | T | 0.059 | 0.01999 | 0.19 |
| TEP1 | rs1713449 | rs1713449 | N/A | T | 0.059 | 0.02358 | 0.20 |
| DAAM1 | rs1252989 | rs1957409 | 0.94 | A | 0.250 | 0.01917 | 0.33 |
| DAAM1 | rs1253005 | rs1957409 | 1.00 | A | 0.250 | 0.01917 | 0.33 |
| DAAM1 | rs1268579 | rs2053298 | 1.00 | T | 0.441 | 0.04178 | 2.47 |
| DAAM1 | rs4901909 | rs1957409 | 0.62 | A | 0.250 | 0.01917 | 0.33 |
| DAAM1 | rs8022614 | rs1957409 | 0.71 | A | 0.250 | 0.01917 | 0.33 |
| DAAM1 | rs941884 | rs1957409 | 0.72 | A | 0.250 | 0.01917 | 0.33 |
| EML1 | rs11160553 | rs8013843 | 0.71 | T | 0.059 | 0.0113 | 0.17 |
| EML1 | rs11160563 | rs8020741 | 0.68 | T | 0.235 | 0.02281 | 0.35 |
| EML1 | rs12433613 | rs8013843 | 0.60 | T | 0.059 | 0.0113 | 0.17 |
| EML1 | rs6575751 | rs8013843 | 0.71 | T | 0.059 | 0.0113 | 0.17 |
| WDR25 | rs10873518 | rs11160589 | 1.00 | T | 0.529 | 0.03593 | 2.48 |
| UNC13C | rs12910912 | rs12910912 | N/A | G | 0.382 | 0.001068 | 5.22 |
| ADAM10 | rs4775086 | rs7161889 | 0.55 | C | 0.382 | 0.02825 | 2.79 |
| ADAM10 | rs514049 | rs7161889 | 0.70 | C | 0.382 | 0.02825 | 2.79 |
| ADAM10 | rs653765 | rs7161889 | 0.79 | C | 0.382 | 0.02825 | 2.79 |
| AKAP13 | rs2291049 | rs10520596 | 0.59 | G | 0.206 | 0.0113 | 5.44 |
| AKAP13 | rs338556 | rs8025135 | 0.71 | G | 0.059 | 0.02358 | 0.20 |
| KLHL25 | rs2430838 | rs8025135 | 0.64 | G | 0.059 | 0.02358 | 0.20 |
| KLHL25 | rs2554 | rs10520595 | 0.50 | T | 0.353 | 0.02633 | 2.95 |
| SV2B | rs11630131 | rs6496778 | 0.55 | G | 0.441 | 0.01303 | 3.10 |
| SV2B | rs2073967 | rs6496778 | 0.87 | G | 0.441 | 0.01303 | 3.10 |
| IGF1R | rs11247380 | rs4966036 | 0.55 | C | 0.265 | 0.02113 | 3.60 |
| IGF1R | rs1879613 | rs4966036 | 0.96 | C | 0.265 | 0.02113 | 3.60 |
| IGF1R | rs8030950 | rs1879612 | 0.66 | C | 0.559 | 0.005 | 3.38 |
| CBLN1 | rs11076478 | rs1469906 | 0.72 | A | 0.206 | 0.004634 | 0.26 |
| CBLN1 | rs9935379 | rs1469906 | 0.90 | A | 0.206 | 0.004634 | 0.26 |
| CBLN1 | rs9935379 | rs9935379 | N/A | G | 0.206 | 0.02119 | 0.33 |
| CDH8 | rs11075445 | rs11075445 | N/A | G | 0.559 | 0.02987 | 2.53 |
| CDH8 | rs1369918 | rs11075445 | 1.00 | G | 0.559 | 0.02987 | 2.53 |
| CDH8 | rs1978796 | rs11075445 | 1.00 | G | 0.559 | 0.02987 | 2.53 |
| CDH8 | rs6498807 | rs1397126 | 0.51 | G | 0.281 | 0.007855 | 4.62 |
| CDH8 | rs9939991 | rs6498806 | 0.65 | A | 0.294 | 0.004701 | 4.92 |
| CDH11 | rs35144 | rs4967886 | 0.65 | A | 0.265 | 0.007512 | 0.30 |
| CDH11 | rs35148 | rs35164 | 1.00 | T | 0.177 | 0.02306 | 0.32 |
| CDH11 | rs35186 | rs35216 | 0.56 | G | 0.250 | 0.03882 | 0.38 |
| KIAA0513 | rs12597135 | rs8063083 | 0.53 | C | 0.559 | 0.04351 | 2.37 |
| KIAA0513 | rs3751756 | rs8063083 | 0.60 | C | 0.559 | 0.04351 | 2.37 |
| KIAA0182 | rs3815794 | rs1053328 | 0.73 | T | 0.382 | 0.04528 | 2.52 |
| FUSSEL18 | rs892583 | rs11877471 | 0.68 | G | 0.441 | 0.04178 | 2.47 |
| KIAA0427 | rs4939813 | rs9959212 | 0.66 | A | 0.294 | 0.03491 | 0.39 |
| DCC | rs1431748 | rs7504750 | 0.63 | C | 0.412 | 0.03518 | 2.60 |
| TMEPAI | rs427278 | rs203386 | 0.51 | C | 0.294 | 0.01685 | 0.35 |

TABLE 11

Alleles Affecting Negative Side Effects for Ziprasidone

| Gene Name | Table B SNP | Test SNP in linkage disequilibrium | $r^2$ | Allele | Frequency in discontinuers | P | OR |
|---|---|---|---|---|---|---|---|
| RERE | rs3753275 | rs4581300 | 0.72 | T | 0.292 | 0.01404 | 4.06 |
| SLC6A17 | rs1010892 | rs17671169 | 0.70 | A | 0.708 | 0.02545 | 3.02 |
| SLC6A17 | rs6689641 | rs17671169 | 0.82 | A | 0.708 | 0.02545 | 3.02 |
| SLC6A17 | rs877068 | rs17671169 | 0.60 | A | 0.708 | 0.02545 | 3.02 |
| SLC6A17 | rs924181 | rs17671169 | 0.53 | A | 0.708 | 0.02545 | 3.02 |
| DNM3 | rs10752946 | rs9425598 | 1.00 | A | 0.583 | 0.01857 | 3.03 |
| CACNA1E | rs199960 | rs3856093 | 0.51 | C | 0.542 | 0.04571 | 2.56 |
| CACNA1E | rs3856090 | rs3856093 | 1.00 | C | 0.542 | 0.04571 | 2.56 |
| KCNH1 | rs11119658 | rs1875438 | 0.59 | C | 0.292 | 0.04465 | 0.37 |
| KCNH1 | rs1393026 | rs7529770 | 0.52 | G | 0.625 | 0.01287 | 3.27 |
| KCNH1 | rs1501569 | rs1501555 | 0.56 | G | 0.667 | 0.01802 | 3.14 |
| OTOG | rs2073582 | rs972676 | 0.71 | A | 0.250 | 0.04192 | 0.35 |
| NAV2 | rs1372989 | rs1982265 | 0.54 | G | 0.000 | 0.02984 | 0.00 |
| SLC6A5 | rs2001982 | rs7950354 | 0.57 | C | 0.458 | 0.0371 | 2.73 |
| SYT13 | rs4992029 | rs7117240 | 0.55 | C | 0.542 | 0.03343 | 2.72 |
| SYT13 | rs8929 | rs7117240 | 0.54 | C | 0.542 | 0.03343 | 2.72 |
| CHFR | rs2306536 | rs4758911 | 0.94 | C | 0.458 | 0.005139 | 3.97 |
| CHFR | rs4758954 | rs4758911 | 0.94 | C | 0.458 | 0.005139 | 3.97 |
| RTN1 | rs17255975 | rs1884737 | 0.75 | G | 0.333 | 0.04006 | 2.96 |
| UNC13C | rs11639005 | rs8025195 | 0.81 | G | 0.208 | 0.04687 | 0.34 |
| UNC13C | rs12594549 | rs1864416 | 0.85 | A | 0.250 | 0.004958 | 6.00 |
| UNC13C | rs8025195 | rs8025195 | N/A | G | 0.208 | 0.04687 | 0.34 |
| UNC13C | rs9302181 | rs8025195 | 0.78 | G | 0.208 | 0.04687 | 0.34 |
| AKAP13 | rs16977252 | rs16949988 | 0.56 | T | 0.583 | 0.01303 | 3.23 |
| AKAP13 | rs338556 | rs2241269 | 0.54 | T | 0.458 | 0.0371 | 2.73 |
| SV2B | rs1075840 | rs6496780 | 0.74 | G | 0.167 | 0.04248 | 0.31 |
| SV2B | rs11630131 | rs17516708 | 0.66 | T | 0.000 | 0.02337 | 0.00 |
| SV2B | rs2073967 | rs17516708 | 0.55 | T | 0.000 | 0.02337 | 0.00 |
| SV2B | rs2301665 | rs6496780 | 0.87 | G | 0.167 | 0.04248 | 0.31 |
| NETO2 | rs11859615 | rs9928466 | 0.85 | C | 0.125 | 0.01646 | 10.43 |
| NETO2 | rs16952126 | rs9928466 | 0.85 | C | 0.125 | 0.01646 | 10.43 |
| NETO2 | rs7184206 | rs9928466 | 1.00 | C | 0.125 | 0.01646 | 10.43 |
| NETO2 | rs9923731 | rs9928466 | 0.85 | C | 0.125 | 0.01646 | 10.43 |
| CBLN1 | rs11076478 | rs12598711 | 0.89 | G | 0.458 | 0.004068 | 4.10 |
| CBLN1 | rs9935379 | rs12598711 | 0.72 | G | 0.458 | 0.004068 | 4.10 |
| CDH11 | rs35144 | rs4967886 | 0.65 | A | 0.625 | 0.04807 | 2.56 |
| PMP22 | rs179521 | rs2323653 | 0.88 | A | 0.458 | 0.0371 | 2.73 |
| FUSSEL18 | rs10502880 | rs11663646 | 0.55 | T | 0.583 | 0.04765 | 2.54 |
| FUSSEL18 | rs17785419 | rs11663646 | 0.55 | T | 0.583 | 0.04765 | 2.54 |
| DCC | rs4940251 | rs4940259 | 0.51 | A | 0.500 | 0.03013 | 2.80 |
| DCC | rs6508235 | rs4940259 | 1.00 | A | 0.500 | 0.03013 | 2.80 |

Example 7

Novel Markers Associated with Overall Response

To assess drug response, the last observation for each patient in treatment Phase 1 of the CATIE trial was used as a primary assessment of efficacy. The standard FDA registration trial definition of response of ≥20% decrease in Positive and Negative Syndrome Scale (PANSS Total Score) was used to assign subjects to a response category. Individuals having composite ordinal effectiveness outcome (COMPEFF) scores of 1 of 2, indicating efficacy, were combined as were those with scores of 3 or 4, indicating lack of efficacy (Davis et al., Schizophr. Bull. 29:73-80 (2003)). The side effects category consisted of individuals discontinued for safety concerns (COMPEFF score 5).

Genetic analysis to document the influence of haplotypes on overall response regardless of the drug used was performed using as described in Example 2 with the PLINK 1.03 whole genome analysis toolset developed by Purcell and coworkers (Purcell et al., Am. J. Hum. Genet. 81:559-575 (2007)). PLINK calculates P values for the allele-specific chi-squared test and the odds ratio (OR; or relative risk) associated with the minor allele.

Confirmation of SNP Effects on Overall Response and Side Effects for All Drugs:

Tables 12 and 13 report the minor allele frequencies, P values, and ORs for SNPs, in Tables B and C that affect overall response for all drugs combined and side effect rates for all drugs combined, respectively; for a combined sample set of patients treated with the drugs described in Examples 2 through 6. Note in Tables 12 and 13 that haplotype blocks result in the same Test SNP being in linkage disequilibrium with multiple SNPs in Table B. Similarly, haplotype blocks result in multiple Test SNPs that can be used for each SNP listed in Table B, though such redundant examples are not presented in Tables 12 and 13.

Tables 12 and 13, provide numerous examples of SNP-based alleles that predict altered response for all drugs combined (see Examples 2 through 6). For Table 12, ORs of >1.0 indicate that the minor SNP allele is associated with greater clinical improvement, and ORs of <1.0 indicate that the minor SNP allele is associated with lesser clinical improvement. For Table 13 ORs of >1.0 indicate that the minor SNP allele is associated with an increase in study ending side effects, and ORs of <1.0 indicate that the minor SNP allele is associated a decrease in study ending side effects.

TABLE 12

Alleles Affecting Positive Response to For All Drugs Combined

| Gene Name | Table B SNP | Test SNP in linkage disequilibrium | $r^2$ | Allele | Frequency in responders | P | OR |
|---|---|---|---|---|---|---|---|
| PRDM2 | rs1203682 | rs1203682 | N/A | C | 0.159 | 0.04025 | 0.67 |
| SLC6A17 | rs1010892 | rs6689641 | 0.87 | A | 0.387 | 0.02751 | 0.72 |
| SLC6A17 | rs6689641 | rs6689641 | N/A | A | 0.387 | 0.02751 | 0.72 |
| SLC6A17 | rs877068 | rs6689641 | 0.75 | A | 0.387 | 0.02751 | 0.72 |
| KCND3 | rs11102342 | rs1538388 | 0.90 | A | 0.451 | 0.0118 | 1.45 |
| DNM3 | rs10752946 | rs9425598 | 1.00 | A | 0.468 | 0.02928 | 1.38 |
| DNM3 | rs4382763 | rs6701929 | 0.84 | C | 0.199 | 0.01233 | 0.64 |
| KCNH1 | rs1770220 | rs1777256 | 1.00 | A | 0.331 | 0.03394 | 0.72 |
| EXOC2 | rs2493037 | rs2473484 | 1.00 | C | 0.171 | 0.02535 | 1.58 |
| USH1C | rs1055574 | rs4756895 | 0.52 | T | 0.518 | 0.02037 | 1.40 |
| USH1C | rs1055577 | rs4756895 | 0.52 | T | 0.518 | 0.02037 | 1.40 |
| USH1C | rs16770 | rs2237961 | 0.92 | C | 0.067 | 0.01527 | 0.52 |
| USH1C | rs2072225 | rs4756895 | 0.64 | T | 0.518 | 0.02037 | 1.40 |
| USH1C | rs4756895 | rs4756895 | N/A | T | 0.518 | 0.02037 | 1.40 |
| LRRC4C | rs2953310 | rs2953310 | N/A | C | 0.338 | 0.02054 | 0.70 |
| HSD17B12 | rs1061810 | rs10838184 | 0.65 | C | 0.222 | 0.04552 | 0.71 |
| HSD17B12 | rs10838160 | rs7482725 | 0.62 | A | 0.514 | 0.03771 | 1.36 |
| HSD17B12 | rs3802891 | rs7482725 | 0.62 | A | 0.514 | 0.03771 | 1.36 |
| HSD17B12 | rs4755744 | rs10838184 | 0.72 | C | 0.222 | 0.04552 | 0.71 |
| KIAA1853 | rs6490226 | rs7966721 | 0.53 | G | 0.436 | 0.01646 | 1.43 |
| KIAA1545 | rs7294615 | rs4242909 | 0.60 | C | 0.407 | 0.03532 | 0.73 |
| JPH4 | rs12897422 | rs12897422 | N/A | A | 0.159 | 0.02094 | 1.64 |
| DAAM1 | rs1252989 | rs8004164 | 0.91 | A | 0.372 | 0.02642 | 0.72 |
| DAAM1 | rs1253005 | rs8004164 | 0.97 | A | 0.372 | 0.02642 | 0.72 |
| DAAM1 | rs4901909 | rs8004164 | 0.60 | A | 0.372 | 0.02642 | 0.72 |
| DAAM1 | rs8022614 | rs8004164 | 0.74 | A | 0.372 | 0.02642 | 0.72 |
| DAAM1 | rs941884 | rs8004164 | 0.69 | A | 0.372 | 0.02642 | 0.72 |
| GPR135 | rs10136708 | rs4898989 | 0.61 | A | 0.450 | 0.02522 | 1.40 |
| GPR135 | rs10138199 | rs4898989 | 1.00 | A | 0.450 | 0.02522 | 1.40 |
| GPR135 | rs1253181 | rs4898989 | 0.81 | A | 0.450 | 0.02522 | 1.40 |
| GPR135 | rs17255731 | rs4898989 | 0.51 | A | 0.450 | 0.02522 | 1.40 |
| GPR135 | rs4898989 | rs4898989 | N/A | A | 0.450 | 0.02522 | 1.40 |
| GPR135 | rs9323348 | rs4898989 | 1.00 | A | 0.450 | 0.02522 | 1.40 |
| RTN1 | rs10145080 | rs17731838 | 0.65 | T | 0.187 | 0.02742 | 0.67 |
| RTN1 | rs12717467 | rs17731838 | 0.52 | T | 0.187 | 0.02742 | 0.67 |
| RTN1 | rs17310036 | rs17731838 | 0.81 | T | 0.187 | 0.02742 | 0.67 |
| EML1 | rs10144785 | rs17099031 | 0.63 | C | 0.197 | 0.0419 | 1.48 |
| UNC13C | rs12910912 | rs12910912 | N/A | G | 0.229 | 0.004504 | 1.68 |
| NEDD4 | rs2271289 | rs12916104 | 0.86 | T | 0.458 | 0.03201 | 1.37 |
| NEDD4 | rs2303579 | rs10518831 | 0.51 | G | 0.183 | 0.01556 | 1.62 |
| NEDD4 | rs2303580 | rs10518831 | 0.51 | G | 0.183 | 0.01556 | 1.62 |
| GRINL1A | rs4774275 | rs1873995 | 0.51 | G | 0.416 | 0.02634 | 0.72 |
| GRINL1A | rs986868 | rs9302201 | 0.90 | C | 0.405 | 0.003219 | 1.56 |
| AKAP13 | rs11073502 | rs2291048 | 0.53 | G | 0.232 | 0.02934 | 0.69 |
| AKAP13 | rs745191 | rs745191 | N/A | T | 0.248 | 0.04875 | 0.72 |
| SV2B | rs1075840 | rs2106692 | 0.52 | A | 0.324 | 0.03372 | 1.40 |
| SV2B | rs1117388 | rs2106692 | 0.61 | A | 0.324 | 0.03372 | 1.40 |
| SV2B | rs11630131 | rs6496778 | 0.55 | G | 0.309 | 0.002113 | 1.66 |
| SV2B | rs2073967 | rs6496778 | 0.87 | G | 0.309 | 0.002113 | 1.66 |
| SV2B | rs2301665 | rs2106692 | 0.56 | A | 0.324 | 0.03372 | 1.40 |
| SV2B | rs11630131 | rs11630131 | N/A | A | 0.211 | 0.03028 | 1.50 |
| RGMA | rs13167 | rs11074130 | 0.59 | T | 0.121 | 0.02593 | 1.72 |
| IGF1R | rs2684808 | rs951715 | 0.51 | G | 0.303 | 0.0154 | 0.69 |
| CDH11 | rs35144 | rs4967886 | 0.65 | A | 0.335 | 0.001908 | 0.62 |
| CDH11 | rs35148 | rs35140 | 0.68 | G | 0.264 | 0.002194 | 0.61 |
| CDH11 | rs35186 | rs35140 | 0.56 | G | 0.264 | 0.002194 | 0.61 |
| CDH11 | rs35195 | rs35195 | N/A | A | 0.271 | 0.003523 | 0.63 |
| CDH11 | rs35144 | rs35144 | N/A | C | 0.279 | 0.006589 | 0.65 |
| CDH11 | rs35186 | rs35186 | N/A | T | 0.419 | 0.02642 | 0.72 |
| FUSSEL18 | rs892583 | rs11877471 | 0.68 | G | 0.377 | 0.01138 | 1.48 |
| FUSSEL18 | rs892583 | rs892583 | N/A | G | 0.323 | 0.02405 | 1.44 |
| SMAD2 | rs12457664 | rs10502890 | 1.00 | T | 0.433 | 0.04215 | 0.74 |
| SMAD2 | rs1787176 | rs10502890 | 0.82 | T | 0.433 | 0.04215 | 0.74 |
| SMAD2 | rs1792666 | rs10502890 | 0.62 | T | 0.433 | 0.04215 | 0.74 |
| SMAD2 | rs1792682 | rs10502890 | 0.79 | T | 0.433 | 0.04215 | 0.74 |
| SMAD2 | rs2000709 | rs10502890 | 0.94 | T | 0.433 | 0.04215 | 0.74 |
| SMAD2 | rs7228393 | rs10502890 | 0.94 | T | 0.433 | 0.04215 | 0.74 |
| SMAD7 | rs736839 | rs2337153 | 0.73 | A | 0.433 | 0.003271 | 1.55 |
| SMAD4 | rs12458752 | rs7243135 | 0.97 | G | 0.451 | 0.04012 | 1.35 |
| SMAD4 | rs12958604 | rs7243135 | 0.97 | G | 0.451 | 0.04012 | 1.35 |
| SMAD4 | rs2276163 | rs7243135 | 0.97 | G | 0.451 | 0.04012 | 1.35 |
| SMAD4 | rs2298617 | rs7243135 | 0.97 | G | 0.451 | 0.04012 | 1.35 |
| SMAD4 | rs3764465 | rs7243135 | 0.97 | G | 0.451 | 0.04012 | 1.35 |
| SMAD4 | rs620898 | rs7243135 | 0.97 | G | 0.451 | 0.04012 | 1.35 |

TABLE 12-continued

Alleles Affecting Positive Response to For All Drugs Combined

| Gene Name | Table B SNP | Test SNP in linkage disequilibrium | r² | Allele | Frequency in responders | P | OR |
|---|---|---|---|---|---|---|---|
| DCC | rs12457407 | rs9949949 | 0.83 | A | 0.426 | 0.00489 | 1.53 |
| DCC | rs1393331 | rs8088048 | 0.78 | C | 0.436 | 0.02862 | 1.39 |
| DCC | rs1431748 | rs7504750 | 0.63 | C | 0.329 | 0.005512 | 1.57 |
| DCC | rs2229080 | rs12605899 | 0.53 | C | 0.422 | 0.03279 | 0.73 |
| DCC | rs4940251 | rs9949949 | 0.82 | A | 0.426 | 0.00489 | 1.53 |
| DCC | rs6508235 | rs9954344 | 0.62 | G | 0.418 | 0.01342 | 1.45 |
| DCC | rs7506904 | rs9949949 | 0.93 | A | 0.426 | 0.00489 | 1.53 |
| DCC | rs950278 | rs12605899 | 0.97 | C | 0.422 | 0.03279 | 0.73 |

TABLE 13

Alleles Increasing Negative Side Effects for All Drugs Combined

| Gene Name | Table B SNP | Test SNP in linkage disequilibrium | r² | Allele | Frequency in discontinuers | P | OR |
|---|---|---|---|---|---|---|---|
| CAMTA1 | rs228651 | rs11121029 | 0.51 | A | 0.154 | 0.0369 | 0.61 |
| RERE | rs6698830 | rs12024032 | 0.90 | C | 0.364 | 0.01972 | 0.66 |
| RERE | rs7530745 | rs12024032 | 0.55 | C | 0.364 | 0.01972 | 0.66 |
| RERE | rs7554486 | rs12024032 | 0.80 | C | 0.364 | 0.01972 | 0.66 |
| KCNA10 | rs1281174 | rs1281177 | 0.60 | A | 0.413 | 0.04816 | 1.43 |
| KCNA10 | rs1281177 | rs1281177 | N/A | A | 0.413 | 0.04816 | 1.43 |
| CACNA1E | rs506947 | rs593413 | 1.00 | A | 0.082 | 0.0313 | 0.52 |
| SYT14 | rs4609425 | rs12029138 | 0.96 | G | 0.414 | 0.03589 | 1.46 |
| EXOC2 | rs2493049 | rs12154040 | 0.54 | C | 0.488 | 0.03739 | 1.44 |
| NAV2 | rs2028570 | rs1867116 | 0.90 | T | 0.500 | 0.02091 | 1.50 |
| NAV2 | rs7125647 | rs2119981 | 0.61 | A | 0.380 | 0.04636 | 0.70 |
| SLC17A6 | rs11026523 | rs2078352 | 0.79 | T | 0.138 | 0.01 | 0.53 |
| SLC17A6 | rs1155821 | rs2078352 | 0.96 | T | 0.138 | 0.01 | 0.53 |
| SLC17A6 | rs2078352 | rs2078352 | N/A | T | 0.138 | 0.01 | 0.53 |
| SLC17A6 | rs2246710 | rs2078352 | 1.00 | T | 0.138 | 0.01 | 0.53 |
| DAAM1 | rs1252989 | rs8004164 | 0.91 | A | 0.513 | 0.01324 | 1.55 |
| DAAM1 | rs1253005 | rs8004164 | 0.97 | A | 0.513 | 0.01324 | 1.55 |
| DAAM1 | rs1268579 | rs2053298 | 1.00 | T | 0.253 | 0.02417 | 0.64 |
| DAAM1 | rs4127823 | rs12589351 | 0.61 | C | 0.338 | 0.02459 | 0.66 |
| DAAM1 | rs4901909 | rs8004164 | 0.60 | A | 0.513 | 0.01324 | 1.55 |
| DAAM1 | rs8022614 | rs8004164 | 0.74 | A | 0.513 | 0.01324 | 1.55 |
| DAAM1 | rs941884 | rs8004164 | 0.69 | A | 0.513 | 0.01324 | 1.55 |
| GPR135 | rs10136708 | rs1253170 | 0.67 | T | 0.319 | 0.01197 | 0.63 |
| GPR135 | rs10138199 | rs1253170 | 0.54 | T | 0.319 | 0.01197 | 0.63 |
| GPR135 | rs1253181 | rs1253170 | 0.74 | T | 0.319 | 0.01197 | 0.63 |
| GPR135 | rs4898989 | rs1253170 | 0.54 | T | 0.319 | 0.01197 | 0.63 |
| GPR135 | rs9323348 | rs1253170 | 0.54 | T | 0.319 | 0.01197 | 0.63 |
| EVL | rs1190956 | rs10136836 | 0.71 | T | 0.049 | 0.02337 | 0.43 |
| WDR25 | rs10873518 | rs8005782 | 1.00 | A | 0.468 | 0.007603 | 1.61 |
| HERC2 | rs1635168 | rs6497292 | 0.87 | G | 0.130 | 0.01823 | 1.91 |
| HERC2 | rs2238289 | rs6497292 | 0.51 | G | 0.130 | 0.01823 | 1.91 |
| HERC2 | rs7495174 | rs6497292 | 0.58 | G | 0.130 | 0.01823 | 1.91 |
| UNC13C | rs11856476 | rs8024165 | 0.84 | T | 0.352 | 0.01767 | 1.55 |
| UNC13C | rs12914912 | rs8024165 | 0.63 | T | 0.352 | 0.01767 | 1.55 |
| UNC13C | rs4776216 | rs8024165 | 0.52 | T | 0.352 | 0.01767 | 1.55 |
| ADAM10 | rs3764196 | rs7164844 | 0.51 | C | 0.074 | 0.00561 | 0.42 |
| ADAM10 | rs4775086 | rs605928 | 0.59 | G | 0.222 | 0.03434 | 0.65 |
| ADAM10 | rs514049 | rs605928 | 0.73 | G | 0.222 | 0.03434 | 0.65 |
| ADAM10 | rs653765 | rs605928 | 0.89 | G | 0.222 | 0.03434 | 0.65 |
| CDH11 | rs1520233 | rs1520233 | N/A | A | 0.309 | 0.03062 | 0.67 |
| CDH11 | rs35144 | rs40115 | 1.00 | T | 0.438 | 0.001518 | 1.77 |
| CDH11 | rs35148 | rs40115 | 0.68 | T | 0.438 | 0.001518 | 1.77 |
| CDH11 | rs35186 | rs40115 | 0.56 | T | 0.438 | 0.001518 | 1.77 |
| CDH11 | rs35195 | rs35195 | N/A | A | 0.438 | 0.002584 | 1.71 |
| CDH11 | rs35144 | rs35144 | N/A | C | 0.430 | 0.009028 | 1.60 |
| CDH11 | rs35186 | rs35186 | N/A | T | 0.544 | 0.04441 | 1.43 |
| BEAN | rs4247350 | rs1063438 | 0.59 | A | 0.265 | 0.01355 | 0.62 |
| KIAA0182 | rs3815794 | rs7195186 | 0.75 | G | 0.488 | 0.009922 | 1.57 |
| KIAA0182 | rs736845 | rs736845 | N/A | T | 0.231 | 0.01238 | 0.60 |
| C16orf74 | rs2305357 | rs394623 | 0.55 | C | 0.321 | 0.04089 | 0.69 |
| C16orf74 | rs373835 | rs394623 | 0.68 | C | 0.321 | 0.04089 | 0.69 |
| C16orf74 | rs386061 | rs394623 | 0.68 | C | 0.321 | 0.04089 | 0.69 |

Example 8

Novel Markers Associated with Overall Psychiatric Endophenotypes in SZ

Genotype and PANNS phonotype data were evaluated for 417 SZ patients enrolled in the CATIE trial. Following a period of drug wash-out, the CATIE study investigators rated each participant at baseline for psychopathology using the PANSS.

Each of the individual and composite scores is a quantitative trait that can be assessed using quantitative statistical genetics methods. Genetic analysis to determine the influence of haplotypes on quantitative PANSS values was performed using the PLINK 1.03 whole genome analysis toolset developed by Purcell and coworkers (Purcell et al., Am. J. Hum. Genet. 81:559-575 (2007)).

Confirmation of SNP Effects on Psychiatric Endophenotypes:

Tables 14 and 15 show numerous examples of novel alleles that affect the values obtained for specific psychiatric endophenotypes. Note in Tables 14 and 15 that haplotype blocks result in the same Test SNP being in linkage disequilibrium with multiple SNPs in Table B. Similarly, haplotype blocks result in multiple Test SNPs that can be used for each SNP listed in Table B, though such redundant examples are not presented in Tables 12 and 13 unless different test SNPs influence different psychiatric endophenotypes.

Tables 14 and 15 report results for specific SNP alleles that affect quantitative endophenotypes for SZ, along with Beta values and P values for the particular alleles of SNPs listed in Tables B and C. The Beta, beta weight from the regression, measures the impact of the SNP allele on the particular scale. A positive Beta means that the allele for the test SNP increases the score for that measure of psychopathology by the Beta value, while a negative Beta means that the allele for the test SNP decreases the score that for that measure of psychopathology by the Beta value.

Table 14 shows selected examples for PANSS Total score, Positive Symptoms subscale, Negative Symptoms subscale, and the General Psychopathology subscale, analyzed as quantitative traits in PLINK using linear regression.

Table 15 shows selected examples for the individual PANSS components. The component evaluated in each row is identified by one of the following abbreviations: Positive Symptoms: P1-delusions, P2-conceptual disorganization, P3-hallucinatory behavior, P4-exitement, P5-grandiosity, P6-suspiciousness, P7-hostility; Negative Symptoms: N1-blunted affect, N2-emotional withdrawal, N3-poor rapport, N4-passive/appathetic social withdrawal, N5-difficultiy in abstract thinking, N6-lack of spontaneity and flow of conversation, N7-steryotyped thinking; General Psychopathology Symptoms: G1-somatic concern, G2-anxiety, G3-guilt feelings, G4-tension, G5-mannerisms and posturing, G6-depression, G7-motor retardation, G8-uncooperativeness, G9-unusual thought content, G10-disorentation, G11-poor attention, G12-lack of judgment and insight, G13 disturbance of volition, G14-poor impulse control, G15-preoccupation, G16-active social avoidance.

TABLE 14

Alleles Influencing Composite Psychiatric Endophenotypes

| Gene Name | Table B SNP | Test SNP in linkage disequilibrium | $r^2$ | Allele | PANSS | Beta | P |
|---|---|---|---|---|---|---|---|
| CAMTA1 | rs12070592 | rs9434833 | 1.00 | T | Positive | −1.25 | 0.02983 |
| CAMTA1 | rs12070592 | rs2071918 | 1.00 | T | General | −1.83 | 0.0474 |
| CAMTA1 | rs1011124 | rs1616122 | 0.63 | C | General | −1.60 | 0.01229 |
| CAMTA1 | rs1417986 | rs2301488 | 0.54 | T | Negative | 1.05 | 0.02118 |
| PER3 | rs707463 | rs228688 | 0.75 | T | Negative | −1.02 | 0.0273 |
| PER3 | rs707465 | rs228688 | 0.81 | T | Negative | −1.02 | 0.0273 |
| RP1-21O18.1 | rs938249 | rs4661563 | 0.66 | G | Negative | −0.90 | 0.0453 |
| DNM3 | rs4382763 | rs12410416 | 1.00 | C | Positive | 0.97 | 0.04342 |
| DNM3 | rs4382763 | rs7550558 | 0.84 | G | Total | 3.38 | 0.01491 |
| DNM3 | rs4382763 | rs2586389 | 0.84 | A | Negative | 1.24 | 0.01611 |
| FASLG | rs10458360 | rs10458360 | N/A | C | General | −1.85 | 0.005609 |
| FASLG | rs12135884 | rs10458360 | 0.56 | C | General | −1.85 | 0.005609 |
| FASLG | rs10458360 | rs10458360 | N/A | C | Total | −2.67 | 0.03637 |
| FASLG | rs12135884 | rs10458360 | 0.56 | C | Total | −2.67 | 0.03637 |
| CACNA1E | rs17494681 | rs17494681 | N/A | T | Negative | −1.60 | 0.006522 |
| CACNA1E | rs199960 | rs1953690 | 0.81 | A | General | 1.39 | 0.04994 |
| CACNA1E | rs3856090 | rs7534913 | 0.50 | A | General | 1.31 | 0.04178 |
| CACNA1E | rs4652678 | rs17693196 | 0.50 | T | General | 2.21 | 0.01456 |
| CACNA1E | rs704326 | rs704331 | 0.64 | G | Negative | −1.27 | 0.005535 |
| CAMK1G | rs2356933 | rs6683256 | 1.00 | T | General | −1.45 | 0.03081 |
| CAMK1G | rs2356933 | rs6683256 | 1.00 | T | Total | −3.00 | 0.019 |
| CAMK1G | rs17014820 | rs10489339 | 0.70 | G | Total | 3.79 | 0.0419 |
| KCNH1 | rs1770213 | rs7546472 | 0.89 | C | General | 1.91 | 0.01334 |
| KCNH1 | rs1770213 | rs7546472 | 0.89 | C | Positive | 1.31 | 0.006236 |
| KCNH1 | rs1770213 | rs7546472 | 0.89 | C | Total | 3.93 | 0.007621 |
| KCNH1 | rs4620600 | rs4951495 | 0.79 | A | Negative | 1.37 | 0.01718 |
| KCNH1 | rs4620600 | rs11119679 | 0.83 | A | Positive | −1.16 | 0.0231 |
| EXOC2 | rs2493037 | rs2473484 | 1.00 | C | Positive | −1.24 | 0.03906 |
| ANK3 | rs10733757 | rs10761446 | 0.90 | C | Negative | −1.13 | 0.03077 |
| ANK3 | rs4568956 | rs10761446 | 0.57 | C | Negative | −1.13 | 0.03077 |
| ANK3 | rs7907721 | rs10761446 | 0.50 | C | Negative | −1.13 | 0.03077 |
| RHOG | rs1055640 | rs1055640 | N/A | G | Positive | −0.87 | 0.03465 |
| RHOG | rs11030008 | rs11030008 | N/A | G | General | 1.44 | 0.02802 |
| RHOG | rs1451722 | rs11030008 | 0.76 | G | General | 1.44 | 0.02802 |
| RHOG | rs11030008 | rs11030008 | N/A | G | Positive | 1.35 | 0.000922 |
| RHOG | rs1451722 | rs11030008 | 0.76 | G | Positive | 1.35 | 0.000922 |

TABLE 14-continued

Alleles Influencing Composite Psychiatric Endophenotypes

| Gene Name | Table B SNP | Test SNP in linkage disequilibrium | $r^2$ | Allele | PANSS | Beta | P |
|---|---|---|---|---|---|---|---|
| RHOG | rs11030008 | rs11030008 | N/A | G | Total | 3.22 | 0.01005 |
| RHOG | rs1451722 | rs11030008 | 0.76 | G | Total | 3.22 | 0.01005 |
| USH1C | rs1064074 | rs1064074 | N/A | C | Negative | 0.88 | 0.04895 |
| USH1C | rs2072225 | rs1064074 | 0.54 | C | Negative | 0.88 | 0.04895 |
| USH1C | rs16770 | rs2237961 | 0.92 | C | Positive | 1.61 | 0.014 |
| OTOG | rs10832824 | rs7111528 | 0.75 | T | Total | −2.73 | 0.04189 |
| OTOG | rs2023483 | rs7111528 | 0.70 | T | Total | −2.73 | 0.04189 |
| OTOG | rs2041028 | rs7111528 | 1.00 | T | Total | −2.73 | 0.04189 |
| OTOG | rs7111528 | rs7111528 | N/A | T | Total | −2.73 | 0.04189 |
| OTOG | rs1003490 | rs11024348 | 0.77 | T | General | −1.65 | 0.03189 |
| OTOG | rs10832824 | rs11024348 | 0.52 | T | General | −1.65 | 0.03189 |
| OTOG | rs2023483 | rs11024348 | 0.50 | T | General | −1.65 | 0.03189 |
| SERGEF | rs4757589 | rs11024415 | 0.63 | C | General | 1.28 | 0.04742 |
| PTPN5 | rs1550870 | rs7950091 | 0.84 | T | General | −1.57 | 0.01419 |
| PTPN5 | rs6483524 | rs7950091 | 0.50 | T | General | −1.57 | 0.01419 |
| PTPN5 | rs10766500 | rs11024782 | 0.93 | T | General | −1.82 | 0.009458 |
| PTPN5 | rs10766500 | rs11024782 | 0.93 | T | Negative | −0.98 | 0.04673 |
| PTPN5 | rs10766500 | rs11024782 | 0.93 | T | Total | −2.97 | 0.0268 |
| NAV2 | rs10833202 | rs11025328 | 0.61 | G | General | −1.66 | 0.01012 |
| NAV2 | rs6483629 | rs12099330 | 0.59 | T | Positive | −1.61 | 0.01255 |
| SLC6A5 | rs1443547 | rs16906507 | 0.54 | A | General | 1.51 | 0.0386 |
| SLC6A5 | rs894750 | rs16906507 | 0.77 | A | General | 1.51 | 0.0386 |
| SLC6A5 | rs1443547 | rs16906507 | 0.54 | A | Total | 2.97 | 0.03352 |
| SLC6A5 | rs894750 | rs16906507 | 0.77 | A | Total | 2.97 | 0.03352 |
| LRRC4C | rs10837367 | rs10501227 | 1.00 | G | Positive | −1.66 | 0.04454 |
| SYT13 | rs2863172 | rs4755941 | 0.80 | A | General | 2.40 | 0.02256 |
| SYT13 | rs2863174 | rs4755941 | 0.88 | A | General | 2.40 | 0.02256 |
| SYT13 | rs4755941 | rs4755941 | N/A | A | General | 2.40 | 0.02256 |
| SYT13 | rs7103871 | rs4755941 | 0.84 | A | General | 2.40 | 0.02256 |
| KIAA1853 | rs6490226 | rs1568922 | 0.91 | C | General | −1.83 | 0.01852 |
| KIAA1853 | rs6490226 | rs1568922 | 0.91 | C | Positive | −1.07 | 0.02697 |
| KIAA1853 | rs6490226 | rs1568922 | 0.91 | C | Total | −3.74 | 0.0115 |
| KIAA1853 | rs7136574 | rs4298970 | 0.72 | A | General | 1.46 | 0.03329 |
| KIAA1853 | rs7136574 | rs4075946 | 0.82 | T | Positive | −0.91 | 0.02171 |
| KIAA1853 | rs7136574 | rs4075946 | 0.82 | T | Total | −2.54 | 0.03892 |
| KIAA1853 | rs1541764 | rs1541764 | N/A | G | General | 1.52 | 0.01871 |
| KIAA1853 | rs2555269 | rs1541764 | 0.51 | G | General | 1.52 | 0.01871 |
| KIAA1853 | rs2723880 | rs1541764 | 0.74 | G | General | 1.52 | 0.01871 |
| KIAA1853 | rs2723882 | rs1541764 | 0.55 | G | General | 1.52 | 0.01871 |
| KIAA1853 | rs1541764 | rs1541764 | N/A | G | Negative | 1.18 | 0.009674 |
| KIAA1853 | rs2555269 | rs1541764 | 0.51 | G | Negative | 1.18 | 0.009674 |
| KIAA1853 | rs2723880 | rs1541764 | 0.74 | G | Negative | 1.18 | 0.009674 |
| KIAA1853 | rs2723882 | rs1541764 | 0.55 | G | Negative | 1.18 | 0.009674 |
| KIAA1853 | rs1541764 | rs1541764 | N/A | G | Total | 3.21 | 0.009581 |
| KIAA1853 | rs2555269 | rs1541764 | 0.51 | G | Total | 3.21 | 0.009581 |
| KIAA1853 | rs2723880 | rs1541764 | 0.74 | G | Total | 3.21 | 0.009581 |
| KIAA1853 | rs2723882 | rs1541764 | 0.55 | G | Total | 3.21 | 0.009581 |
| STX2 | rs1236 | rs7956851 | 0.81 | C | Negative | −0.99 | 0.04055 |
| STX2 | rs4759517 | rs7956851 | 1.00 | C | Negative | −0.99 | 0.04055 |
| STX2 | rs6486600 | rs7956851 | 0.97 | C | Negative | −0.99 | 0.04055 |
| STX2 | rs6486602 | rs7956851 | 1.00 | C | Negative | −0.99 | 0.04055 |
| TTC5 | rs2318864 | rs4981148 | 0.52 | T | General | −1.69 | 0.04301 |
| TTC5 | rs3737220 | rs4981148 | 0.51 | T | General | −1.69 | 0.04301 |
| TTC5 | rs3742945 | rs4981148 | 0.52 | T | General | −1.69 | 0.04301 |
| TTC5 | rs2318864 | rs4981148 | 0.52 | T | Total | −3.18 | 0.04708 |
| TTC5 | rs3737220 | rs4981148 | 0.51 | T | Total | −3.18 | 0.04708 |
| TTC5 | rs3742945 | rs4981148 | 0.52 | T | Total | −3.18 | 0.04708 |
| TEP1 | rs1713449 | rs1713448 | 0.96 | A | General | 1.55 | 0.0488 |
| TEP1 | rs7150689 | rs1713448 | 0.87 | A | General | 1.55 | 0.0488 |
| TEP1 | rs938886 | rs1713448 | 1.00 | A | General | 1.55 | 0.0488 |
| TEP1 | rs938887 | rs1713448 | 0.67 | A | General | 1.55 | 0.0488 |
| JPH4 | rs12897422 | rs12897422 | N/A | A | General | −2.40 | 0.0136 |
| JPH4 | rs12897422 | rs12897422 | N/A | A | Negative | −2.00 | 0.003322 |
| JPH4 | rs12897422 | rs12897422 | N/A | A | Total | −5.10 | 0.00594 |
| DAAM1 | rs10143918 | rs10483710 | 0.58 | A | Negative | −1.48 | 0.01586 |
| DAAM1 | rs12147707 | rs10483710 | 0.86 | A | Negative | −1.48 | 0.01586 |
| DAAM1 | rs17095965 | rs10483710 | 0.86 | A | Negative | −1.48 | 0.01586 |
| DAAM1 | rs1252989 | rs4901909 | 0.62 | T | Positive | 0.83 | 0.04088 |
| DAAM1 | rs1253005 | rs4901909 | 0.62 | T | Positive | 0.83 | 0.04088 |
| DAAM1 | rs4901909 | rs4901909 | N/A | T | Positive | 0.83 | 0.04088 |
| DAAM1 | rs8022614 | rs4901909 | 0.60 | T | Positive | 0.83 | 0.04088 |
| DAAM1 | rs941884 | rs4901909 | 0.85 | T | Positive | 0.83 | 0.04088 |
| DAAM1 | rs10143918 | rs6573250 | 0.69 | T | General | −1.52 | 0.01672 |
| DAAM1 | rs11626926 | rs1547199 | 0.85 | T | General | 1.37 | 0.03582 |

TABLE 14-continued

Alleles Influencing Composite Psychiatric Endophenotypes

| Gene Name | Table B SNP | Test SNP in linkage disequilibrium | r² | Allele | PANSS | Beta | P |
|---|---|---|---|---|---|---|---|
| DAAM1 | rs4127823 | rs1271513 | 0.65 | C | General | −1.57 | 0.02025 |
| DAAM1 | rs941886 | rs1271513 | 1.00 | C | General | −1.57 | 0.02025 |
| EML1 | rs2250718 | rs3783322 | 0.70 | G | General | 1.54 | 0.01544 |
| EML1 | rs2250718 | rs3783322 | 0.70 | G | Negative | 1.10 | 0.01418 |
| EML1 | rs2250718 | rs3783322 | 0.70 | G | Total | 2.62 | 0.03153 |
| EML1 | rs11160553 | rs11160554 | 1.00 | C | Negative | −1.83 | 0.000141 |
| EML1 | rs11160563 | rs11160554 | 0.56 | C | Negative | −1.83 | 0.000141 |
| EML1 | rs12433613 | rs11160554 | 0.88 | C | Negative | −1.83 | 0.000141 |
| EML1 | rs6575751 | rs11160554 | 1.00 | C | Negative | −1.83 | 0.000141 |
| EML1 | rs746698 | rs10131519 | 0.91 | C | Positive | 1.07 | 0.03808 |
| EML1 | rs746698 | rs10131519 | 0.91 | C | Total | 3.17 | 0.04577 |
| EML1 | rs2273707 | rs2250718 | 0.53 | T | General | 1.29 | 0.04771 |
| EML1 | rs2273704 | rs3818279 | 0.58 | G | Negative | 1.53 | 0.004398 |
| EML1 | rs746698 | rs3818279 | 0.71 | G | Negative | 1.53 | 0.004398 |
| EML1 | rs11160553 | rs4900447 | 0.59 | A | General | −2.06 | 0.002015 |
| EML1 | rs11160563 | rs4900447 | 0.97 | A | General | −2.06 | 0.002015 |
| EML1 | rs12433613 | rs4900447 | 0.51 | A | General | −2.06 | 0.002015 |
| EML1 | rs6575751 | rs4900447 | 0.59 | A | General | −2.06 | 0.002015 |
| EML1 | rs11160553 | rs4900447 | 0.59 | A | Total | −4.44 | 0.000493 |
| EML1 | rs11160563 | rs4900447 | 0.97 | A | Total | −4.44 | 0.000493 |
| EML1 | rs12433613 | rs4900447 | 0.51 | A | Total | −4.44 | 0.000493 |
| EML1 | rs6575751 | rs4900447 | 0.59 | A | Total | −4.44 | 0.000493 |
| HERC2 | rs11631797 | rs916977 | 0.86 | T | Negative | 1.26 | 0.01939 |
| HERC2 | rs2238289 | rs916977 | 0.79 | T | Negative | 1.26 | 0.01939 |
| HERC2 | rs916977 | rs916977 | N/A | T | Negative | 1.26 | 0.01939 |
| UNC13C | rs17731958 | rs17731958 | N/A | T | General | −3.74 | 0.01791 |
| UNC13C | rs2163195 | rs8024845 | 1.00 | G | Negative | 0.97 | 0.04595 |
| UNC13C | rs489526 | rs573320 | 0.70 | A | Negative | −1.04 | 0.04416 |
| UNC13C | rs489526 | rs500853 | 1.00 | G | Total | −2.76 | 0.03901 |
| UNC13C | rs16974691 | rs16974712 | 0.96 | T | General | −1.57 | 0.04754 |
| UNC13C | rs16974691 | rs16974712 | 0.96 | T | Negative | −1.39 | 0.01224 |
| UNC13C | rs16974691 | rs16974712 | 0.96 | T | Total | −3.83 | 0.01099 |
| Gcom1 | rs4774275 | rs9806498 | 1.00 | T | Positive | 0.98 | 0.01975 |
| GCOM1 | rs16977629 | rs16977629 | N/A | T | Negative | 2.21 | 0.01041 |
| Gcom1 | rs16977631 | rs16977629 | 0.56 | T | Negative | 2.21 | 0.01041 |
| GRINL1A | rs986868 | rs7176042 | 0.75 | A | Positive | −0.99 | 0.01843 |
| AKAP13 | rs745191 | rs745191 | N/A | T | Positive | 0.99 | 0.02393 |
| AKAP13 | rs11073502 | rs2291048 | 0.53 | A | Positive | 1.22 | 0.006071 |
| AKAP13 | rs2241268 | rs2241268 | N/A | A | Positive | 1.04 | 0.01761 |
| KLHL25 | rs11637212 | rs11637212 | N/A | G | Positive | 1.07 | 0.01597 |
| SV2B | rs11630131 | rs11631712 | 0.55 | C | Negative | −1.50 | 0.002999 |
| SV2B | rs2073967 | rs11631712 | 0.87 | C | Negative | −1.50 | 0.002999 |
| SLCO3A1 | rs2286355 | rs11630872 | 0.85 | T | Negative | −0.99 | 0.04033 |
| IGF1R | rs7170035 | rs4966012 | 0.55 | C | Negative | −1.04 | 0.03039 |
| IGF1R | rs4965436 | rs11634874 | 0.76 | C | Positive | 1.43 | 0.02266 |
| IGF1R | rs2684792 | rs7173377 | 0.96 | C | Positive | 1.22 | 0.0019 |
| CBLN1 | rs11076478 | rs1469906 | 0.72 | A | Negative | −1.15 | 0.01235 |
| CBLN1 | rs9935379 | rs1469906 | 0.90 | A | Negative | −1.15 | 0.01235 |
| ZNF423 | rs12924119 | rs4785185 | 0.50 | T | Positive | −1.04 | 0.03187 |
| CDH8 | rs4131634 | rs11862752 | 0.51 | A | General | −2.74 | 0.006021 |
| CDH8 | rs4131634 | rs11862752 | 0.51 | A | Total | −4.07 | 0.03321 |
| CDH8 | rs9939991 | rs13336134 | 0.55 | C | Positive | −0.99 | 0.01732 |
| CDH8 | rs11075445 | rs7189354 | 1.00 | G | Positive | −1.23 | 0.002488 |
| CDH8 | rs1369918 | rs7189354 | 1.00 | G | Positive | −1.23 | 0.002488 |
| CDH8 | rs1978796 | rs7189354 | 1.00 | G | Positive | −1.23 | 0.002488 |
| CDH8 | rs6498807 | rs7189354 | 0.80 | G | Positive | −1.23 | 0.002488 |
| CDH8 | rs1397131 | rs16964164 | 0.90 | T | Negative | 0.91 | 0.04219 |
| CDH8 | rs8057338 | rs16964164 | 0.93 | T | Negative | 0.91 | 0.04219 |
| CDH8 | rs9302540 | rs16964164 | 0.93 | T | Negative | 0.91 | 0.04219 |
| CDH11 | rs1520233 | rs4625747 | 0.67 | T | General | −1.51 | 0.02769 |
| CDH11 | rs35148 | rs35162 | 1.00 | A | General | 1.73 | 0.01682 |
| CDH11 | rs35144 | rs35162 | 0.68 | A | Positive | 1.14 | 0.01107 |
| CDH11 | rs35148 | rs35162 | 1.00 | A | Positive | 1.14 | 0.01107 |
| CDH11 | rs35144 | rs35162 | 0.68 | A | Total | 3.04 | 0.02738 |
| CDH11 | rs35148 | rs35162 | 1.00 | A | Total | 3.04 | 0.02738 |
| CDH11 | rs35186 | rs35140 | 0.56 | G | Positive | 0.91 | 0.0272 |
| CDH11 | rs35195 | rs35195 | N/A | A | General | 1.45 | 0.02761 |
| CDH11 | rs35195 | rs35195 | N/A | A | Positive | 0.87 | 0.03339 |
| CDH11 | rs35144 | rs35186 | 0.56 | T | General | 1.58 | 0.0137 |
| CDH11 | rs35186 | rs35186 | N/A | T | General | 1.58 | 0.0137 |
| CDH11 | rs35186 | rs35186 | N/A | T | Total | 2.57 | 0.03558 |
| KIAA0182 | rs1049868 | rs732460 | 0.58 | T | Negative | 1.11 | 0.03822 |
| KIAA0182 | rs3815795 | rs732460 | 0.59 | T | Negative | 1.11 | 0.03822 |
| PMP22 | rs13422 | rs192046 | 0.93 | T | General | 1.28 | 0.03702 |

TABLE 14-continued

Alleles Influencing Composite Psychiatric Endophenotypes

| Gene Name | Table B SNP | Test SNP in linkage disequilibrium | r² | Allele | PANSS | Beta | P |
|---|---|---|---|---|---|---|---|
| PMP22 | rs230938 | rs192046 | 0.67 | T | General | 1.28 | 0.03702 |
| PMP22 | rs179521 | rs11656487 | 0.83 | C | General | -1.41 | 0.02417 |
| PMP22 | rs231018 | rs11656487 | 0.52 | C | General | -1.41 | 0.02417 |
| PMP22 | rs179521 | rs11656487 | 0.83 | C | Total | -2.48 | 0.03766 |
| PMP22 | rs231018 | rs11656487 | 0.52 | C | Total | -2.48 | 0.03766 |
| KATNAL2 | rs2187092 | rs2010834 | 0.97 | A | General | 2.27 | 0.0008 |
| KATNAL2 | rs2247221 | rs2010834 | 0.56 | A | General | 2.27 | 0.0008 |
| KATNAL2 | rs2571030 | rs2010834 | 0.56 | A | General | 2.27 | 0.0008 |
| KATNAL2 | rs2576042 | rs2010834 | 0.59 | A | General | 2.27 | 0.0008 |
| KATNAL2 | rs7233515 | rs2010834 | 0.69 | A | General | 2.27 | 0.0008 |
| KATNAL2 | rs9304340 | rs2010834 | 0.97 | A | General | 2.27 | 0.0008 |
| KATNAL2 | rs2187092 | rs2010834 | 0.97 | A | Negative | 1.18 | 0.01344 |
| KATNAL2 | rs2247221 | rs2010834 | 0.56 | A | Negative | 1.18 | 0.01344 |
| KATNAL2 | rs2571030 | rs2010834 | 0.56 | A | Negative | 1.18 | 0.01344 |
| KATNAL2 | rs2576042 | rs2010834 | 0.59 | A | Negative | 1.18 | 0.01344 |
| KATNAL2 | rs7233515 | rs2010834 | 0.69 | A | Negative | 1.18 | 0.01344 |
| KATNAL2 | rs9304340 | rs2010834 | 0.97 | A | Negative | 1.18 | 0.01344 |
| KATNAL2 | rs2187092 | rs2010834 | 0.97 | A | Total | 4.45 | 0.000588 |
| KATNAL2 | rs2247221 | rs2010834 | 0.56 | A | Total | 4.45 | 0.000588 |
| KATNAL2 | rs2571030 | rs2010834 | 0.56 | A | Total | 4.45 | 0.000588 |
| KATNAL2 | rs2576042 | rs2010834 | 0.59 | A | Total | 4.45 | 0.000588 |
| KATNAL2 | rs7233515 | rs2010834 | 0.69 | A | Total | 4.45 | 0.000588 |
| KATNAL2 | rs9304340 | rs2010834 | 0.97 | A | Total | 4.45 | 0.000588 |
| KATNAL2 | rs9961383 | rs2571034 | 0.60 | G | General | 1.61 | 0.01919 |
| KATNAL2 | rs9961383 | rs2571034 | 0.60 | G | Total | 2.68 | 0.04215 |
| KATNAL2 | rs2187092 | rs2576040 | 0.57 | T | Positive | -1.02 | 0.01334 |
| KATNAL2 | rs2247221 | rs2576040 | 0.61 | T | Positive | -1.02 | 0.01334 |
| KATNAL2 | rs2571030 | rs2576040 | 0.61 | T | Positive | -1.02 | 0.01334 |
| KATNAL2 | rs2576042 | rs2576040 | 1.00 | T | Positive | -1.02 | 0.01334 |
| KATNAL2 | rs7233515 | rs2576040 | 0.51 | T | Positive | -1.02 | 0.01334 |
| KATNAL2 | rs9304340 | rs2576040 | 0.57 | T | Positive | -1.02 | 0.01334 |
| FUSSEL18 | rs10502880 | rs9304344 | 0.85 | T | General | -1.48 | 0.02048 |
| FUSSEL18 | rs17785419 | rs9304344 | 0.85 | T | General | -1.48 | 0.02048 |
| FUSSEL18 | rs2668771 | rs9304344 | 0.64 | T | General | -1.48 | 0.02048 |
| FUSSEL18 | rs7236105 | rs9304344 | 1.00 | T | General | -1.48 | 0.02048 |
| FUSSEL18 | rs10502880 | rs9304344 | 0.85 | T | Positive | -0.87 | 0.02914 |
| FUSSEL18 | rs17785419 | rs9304344 | 0.85 | T | Positive | -0.87 | 0.02914 |
| FUSSEL18 | rs2668771 | rs9304344 | 0.64 | T | Positive | -0.87 | 0.02914 |
| FUSSEL18 | rs7236105 | rs9304344 | 1.00 | T | Positive | -0.87 | 0.02914 |
| FUSSEL18 | rs10502880 | rs9304344 | 0.85 | T | Total | -2.69 | 0.02795 |
| FUSSEL18 | rs17785419 | rs9304344 | 0.85 | T | Total | -2.69 | 0.02795 |
| FUSSEL18 | rs2668771 | rs9304344 | 0.64 | T | Total | -2.69 | 0.02795 |
| FUSSEL18 | rs7236105 | rs9304344 | 1.00 | T | Total | -2.69 | 0.02795 |
| DCC | rs6508145 | rs1031062 | 0.67 | G | Negative | -1.36 | 0.02919 |
| DCC | rs6508145 | rs1031062 | 0.67 | G | Total | -3.34 | 0.04901 |
| DCC | rs1893572 | rs7228674 | 0.77 | T | Negative | 1.68 | 0.000333 |
| DCC | rs1893572 | rs9807201 | 0.65 | A | General | 1.73 | 0.01191 |
| DCC | rs1893572 | rs9807201 | 0.65 | A | Total | 3.16 | 0.01642 |
| DCC | rs1431748 | rs4998815 | 0.61 | G | General | -1.47 | 0.02576 |
| DCC | rs1431748 | rs9953016 | 0.81 | C | Negative | -1.13 | 0.0172 |
| DCC | rs1431748 | rs7504750 | 0.63 | C | Total | -2.97 | 0.02854 |
| TMEPAI | rs427278 | rs203386 | 0.51 | C | General | 1.51 | 0.02214 |
| TMEPAI | rs427278 | rs203386 | 0.51 | C | Total | 2.78 | 0.02738 |

TABLE 15

Alleles Influencing Specific Psychiatric Endophenotypes

| Gene Name | Table B SNP | Test SNP in linkage disequilibrium | r² | Allele | PANSS | Beta | P |
|---|---|---|---|---|---|---|---|
| CAMTA1 | rs7554752 | rs4908575 | 0.96 | C | G10 | 0.18 | 0.002944 |
| CAMTA1 | rs12070592 | rs2071918 | 1.00 | T | G6 | -0.42 | 0.002692 |
| CAMTA1 | rs12070592 | rs2071918 | 1.00 | T | G9 | -0.38 | 0.003607 |
| CAMTA1 | rs707455 | rs697686 | 0.66 | T | N7 | -0.27 | 0.002057 |
| PER3 | rs707463 | rs707463 | N/A | T | N7 | -0.25 | 0.004339 |
| PER3 | rs707465 | rs697686 | 0.93 | T | N7 | -0.27 | 0.002057 |
| PER3 | rs707463 | rs697686 | 1.00 | T | N7 | -0.27 | 0.002057 |
| PER3 | rs2640909 | rs228652 | 0.70 | A | N5 | -0.34 | 0.002229 |
| RP1-21O18.1 | rs12057431 | rs10803343 | 1.00 | C | G14 | 0.95 | 0.0002941 |

TABLE 15-continued

Alleles Influencing Specific Psychiatric Endophenotypes

| Gene Name | Table B SNP | Test SNP in linkage disequilibrium | $r^2$ | Allele | PANSS | Beta | P |
|---|---|---|---|---|---|---|---|
| RP1-21O18.1 | rs4661572 | rs1000313 | 0.63 | G | G14 | 0.28 | 0.0003008 |
| KCND3 | rs3738298 | rs584096 | 0.70 | G | G10 | −0.28 | 0.0003434 |
| DNM3 | rs4382763 | rs2586392 | 0.84 | C | N7 | 0.27 | 0.003464 |
| CACNA1E | rs17494681 | rs17494681 | N/A | T | N4 | −0.37 | 0.003546 |
| CACNA1E | rs3856090 | rs10797729 | 0.70 | A | G7 | 0.34 | 0.0001445 |
| CACNA1E | rs199960 | rs10797729 | 0.77 | A | G7 | 0.34 | 0.0001445 |
| CACNA1E | rs199960 | rs7513540 | 0.61 | T | G1 | −0.32 | 0.001712 |
| CACNA1E | rs4652678 | rs17693196 | 0.50 | T | G1 | 0.40 | 0.002089 |
| CACNA1E | rs704326 | rs704331 | 0.64 | G | G7 | −0.28 | 0.0005166 |
| CACNA1E | rs704326 | rs704331 | 0.64 | G | N1 | −0.32 | 0.00162 |
| CACNA1E | rs704326 | rs704331 | 0.64 | G | N3 | −0.28 | 0.001365 |
| CACNA1E | rs704326 | rs704331 | 0.64 | G | N6 | −0.32 | 0.0008968 |
| CAMK1G | rs17014820 | rs7512091 | 0.91 | A | G5 | 0.29 | 0.001812 |
| CAMK1G | rs6690557 | rs713075 | 0.80 | A | G5 | −0.23 | 0.003493 |
| CAMK1G | rs17014820 | rs7516885 | 1.00 | T | N7 | 0.38 | 0.0007187 |
| CAMK1G | rs17014820 | rs10489339 | 0.70 | G | G4 | 0.43 | 0.0006328 |
| KCNH1 | rs1770213 | rs7546472 | 0.89 | C | P1 | 0.39 | 0.003181 |
| DPH3 | rs2245721 | rs842264 | 0.57 | T | P5 | 0.30 | 0.0005309 |
| DPH3 | rs842257 | rs842264 | 0.57 | T | P5 | 0.30 | 0.0005309 |
| DPH3 | rs859703 | rs842264 | 0.57 | T | P5 | 0.30 | 0.0005309 |
| DPH3 | rs2245708 | rs842261 | 0.67 | A | P5 | 0.27 | 0.004185 |
| DPH3 | rs2245721 | rs842251 | 1.00 | G | G10 | 0.20 | 0.000734 |
| DPH3 | rs842257 | rs842251 | 1.00 | G | G10 | 0.20 | 0.000734 |
| DPH3 | rs859703 | rs842251 | 1.00 | G | G10 | 0.20 | 0.000734 |
| DPH3 | rs2245721 | rs842259 | 1.00 | T | G7 | −0.23 | 0.004115 |
| DPH3 | rs842257 | rs842259 | 1.00 | T | G7 | −0.23 | 0.004115 |
| DPH3 | rs859703 | rs842259 | 1.00 | T | G7 | −0.23 | 0.004115 |
| EXOC2 | rs1473909 | rs9405242 | 0.97 | A | N5 | −0.35 | 0.0008412 |
| TOLLIP | rs3168046 | rs2014486 | 0.85 | A | G7 | −0.24 | 0.001849 |
| TOLLIP | rs3750920 | rs2014486 | 0.85 | A | G7 | −0.24 | 0.001849 |
| BRSK2 | rs1554857 | rs1554857 | N/A | A | G5 | −0.23 | 0.002684 |
| BRSK2 | rs1554857 | rs1108991 | 0.81 | G | G5 | −0.25 | 0.001173 |
| HCCA2 | rs7945160 | rs1108991 | 0.55 | G | G5 | −0.25 | 0.001173 |
| HCCA2 | rs9440 | rs1108991 | 0.55 | G | G5 | −0.25 | 0.001173 |
| HCCA2 | rs7396514 | rs1108991 | 1.00 | G | G5 | −0.25 | 0.001173 |
| DUSP8 | rs10734456 | rs1108991 | 0.55 | G | G5 | −0.25 | 0.001173 |
| DUSP8 | rs902224 | rs1108991 | 0.81 | G | G5 | −0.25 | 0.001173 |
| RHOG | rs1055640 | rs1055640 | N/A | G | G4 | −0.25 | 0.003073 |
| RHOG | rs1451722 | rs11030008 | 0.76 | G | P1 | 0.32 | 0.00439 |
| RHOG | rs11030008 | rs11030008 | N/A | G | P1 | 0.32 | 0.00439 |
| RHOG | rs1451722 | rs11030008 | 0.76 | G | P6 | 0.33 | 0.001515 |
| RHOG | rs11030008 | rs11030008 | N/A | G | P6 | 0.33 | 0.001515 |
| USH1C | rs2072225 | rs1064074 | 0.54 | C | G16 | 0.28 | 0.002619 |
| USH1C | rs1064074 | rs1064074 | N/A | C | G16 | 0.28 | 0.002619 |
| USH1C | rs16770 | rs2237961 | 0.92 | C | P4 | 0.42 | 0.0007385 |
| OTOG | rs2041028 | rs757982 | 0.64 | A | G12 | −0.32 | 0.0007194 |
| OTOG | rs7111528 | rs757982 | 0.64 | A | G12 | −0.32 | 0.0007194 |
| OTOG | rs2023483 | rs7111528 | 0.70 | T | P2 | −0.27 | 0.008232 |
| OTOG | rs10832824 | rs7111528 | 0.75 | T | P2 | −0.27 | 0.008232 |
| OTOG | rs2041028 | rs7111528 | 1.00 | T | P2 | −0.27 | 0.008232 |
| OTOG | rs7111528 | rs7111528 | N/A | T | P2 | −0.27 | 0.008232 |
| OTOG | rs2023483 | rs4757560 | 0.52 | T | P5 | −0.25 | 0.008921 |
| PTPN5 | rs10766500 | rs11024782 | 0.93 | T | G16 | −0.31 | 0.002084 |
| PTPN5 | rs10766500 | rs755796 | 0.93 | G | G10 | −0.19 | 0.004029 |
| NAV2 | rs10833202 | rs11025328 | 0.61 | G | G15 | −0.25 | 0.003892 |
| NAV2 | rs7125647 | rs10833228 | 0.65 | C | G11 | 0.30 | 0.0007124 |
| LRRC4C | rs2953310 | rs2953310 | N/A | C | P4 | −0.21 | 0.004729 |
| LRRC4C | rs10837367 | rs10501227 | 1.00 | G | P1 | −0.67 | 0.003309 |
| HSD17B12 | rs1061810 | rs10838186 | 0.87 | C | G5 | 0.21 | 0.003535 |
| HSD17B12 | rs4755744 | rs10838186 | 1.00 | C | G5 | 0.21 | 0.003535 |
| HSD17B12 | rs11037691 | rs11037691 | N/A | A | G5 | 0.39 | 0.004419 |
| SYT13 | rs12362429 | rs12362444 | 1.00 | G | G10 | 0.21 | 0.0007107 |
| SYT13 | rs12362429 | rs12362444 | 1.00 | G | P2 | 0.29 | 0.002839 |
| SYT13 | rs4992029 | rs1075778 | 0.61 | G | P2 | 0.27 | 0.009285 |
| SYT13 | rs2863182 | rs1075778 | 0.84 | G | P2 | 0.27 | 0.009285 |
| SYT13 | rs11038382 | rs1075778 | 1.00 | G | P2 | 0.27 | 0.009285 |
| SYT13 | rs4992029 | rs6485608 | 0.50 | C | G10 | 0.20 | 0.002462 |
| SYT13 | rs11038382 | rs6485608 | 0.84 | C | G10 | 0.20 | 0.002462 |
| SYT13 | rs2863182 | rs6485608 | 1.00 | C | G10 | 0.20 | 0.002462 |
| DTX4 | rs1048444 | rs2211912 | 0.77 | A | N6 | 0.32 | 0.0006063 |
| DTX4 | rs3847 | rs2211912 | 0.77 | A | N6 | 0.32 | 0.0006063 |
| DTX4 | rs656163 | rs2211912 | 0.88 | A | N6 | 0.32 | 0.0006063 |
| DTX4 | rs5029315 | rs2211912 | 1.00 | A | N6 | 0.32 | 0.0006063 |
| DTX4 | rs2211912 | rs2211912 | N/A | A | N6 | 0.32 | 0.0006063 |

TABLE 15-continued

Alleles Influencing Specific Psychiatric Endophenotypes

| Gene Name | Table B SNP | Test SNP in linkage disequilibrium | r² | Allele | PANSS | Beta | P |
|---|---|---|---|---|---|---|---|
| DTX4 | rs3847 | rs3847 | N/A | A | N6 | 0.30 | 0.003075 |
| DTX4 | rs621162 | rs544864 | 1.00 | T | N6 | 0.35 | 0.0008417 |
| DTX4 | rs544864 | rs544864 | N/A | T | N6 | 0.35 | 0.0008417 |
| KIAA1853 | rs6490226 | rs7966721 | 0.53 | G | N1 | −0.32 | 0.00181 |
| KIAA1853 | rs7136574 | rs4298970 | 0.72 | A | G1 | 0.28 | 0.004999 |
| RIMBP2 | rs4237817 | rs1877978 | 0.55 | C | G4 | 0.25 | 0.003266 |
| TTC5 | rs3737220 | rs4981148 | 0.51 | T | G15 | −0.32 | 0.004087 |
| TTC5 | rs2318864 | rs4981148 | 0.52 | T | G15 | −0.32 | 0.004087 |
| TTC5 | rs3742945 | rs4981148 | 0.52 | T | G15 | −0.32 | 0.004087 |
| NDRG2 | rs1243444 | rs1243446 | 0.58 | G | G15 | 0.23 | 0.004573 |
| NDRG2 | rs1243446 | rs1243446 | N/A | G | G15 | 0.23 | 0.004573 |
| JPH4 | rs12897422 | rs12897422 | N/A | A | G2 | −0.45 | 0.0009928 |
| JPH4 | rs12897422 | rs12897422 | N/A | A | G6 | −0.44 | 0.002891 |
| JPH4 | rs12897422 | rs12897422 | N/A | A | N4 | −0.43 | 0.003217 |
| DACT1 | rs464582 | rs464582 | N/A | C | G14 | −0.19 | 0.0041 |
| DACT1 | rs464582 | rs464582 | N/A | C | P4 | −0.22 | 0.004041 |
| DACT1 | rs464582 | rs464582 | N/A | C | P7 | −0.21 | 0.001554 |
| DAAM1 | rs12147707 | rs10483710 | 0.86 | A | G13 | −0.36 | 0.0009634 |
| DAAM1 | rs17095965 | rs10483710 | 0.86 | A | G13 | −0.36 | 0.0009634 |
| DAAM1 | rs10143918 | rs10483710 | 0.58 | A | G5 | −0.28 | 0.003772 |
| DAAM1 | rs12147707 | rs10483710 | 0.86 | A | G5 | −0.28 | 0.003772 |
| DAAM1 | rs17095965 | rs10483710 | 0.86 | A | G5 | −0.28 | 0.003772 |
| DAAM1 | rs10143918 | rs6573250 | 0.69 | T | G13 | −0.28 | 0.0003461 |
| DAAM1 | rs941886 | rs941886 | N/A | C | G13 | −0.24 | 0.003883 |
| DAAM1 | rs11626926 | rs1547199 | 0.85 | T | G13 | 0.23 | 0.004418 |
| DAAM1 | rs4127823 | rs1271513 | 0.65 | C | G13 | −0.25 | 0.003443 |
| DAAM1 | rs941886 | rs1271513 | 1.00 | C | G13 | −0.25 | 0.003443 |
| GPR135 | rs17255731 | rs4898989 | 0.51 | A | P6 | −0.29 | 0.005506 |
| GPR135 | rs10136708 | rs4898989 | 0.61 | A | P6 | −0.29 | 0.005506 |
| GPR135 | rs1253181 | rs4898989 | 0.81 | A | P6 | −0.29 | 0.005506 |
| GPR135 | rs10138199 | rs4898989 | 1.00 | A | P6 | −0.29 | 0.005506 |
| GPR135 | rs9323348 | rs4898989 | 1.00 | A | P6 | −0.29 | 0.005506 |
| GPR135 | rs4898989 | rs4898989 | N/A | A | P6 | −0.29 | 0.005506 |
| GPR135 | rs10136708 | rs1253103 | 0.54 | C | G16 | −0.27 | 0.003698 |
| GPR135 | rs17255731 | rs1253103 | 0.57 | C | G16 | −0.27 | 0.003698 |
| GPR135 | rs1253181 | rs1253103 | 0.71 | C | G16 | −0.27 | 0.003698 |
| GPR135 | rs10138199 | rs1253103 | 0.88 | C | G16 | −0.27 | 0.003698 |
| GPR135 | rs4898989 | rs1253103 | 0.88 | C | G16 | −0.27 | 0.003698 |
| GPR135 | rs9323348 | rs1253103 | 0.88 | C | G16 | −0.27 | 0.003698 |
| RTN1 | rs10145080 | rs12878097 | 0.55 | C | G12 | 0.32 | 0.003522 |
| RTN1 | rs17310036 | rs12878097 | 1.00 | C | G12 | 0.32 | 0.003522 |
| RTN1 | rs17310036 | rs1951366 | 0.79 | A | N3 | 0.26 | 0.002511 |
| RTN1 | rs10145080 | rs17256003 | 0.55 | C | G8 | 0.20 | 0.0032 |
| RTN1 | rs17310036 | rs17256003 | 1.00 | C | G8 | 0.20 | 0.0032 |
| EML1 | rs2250718 | rs3783322 | 0.70 | G | G7 | 0.29 | 0.0002896 |
| EML1 | rs11160563 | rs11160554 | 0.56 | C | N1 | −0.35 | 0.001551 |
| EML1 | rs11160563 | rs11160554 | 0.56 | C | N6 | −0.30 | 0.003367 |
| EML1 | rs12433613 | rs11160554 | 0.88 | C | N6 | −0.30 | 0.003367 |
| EML1 | rs11160553 | rs11160554 | 1.00 | C | N6 | −0.30 | 0.003367 |
| EML1 | rs6575751 | rs11160554 | 1.00 | C | N6 | −0.30 | 0.003367 |
| EML1 | rs11160563 | rs1957509 | 0.56 | A | G7 | −0.29 | 0.0006263 |
| EML1 | rs12433613 | rs1957509 | 0.88 | A | G7 | −0.29 | 0.0006263 |
| EML1 | rs11160553 | rs1957509 | 1.00 | A | G7 | −0.29 | 0.0006263 |
| EML1 | rs6575751 | rs1957509 | 1.00 | A | G7 | −0.29 | 0.0006263 |
| EML1 | rs11160553 | rs1191109 | 0.51 | A | N1 | −0.37 | 0.0002563 |
| EML1 | rs6575751 | rs1191109 | 0.51 | A | N1 | −0.37 | 0.0002563 |
| EML1 | rs11160553 | rs1191109 | 0.51 | A | N3 | −0.28 | 0.001132 |
| EML1 | rs6575751 | rs1191109 | 0.51 | A | N3 | −0.28 | 0.001132 |
| EML1 | rs12433613 | rs1005766 | 0.77 | G | N1 | −0.35 | 0.001409 |
| EML1 | rs12433613 | rs1005766 | 0.77 | G | N4 | −0.30 | 0.003513 |
| EML1 | rs11160553 | rs1005766 | 0.88 | G | N4 | −0.30 | 0.003513 |
| EML1 | rs6575751 | rs1005766 | 0.88 | G | N4 | −0.30 | 0.003513 |
| EML1 | rs2273707 | rs975252 | 0.59 | T | G7 | 0.26 | 0.001636 |
| EML1 | rs2273707 | rs2250718 | 0.53 | T | G2 | 0.31 | 0.0005703 |
| EML1 | rs2250718 | rs2250718 | N/A | T | G2 | 0.31 | 0.0005703 |
| EML1 | rs2273704 | rs3818279 | 0.58 | G | N1 | 0.41 | 0.0006622 |
| EML1 | rs746698 | rs3818279 | 0.71 | G | N1 | 0.41 | 0.0006622 |
| EML1 | rs11160563 | rs8020741 | 0.68 | T | G5 | −0.22 | 0.00144 |
| EML1 | rs12433613 | rs4900447 | 0.51 | A | G15 | −0.31 | 0.0004618 |
| EML1 | rs11160553 | rs4900447 | 0.59 | A | G15 | −0.31 | 0.0004618 |
| EML1 | rs6575751 | rs4900447 | 0.59 | A | G15 | −0.31 | 0.0004618 |
| EML1 | rs11160563 | rs4900447 | 0.97 | A | G15 | −0.31 | 0.0004618 |
| EML1 | rs12433613 | rs4900447 | 0.51 | A | G5 | −0.22 | 0.002755 |
| EML1 | rs11160553 | rs4900447 | 0.59 | A | G5 | −0.22 | 0.002755 |

TABLE 15-continued

Alleles Influencing Specific Psychiatric Endophenotypes

| Gene Name | Table B SNP | Test SNP in linkage disequilibrium | $r^2$ | Allele | PANSS | Beta | P |
|---|---|---|---|---|---|---|---|
| EML1 | rs6575751 | rs4900447 | 0.59 | A | G5 | −0.22 | 0.002755 |
| EML1 | rs12433613 | rs4900447 | 0.51 | A | N7 | −0.25 | 0.003313 |
| EML1 | rs11160553 | rs4900447 | 0.59 | A | N7 | −0.25 | 0.003313 |
| EML1 | rs6575751 | rs4900447 | 0.59 | A | N7 | −0.25 | 0.003313 |
| EML1 | rs11160563 | rs4900447 | 0.97 | A | N7 | −0.25 | 0.003313 |
| EVL | rs1190956 | rs2400848 | 0.51 | C | G16 | −0.54 | 0.004824 |
| BEGAIN | rs7140556 | rs1190862 | 0.65 | T | G14 | −0.23 | 0.001153 |
| HERC2 | rs2238289 | rs916977 | 0.79 | T | N3 | 0.37 | 0.0003766 |
| HERC2 | rs11631797 | rs916977 | 0.86 | T | N3 | 0.37 | 0.0003766 |
| HERC2 | rs916977 | rs916977 | N/A | T | N3 | 0.37 | 0.0003766 |
| HERC2 | rs2238289 | rs916977 | 0.79 | T | N6 | 0.37 | 0.001355 |
| HERC2 | rs11631797 | rs916977 | 0.86 | T | N6 | 0.37 | 0.001355 |
| HERC2 | rs916977 | rs916977 | N/A | T | N6 | 0.37 | 0.001355 |
| UNC13C | rs17731958 | rs17731958 | N/A | T | G6 | −0.95 | 0.00007556 |
| UNC13C | rs489526 | rs500853 | 1.00 | G | N7 | −0.25 | 0.004691 |
| UNC13C | rs489526 | rs500853 | 1.00 | G | P2 | −0.29 | 0.004176 |
| UNC13C | rs16974691 | rs16974712 | 0.96 | T | G10 | −0.21 | 0.0047 |
| UNC13C | rs16974691 | rs16974712 | 0.96 | T | P2 | −0.34 | 0.003461 |
| Gcom1 | rs16977631 | rs16977629 | 0.56 | T | G16 | 0.52 | 0.003424 |
| Gcom1 | rs16977629 | rs16977629 | N/A | T | G16 | 0.52 | 0.003424 |
| GRINL1A | rs986868 | rs1425948 | 0.97 | A | P7 | −0.21 | 0.001524 |
| AKAP13 | rs745191 | rs745191 | N/A | T | G9 | 0.29 | 0.003429 |
| AKAP13 | rs11073502 | rs2291048 | 0.53 | A | G9 | 0.30 | 0.002606 |
| AKAP13 | rs11073502 | rs2291048 | 0.53 | A | P1 | 0.37 | 0.002475 |
| AKAP13 | rs2241268 | rs2241268 | N/A | A | G9 | 0.28 | 0.004651 |
| KLHL25 | rs11637212 | rs11637212 | N/A | G | P5 | 0.26 | 0.009632 |
| SV2B | rs11630131 | rs11631712 | 0.55 | C | N4 | −0.31 | 0.003964 |
| SV2B | rs2073967 | rs11631712 | 0.87 | C | N4 | −0.31 | 0.003964 |
| SLCO3A1 | rs4294800 | rs8032981 | 0.67 | A | G1 | −0.35 | 0.001287 |
| SLCO3A1 | rs4294800 | rs975721 | 0.51 | G | P5 | −0.26 | 0.004699 |
| SLCO3A1 | rs2176452 | rs975721 | 0.53 | G | P5 | −0.26 | 0.004699 |
| IGF1R | rs4965436 | rs11634874 | 0.76 | C | P5 | 0.40 | 0.005139 |
| IGF1R | rs11247380 | rs1879613 | 0.53 | A | G1 | 0.39 | 0.0005785 |
| IGF1R | rs1879613 | rs1879613 | N/A | A | G1 | 0.39 | 0.0005785 |
| IGF1R | rs2684792 | rs7173377 | 0.96 | C | G9 | 0.26 | 0.004224 |
| IGF1R | rs2684792 | rs7173377 | 0.96 | C | P3 | 0.33 | 0.003003 |
| IGF1R | rs2684792 | rs7173377 | 0.96 | C | P5 | 0.27 | 0.002108 |
| NDRG4 | rs42945 | rs40359 | 0.66 | C | G12 | −0.28 | 0.002966 |
| GOT2 | rs2042445 | rs7204324 | 0.51 | T | P5 | −0.41 | 0.008799 |
| CDH8 | rs4636897 | rs11641508 | 1.00 | A | G2 | 0.44 | 0.0009623 |
| CDH8 | rs4131634 | rs4416006 | 0.96 | C | G5 | −0.25 | 0.002379 |
| CDH8 | rs4131634 | rs11862752 | 0.51 | A | G4 | −0.39 | 0.002652 |
| CDH8 | rs6498807 | rs7189354 | 0.80 | G | P1 | −0.32 | 0.004743 |
| CDH8 | rs11075445 | rs7189354 | 1.00 | G | P1 | −0.32 | 0.004743 |
| CDH8 | rs1369918 | rs7189354 | 1.00 | G | P1 | −0.32 | 0.004743 |
| CDH8 | rs1978796 | rs7189354 | 1.00 | G | P1 | −0.32 | 0.004743 |
| CDH11 | rs35144 | rs35165 | 0.68 | A | G6 | 0.35 | 0.001477 |
| CDH11 | rs35148 | rs35165 | 1.00 | A | G6 | 0.35 | 0.001477 |
| CDH11 | rs35144 | rs35162 | 0.68 | A | G2 | 0.29 | 0.00496 |
| CDH11 | rs35148 | rs35162 | 1.00 | A | G2 | 0.29 | 0.00496 |
| KIAA0513 | rs4783121 | rs16975240 | 0.87 | G | G6 | −0.70 | 0.002637 |
| PMP22 | rs13422 | rs231020 | 0.64 | T | P3 | −0.36 | 0.0008073 |
| PMP22 | rs231021 | rs231020 | 0.67 | T | P3 | −0.36 | 0.0008073 |
| PMP22 | rs231018 | rs231020 | 0.93 | T | P3 | −0.36 | 0.0008073 |
| PMP22 | rs231018 | rs10852830 | 0.52 | C | G13 | −0.24 | 0.001942 |
| PMP22 | rs179521 | rs10852830 | 0.83 | C | G13 | −0.24 | 0.001942 |
| KATNAL2 | rs2247221 | rs2010834 | 0.56 | A | N7 | 0.33 | 0.0001519 |
| KATNAL2 | rs2571030 | rs2010834 | 0.56 | A | N7 | 0.33 | 0.0001519 |
| KATNAL2 | rs2576042 | rs2010834 | 0.59 | A | N7 | 0.33 | 0.0001519 |
| KATNAL2 | rs7233515 | rs2010834 | 0.69 | A | N7 | 0.33 | 0.0001519 |
| KATNAL2 | rs2187092 | rs2010834 | 0.97 | A | N7 | 0.33 | 0.0001519 |
| KATNAL2 | rs9304340 | rs2010834 | 0.97 | A | N7 | 0.33 | 0.0001519 |
| KIAA0427 | rs2175565 | rs9952398 | 1.00 | C | G1 | −0.31 | 0.00361 |
| KIAA0427 | rs937021 | rs937021 | N/A | G | N5 | 0.30 | 0.003682 |
| DYM | rs357894 | rs357894 | N/A | G | G9 | −0.33 | 0.0006157 |
| DYM | rs498929 | rs16950465 | 0.54 | T | G9 | −0.36 | 0.001734 |
| DCC | rs17753970 | rs16954731 | 0.87 | G | G4 | 0.27 | 0.004839 |
| DCC | rs8089980 | rs8089980 | N/A | T | G16 | 0.27 | 0.003432 |
| DCC | rs8089980 | rs8089980 | N/A | T | G7 | 0.24 | 0.002252 |
| DCC | rs8089980 | rs10853621 | 0.76 | T | G7 | 0.25 | 0.001494 |
| DCC | rs8089980 | rs10853622 | 0.76 | A | G12 | −0.27 | 0.004596 |
| DCC | rs1893572 | rs7228674 | 0.77 | T | G16 | 0.28 | 0.004286 |
| DCC | rs1893572 | rs7228674 | 0.77 | T | N1 | 0.32 | 0.002084 |
| DCC | rs1893572 | rs7228674 | 0.77 | T | N2 | 0.26 | 0.004955 |

TABLE 15-continued

Alleles Influencing Specific Psychiatric Endophenotypes

| Gene Name | Table B SNP | Test SNP in linkage disequilibrium | r² | Allele | PANSS | Beta | P |
|---|---|---|---|---|---|---|---|
| DCC | rs1893572 | rs7228674 | 0.77 | T | N6 | 0.28 | 0.004787 |
| DCC | rs1893572 | rs9807201 | 0.65 | A | G7 | 0.32 | 0.000156 |
| DCC | rs1893572 | rs9807201 | 0.65 | A | N3 | 0.30 | 0.001024 |
| DCC | rs1431748 | rs4998815 | 0.61 | G | G12 | −0.28 | 0.004202 |
| DCC | rs950278 | rs12967277 | 0.60 | G | G12 | 0.28 | 0.002738 |
| DCC | rs950278 | rs12455180 | 0.53 | T | P2 | −0.25 | 0.008191 |
| DCC | rs2229080 | rs12455180 | 0.64 | T | P2 | −0.25 | 0.008191 |
| DCC | rs1431748 | rs9953016 | 0.81 | C | N2 | −0.29 | 0.001508 |
| DCC | rs1431748 | rs7504750 | 0.63 | C | G2 | −0.32 | 0.001379 |
| DCC | rs8096519 | rs11082964 | 0.95 | G | N2 | 0.30 | 0.004634 |
| DCC | rs12457407 | rs9954344 | 0.61 | G | P2 | −0.27 | 0.004541 |
| DCC | rs6508235 | rs9954344 | 0.62 | G | P2 | −0.27 | 0.004541 |
| DCC | rs7506904 | rs9954344 | 0.69 | G | P2 | −0.27 | 0.004541 |
| DCC | rs4940251 | rs9954344 | 0.86 | G | P2 | −0.27 | 0.004541 |
| DCC | rs2270954 | rs2270954 | N/A | A | P6 | −0.46 | 0.002603 |
| BMP7 | rs10375 | rs6123669 | 0.91 | C | G14 | −0.21 | 0.001474 |
| BMP7 | rs6014947 | rs6123669 | 0.97 | C | G14 | −0.21 | 0.001474 |
| BMP7 | rs230198 | rs230198 | N/A | G | G15 | −0.25 | 0.004865 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a human subject having schizophrenia (SZ), the method comprising:
    selecting a human subject having SZ;
    performing an assay to determine a Functional Sma and Mad related protein (SMAD) Suppressing Element 18 (FUSSEL18) haplotype for the selected subject, wherein the FUSSEL18 haplotype comprises an allele of single nucleotide polymorphism rs17785419; and
    identifying a selected subject having an A allele at rs17785419 as less likely to have a negative side effect in response to perphenazine compared to a subject not having an A allele at rs17785419, or identifying a selected subject not having an A allele at rs17785419 as more likely to have a negative side effect in response to perphenazine compared to a subject having an A allele at rs17785419; and
    administering a treatment comprising perphenazine to a selected subject identified as having an A allele at rs17785419 or administering a treatment not comprising perphenazine to a selected subject identified as not having an A allele at rs17785419.

2. The method of claim 1, wherein a treatment comprising perphenazine is administered to a selected subject having an A allele at rs17785419.

3. The method of claim 1, further comprising obtaining a sample comprising genomic DNA from the selected subject.

4. The method of claim 1, wherein the selected subject has:
    (a) a parent who has SZ, schizoaffective disorder (SD), or schizotypal personality disorder (SPD);
    (b) a sibling who has SZ, SD, or SPD; or
    (c) a second degree relative who has SZ, SD, or SPD.

5. The method of claim 1, further comprising selecting or excluding the selected subject for enrollment in a clinical trial based on the selected subject's haplotype.

6. The method of claim 1, further comprising stratifying a population of selected subjects for analysis of a clinical trial based on the haplotypes in the selected subjects.

7. The method of claim 1, further comprising confirming a diagnosis of SZ in the selected subject using psychometric instruments.

8. The method of claim 1, further comprising stratifying the selected subjects into biologically similar groups based on their haplotypes in order to determine a differential diagnosis.

9. The method of claim 1, wherein the selected subject is determined to have SZ based, in part, on his or her Positive and Negative Syndrome Scale score.

10. The method of claim 1, wherein a treatment not comprising perphenazine is administered to a selected subject identified as not having an A allele at rs17785419.

11. A method of treating a human subject having schizophrenia (SZ), the method comprising:
    selecting a human subject having SZ;
    performing an assay to determine a functional Sma and Mad related protein (SMAD) suppressing element 18 (FUSSEL18) haplotype for the selected subject, wherein the FUSSEL18 haplotype comprises an allele of single nucleotide polymorphism rs17785419;
    identifying a selected subject having an A allele at rs17785419 or identifying a selected subject not having an A allele at rs17785419; and
    administering a treatment comprising perphenazine to a selected subject identified as having an A allele at rs17785419, or administering a treatment not comprising perphenazine to a selected subject not having an A allele at rs17785419.

12. The method of claim 11, wherein a treatment comprising perphenazine is administered to a selected subject identified as having an A allele at rs17785419.

13. The method of claim 11, further comprising obtaining a sample comprising genomic DNA from the selected subject.

14. The method of claim 11, wherein the selected subject is determined to have SZ based, in part, on his or her Positive and Negative Syndrome Scale score.

15. The method of claim 11, wherein the selected subject has:

(a) a parent who has SZ, schizoaffective disorder (SD), or schizotypal personality disorder (SPD);
(b) a sibling who has SZ, SD, or SPD, and an unaffected parent; or
(c) a second degree relative who has SZ, SD, or SPD.

16. The method of claim 11, wherein a treatment not comprising perphenazine is administered to a selected subject identified as not having an A allele at rs17785419.

17. The method of claim 11, further comprising selecting or excluding the selected subject for enrollment in a clinical trial based on the selected subject's haplotype.

18. The method of claim 11, further comprising stratifying a population of selected subjects for analysis of a clinical trial based on the haplotypes in the selected subjects.

19. The method of claim 11, further comprising confirming a diagnosis of SZ in the selected subject using psychometric instruments.

20. The method of claim 11, further comprising stratifying the selected subjects into biologically similar groups based on their haplotypes in order to determine a differential diagnosis.

21. A method of treating a human subject having schizophrenia (SZ), the method comprising:
   selecting a human subject having SZ;
   performing an assay to determine a functional Sma and Mad related protein (SMAD) Suppressing Element 18 (FUSSEL18) haplotype for the selected human subject, wherein the FUSSEL18 haplotype comprises an allele of single nucleotide polymorphism rs17785419;
   identifying a selected subject having an A allele at rs17785419 or identifying a selected subject not having an A allele at rs17785419;
   selecting a treatment comprising perphenazine for a selected subject identified as having an A allele at rs17785419, or selecting a treatment not comprising perphenazine for a selected subject identified as not having an A allele at rs17785419; and
   administering a treatment comprising perphenazine to a selected subject identified as having an A allele at rs17785419, or administering a treatment not comprising perphenazine to a selected subject identified as not having an A allele at rs17785419.

22. The method of claim 21, further comprising obtaining a sample comprising genomic DNA from the selected subject.

23. The method of claim 21, wherein the selected subject is determined to have SZ based, in part, on his or her Positive and Negative Syndrome Scale score.

24. The method of claim 21, wherein the selected subject has:
(a) a parent who has SZ, schizoaffective disorder (SD), or schizotypal personality disorder (SPD);
(b) a sibling who has SZ, SD, or SPD, and an unaffected parent; or
(c) a second degree relative who has SZ, SD, or SPD.

25. The method of claim 21, wherein a treatment comprising perphenazine is administered to a selected subject identified as having an A allele at rs17785419.

26. The method of claim 21, wherein a treatment not comprising perphenazine is administered to a selected subject identified as not having an A allele at rs17785419.

27. The method of claim 21, further comprising selecting or excluding the selected subject for enrollment in a clinical trial based on the selected subject's haplotype.

28. The method of claim 21, further comprising stratifying a population of selected subjects for analysis of a clinical trial based on the haplotypes in the selected subjects.

29. The method of claim 21, further comprising confirming a diagnosis of SZ in the selected subject using psychometric instruments.

30. The method of claim 21, further comprising stratifying the selected subjects into biologically similar groups based on their haplotypes in order to determine a differential diagnosis.

* * * * *